United States Patent [19]

Gosteli et al.

[11] Patent Number: 4,952,690
[45] Date of Patent: Aug. 28, 1990

[54] 6-SUBSTITUTED THIA-AZA COMPOUNDS

[75] Inventors: Jacques Gosteli, Basel; Ivan Ernest, Birsfelden, both of Switzerland; Marc Lang, Mulhouse, France; Robert B. Woodward, Cambridge, Mass.

[73] Assignee: Ciba-Geigy Corporation, Ardsley, N.Y.

[21] Appl. No.: 396,783

[22] Filed: Aug. 21, 1989

Related U.S. Application Data

[60] Continuation of Ser. No. 152,526, Feb. 5, 1988, abandoned, which is a division of Ser. No. 57,082, Jun. 3, 1987, abandoned, which is a division of Ser. No. 208,105, Nov. 18, 1980, Pat. No. 4,692,442, which is a continuation of Ser. No. 7,453, Jan. 29, 1979, abandoned.

[30] Foreign Application Priority Data

Feb. 2, 1978 [CH] Switzerland ............... 1140/78-3

[51] Int. Cl.$^5$ ............... C07D 205/09; C07D 205/08; C07D 499/00; A61K 31/425
[52] U.S. Cl. ............... 540/357
[58] Field of Search ............... 540/357

[56] References Cited

U.S. PATENT DOCUMENTS

| | | | |
|---|---|---|---|
| 4,123,539 | 10/1978 | DiNinno | 424/270 |
| 4,168,314 | 9/1979 | Christensen et al. | 424/270 |
| 4,260,618 | 4/1981 | Christensen | 424/263 |
| 4,272,437 | 6/1981 | Menard | 540/310 |
| 4,331,676 | 5/1982 | Gosteli et al. | 424/270 |
| 4,364,865 | 12/1982 | Ernest et al. | 260/239 A |
| 4,431,588 | 2/1984 | Pfaender | 540/310 |
| 4,447,360 | 5/1984 | Gosteli et al. | 260/239 A |
| 4,500,457 | 2/1985 | Gosteli et al. | 260/245.2 R |
| 4,515,717 | 5/1985 | Gosteli et al. | 260/239 A |
| 4,518,533 | 5/1985 | Gosteli et al. | 260/245.4 |
| 4,524,028 | 6/1985 | Gosteli et al. | 260/239 A |
| 4,543,257 | 9/1985 | Cama et al. | 540/310 |
| 4,614,614 | 9/1986 | Ernest et al. | 540/359 |
| 4,616,007 | 10/1986 | Lang | 514/192 |
| 4,656,165 | 4/1987 | Lang | 514/192 |
| 4,826,832 | 5/1989 | Lang | 540/310 |

*Primary Examiner*—Mark L. Berch
*Attorney, Agent, or Firm*—JoAnn Villamizar

[57] ABSTRACT

The invention relates to azetidin-2-ones of the formula

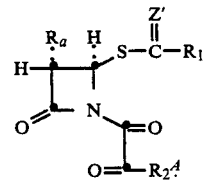

wherein $R_a$ represents hydroxy-lower alkyl, $R_1$ represents hydrogen, an organic radical bonded by a carbon atom to the ring carbon atom or an etherified mercapto group, $R_2^A$ together with the carbonyl group to which it is attached is a protected carboxyl group and $Z'$ is oxygen, sulfhur or an optionally substituted methylidene group, functional groups in the radicals $R_a$, $R_1$ and $Z'$ optionally being in protected form. The azetidinones are useful intermediates for the preparation of penem antibiotics.

12 Claims, No Drawings

6-SUBSTITUTED THIA-AZA COMPOUNDS

CROSS REFERENCE TO RELATED APPLICATION

This application is a continuation application of application Ser. No. 152,526 filed Feb. 5, 1988, now abandoned; which is a divisional application of application Ser. No. 057,082, filed June 3, 1987, now abandoned, which is a divisional application of application Ser. No. 208,105 filed Nov. 18, 1980 now U.S. Pat. No 4,692,442, which is a continuation application of application Ser. No. 007,453 filed Jan. 29, 1979, now abandoned.

The present invention relates to new bicyclic thia-aza compounds containing a β-lactam ring substituted in the 3-position and having antibiotic properties.

Since the discovery of penicillin, numerous bicyclic thia-aza compounds having a β-lactam structure have become known. A survey of earlier works is made by E. H. Flynn, "Cephalosporins and Penicillins", Academic Press, New York and London, 1972. More recent developments are described by J. Cs. Jászberényi et al., Progr. Med. Chem., Vol. 12, 1975, 395–477, and a P. G. Sammes, Chem. Rev. 1976, Vol. 76, No. 1, 113–155 and by various authors at an international symposium of the Chemical Society held in Cambridge, England in June, 1976, (subsequent publication: J. Elks, "Recent Advances in the Chemistry of β-lactam Antibiotics", The Chemical Society, Burlington House, London, 1977).

Apart from the usual penam and cephem compounds carrying an acylamino group in the 6- or 7-position, such compounds that are unsubstituted in these positions have also become known, for example 3-carboxy-2,2-dimethylpenam (J. P. Clayton, J. Chem. Soc., 1969, 2123) and 3-methyl-4-carboxy-3-cephem (K. Kühlein, Liebigs Ann., 1974, page 369 and D. Bormann, ibid., page 1391). 3-carboxy-2,2-dimethylpenam compounds, that instead of the customary 6β-acylamino group have a 6α-chloro or 6α-bromo group, have been described by I. McMillan and R. J. Stoodley, Tetrahedron Lett. 1205 (1966), and J. Chem. Soc. C 2533 (1968), whilst corresponding 6α-hydroxy-, 6α-acetoxy- and 6α-phenoxyacetoxy-2,2-dimethylpenam-3-carboxylic acids have been described by D. Hauser and H. P. Sigg, Helv. Chimica Acta 50, 1327 (1967). None of these compounds, however, has any, or any substantial, antibiotic activity.

6-acylamino-2-penem-3-carboxylic acid compounds having an antibiotic activity that contain the novel 2-penem ring system are described in DOS No. 2 655 298.

2-penem compounds carrying in the 6-position substituents other than acylamino are not so far known.

The problem underlying the present invention is to produce bicyclic thia-aza compounds containing a β-lactam ring that possess the 2-penem ring system substituted in the 6-position and that are active against both penicillin-sensitive and penicillin-resistant bacteria.

The manufacture according to the invention of the novel compounds and the new intermediates required therefor open up new fields in which research into other commercially valuable compounds can be carried out.

The ring system of the compounds of the present invention has the formula

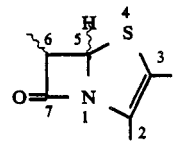

and may systematically be called 7-oxo-4-thia-1-azabicyclo[3,2,0]hept-2-ene. For the sake of simplicity it is referred to hereinafter as "2-penem", wherein the following numbering derived from penam and customary in penicillin chemistry shall be used:

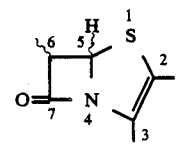

The present invention relates to 2-penem-3-carboxylic acid compounds of the formula

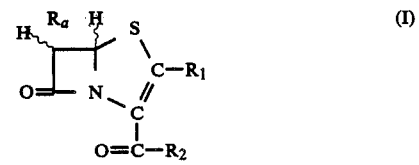

(I)

in which

R$_a$ represents an organic radical bonded by a carbon atom to the ring carbon atom, a free, etherified or esterified hydroxy or mercapto group or a halogen atom, R$_1$ represents hydrogen, an organic radical bonded by a carbon atom to the ring carbon atom, or an etherified mercapto group, and R$_2$ represents a hydroxy group or an radical that together with the carbonyl grouping —C(=O)— forms a protected carboxyl group, and to salts of such compounds with salt-forming groups, processes for the manufacture of such compounds, pharmaceutical preparations containing compounds of the formula I with pharmacological properties, and the use of the new compounds either as pharmacologically active substances, preferably in the form of pharmaceutical preparations, or as intermediates.

An organic radical R$_a$ bonded by a carbon atom to the ring carbon atom is especially a saturated or unsaturated, optionally substituted, aliphatic, cycloaliphatic, cycloaliphatic-aliphatic, aromatic or aliphatic hydrocarbon radical having up to 18, preferably up to 10, carbon atoms, or an optionally substituted heterocyl or heterocyclyl-lower alkyl radical having up to 10 carbon atoms and up to 4 ring hetero atoms selected from the group nitrogen, oxygen and/or sulphur, especially optionally substituted lower alkyl or lower alkenyl, optionally functionally modified carboxyl, or optionally substituted cycloalkyl, cycloalkenyl, cycloalkyl-lower alkyl, cycloalkyl-lower alkenyl, cycloalkenyl-lower alkyl, phenyl, phenyl-lower alkyl or phenyl-lower alkenyl. Examples of substituents of such radicals are optionally functionally modified, such as optionally etherified or esterified hydroxy or mercapto groups, for example hydroxy, lower alkoxy, for example methoxy or ethoxy, lower alkanoyloxy, for example acetoxy or propionoxy, hydroxysulphonyloxy present in said form, halogen atoms, for example chlorine or bromine, or lower alkylthio groups, for example methylthio; optionally functionally modified carboxyl groups, such as carboxyl, lower alkoxycarbonyl, for example :methoxycarbonyl or ethoxycarbonyl groups, carbamoyl or cyano; also nitro; sulpho present in salt form, or optionally substituted amino, such as amino mono-substituted or di-substituted by lower alkyl, for example methyl or ethyl or by acyl, such as lower alkanoyl, for example acetyl, or amino di-substituted by lower alkylene, for example 1,4-butylene or 1,5-pentylene.

A lower alkyl radical $R_a$ contains up to 7, especially up to 4, carbon atoms, and is, for example, methyl, ethyl, propyl, isopropyl, butyl, isobutyl, tert.-butyl or pentyl. Substituted lower alkyl $R_a$ is especially substituted methyl, ethyl or propyl, the substituents standing especially in the 1-, but also in the 2- or 3-position, and is, for example, hydroxy-lower alkyl, such as hydroxymethyl, hydroxyethyl or hydroxypropyl; lower alkoxy-lower alkyl, such as lower alkoxymethyl, lower alkoxyethyl or lower alkoxypropyl, for example methoxymethyl, methoxyethyl or methoxypropyl; lower alkanoyloxy-lower alkyl, such as lower alkanoyloxymethyl, lower alkanoyloxyethyl or lower alkanoyloxypropyl, for example acetoxymethyl, propionoxymethyl, acetoxyethyl, acetoxypropyl, in salt form, for example in the form of an alkali metal salt, such as a sodium salt; or hydroxysulphonyloxy-lower alkyl, such as hydroxysulphonyloxymethyl, hydroxysulphonyloxyethyl or hydroxysulphonyloxypropyl, present in the form of an ammonium salt; halo-lower alkyl, such as halomethyl, haloethyl or halopropyl, for example chloroethyl or bromoethyl or chloropropyl or bromopropyl; lower alkylthio-lower alkyl, such as methylthiomethyl, methylthioethyl, methylthiopropyl or tert.-butylthiomethyl; lower alkoxycarbonyl-lower alkyl, such as lower alkoxycarbonylmethyl or lower alkoxycarbonylethyl, for example, methoxycarbonylmethyl, methoxycarbonylethyl, ethoxycarbonylmethyl or ethoxycarbonylethyl; cyano-lower alkyl, such as cyanomethyl or cyanoethyl; sulpho-lower alkyl, such as sulphomethyl, sulphoethyl or sulphopropyl, in which the sulpho group is present in salt form, for example in the form of an alkali metal salt, such as a sodium salt, or in the form of an ammonium salt; or optionally protected, for example acetylated, amino-lower alkyl, such as aminomethyl, aminoethyl or aminopropyl.

A lower alkenyl radical $R_a$ contains 2 to 7, especially 2 to 4 carbon atoms, and is, for example, vinyl, allyl or but-2-enyl or but-3-enyl. Substituted lower alkenyl may carry the same substituents as substituted lower alkyl.

An optionally functionally modified carboxyl group $R_a$ is a free carboxyl group or one of the, for example esterified or amidated, carboxyl groups mentioned under the $—C(=O)—R_2^A$ groups, such as lower alkoxycarbonyl, for example methoxycarbonyl, ethoxy henoxycarbonyl optionally substituted, for example, by halogen, such as chlorine, by lower alkoxy. such as methoxy, or by nitro, such as phenoxycarbonyl, o-, m- or p-chlorophenoxycarbonyl, pentachlorophenoxycarbonyl, o-, m- or p-methoxyphenoxycarbonyl or p-nitrophenoxycarbonyl; aminocarbonyl; or substituted aminocarbonyl, such as aminocarbonyl mono-substituted or di-substituted by a lower alkyl group, for example methyl or ethyl.

A cycloalkyl radical $R_a$ has, for example, 3 to 7 carbon atoms and is, for example, cyclopropyl, cyclobutyl, cyclopentyl or cyclohexyl, whereas a cyloalkyl-lower alkyl radical $R_a$ contains, for example, 4 to 7 carbon atoms and is, for example, cyclopropylmethyl, cyclobutylmethyl, cyclopentylmethyl or cyclohexylmethyl.

A cycloalkenyl radical $R_a$ is a corresponding cycloalkyl radical having one or optionally two C—C double bonds, such as cyclohexenyl, for example cyclohexenyl, or cyclohexadienyl, for example cyclohexa-1,4-dienyl A cycloalkyl-lower alkenyl radical or cycloalkenyl-lower alkyl radical $R_a$ is, for example, cyclohexylvinyl, cyclohexylallyl, or cyclohexenylmethyl or cyclohexa-1,4-dienylmethyl.

A phenyl or a phenyl-lower alkyl radical, for example a benzyl or 1- or 2-phenylethyl radical $R_a$ may be substituted, preferably in the aromatic radical, for example by lower alkyl, such as methyl or ethyl, by lower alkoxy, such as methoxy, or by halogen, such as fluorine or chlorine, further by nitro or by amino, wherein phenyl-lower alkyl may be substituted in the position, for example, by hydroxy, hydroxysulphonyloxy, carboxy, sulpho or amino In a heterocyclyl or heterocyclyl-lower alkyl radical $R_a$, a heterocyclyl radical is a radical that is preferably of aromatic nature and is bonded by a carbon atom, such as pyridyl, for example pyridyl, pyrid-3-yl or pyrid-4-yl, thienyl, for example thien-2-yl, or furyl, for example fur-2-yl, or a corresponding pyridyl-, thienyl- or furyl-lower alkyl, especially -methyl radical, wherein heterocyclyl-lower alkyl may be substituted in the α-position, for example, by hydroxy, hydroxysulphonyloxy, carboxy, sulpho or amino.

A phenyl- or heterocyclyl-lower alkenyl radical $R_a$ is a lower alkenyl radical, for example phenylvinyl or furylallyl, substituted in the same manner as a corresponding lower alkyl radical A phenyl-, naphthyl- or heterocyclyl-lower alkenyl radical $R_a$ is a lower alkenyl radical, for example phenylvinyl or furylallyl, substituted in the same manner as a corresponding lower alkyl radical.

An etherified hydroxy group $R_a$ is etherified by an optionally substituted aliphatic, cycloaliphatic, cycloaliphatic-aliphatic, aromatic or araliphatic hydrocarbon radical having up to 18, especially up to 10 carbon atoms, and is especially optionally substituted lower alkoxy, cycloalkoxy, cycloalkyllower alkoxy, phenoxy, naththyloxy or phenyl-lower alkoxy. Examples of substituents of such radicals are optionally functionally modified, such as optionally etherified or esterified, hydroxy or mercapto groups, for example hydroxy, lower alkoxy, for example methoxy or ethoxy, lower alkanoyloxy, for example acetoxy or propionoxy, halogen, for example chlorine or bromine, or lower alkylthio, for example methylthio; or optionally functionally modified carboxyl groups, such as carboxyl, lower alkoxycarbonyl, for example methoxycarbonyl or ethoxycarbonyl, carbamoyl or cyano; also nitro; or optionally substituted amino, such as amino mono-substituted or di-substituted by lower alkyl, for example methyl or ethyl, or by acyl, such as lower alkanoyl, for example acetyl, or amino di-substituted by lower alkylene, for example 1,4-butylene or 1,5-pentylene.

A lower alkoxy radical R contains up to 7, especially up to 4, carbon atoms, and is, inter alia, methoxy, ethoxy, propoxy, isopropoxy, butoxy, isobutoxy, tert.-butoxy or pentoxy. Substituted lower alkoxy R is especially substituted methoxy, ethoxy or propoxy, the substituents standing in the 1-, 2- or 3-position,. such as methoxymethoxy, ethoxymethoxy, methoxyethoxy or methoxypropoxy; lower alkanoyloxymethoxy, lower alkanoyloxyethoxy or lower alkanoyloxypropoxy, such as acetoxymethoxy, acetoxyethoxy or acetoxypropoxy; halomethoxy; haloethoxy or halopropoxy, such as chloroethoxy or bromoethoxy or chloropropoxy or bromopopoxy; lower alkoxycarbonylmethoxy or lower r alkoxycarbonylethoxy, for example methoxycarbonylmethoxy, ethoxycarbonylmethoxy or methoxycrbonylethoxy; cyanomethoxy, cyanoethoxy, or optionally protected aminomethoxy, aminoethoxy or aminopropoxy.

A cycloalkoxy group $R_a$ has, for example, 3 to 7 carbon atoms and is, for example, cyclopropoxy, cyclobutoxy, cyclopentoxy or cyclohexyloxy.

A cycloalkyl-lower alkoxy radical $R_a$ has, for example, 4 to 7 carbon atoms and is, for example, cyclopropylmethoxy, cyclobutylmethoxy, cyclopentylmethoxy or cyclohexylmethoxy.

A phenoxy or phenyl-lower alkoxy radical $R_a$, for example a benzyl- or 1- or 2-phenylethoxy radical may be substituted, preferably in the aromatic radical, for example by lower alkyl, such as methyl or ethyl, by lower alkoxy, such as methoxy, by halogen, such as fluorine or chlorine, or by nitro or amino.

An esterified hydroxy group $R_a$ is a hydroxy group esterified by an acyl radical of an optionally substituted aliphatic, cycloaliphatic, cycloaliphaticaliphatic, aromatic or araliphatic carboxylic acid having up to 18 carbon atoms. Such groups are especially optionally substituted lower alkanoyloxy, cycloalkanoyloxy, cycloalkyl-lower alkanoyloxy, benzoyloxy, or phenyl-lower alkanoyloxy. Substituents of such radicals are, for example, optionally functionally modified, such as optionally etherified or esterified, hydroxy or mercapto groups, for example hydroxy, lower alkoxy, for example methoxy or ethoxy, aryloxy, for example phenoxy, lower alkanoyloxy, for example acetoxy or propionoxy, halogen, for example chlorine or bromine, or lower alkylthio, for example methylthio: or optionally functionally modified carboxyl groups, such as carboxyl, lower alkoxycarbonyl, for example methoxycarbonyl or ethoxycarbonyl, carbamoyl or cyano; also nitro; or optionally substituted amino, for example amino mono-substituted or di-substituted by lower alkyl, for example methyl or ethyl, or by acyl, such as lower alkanoyl, for example acetyl, or amino disubstituted by lower alkylene, for example 1,4-butylene or 1,5-pentylene.

A lower alkanoyloxy radical $R_a$ contains up to 7, especially up to 4, carbon atoms, and is, for example, formyloxy, acetoxy, propionoxy or butyryloxy. Substituted lower alkanoyloxy $R_a$ is especially sub stituted acetoxy, for example, hydroxyacetoxy, methoxyacetoxy, phenoxyacetoxy, haloacetoxy, for example chloroacetoxy or bromoacetoxy, cyanoacetoxy or optionally protected glycyloxy.

A cycloalkanoyloxy radical $R_a$ has 4 to 8 carbon atoms and is, for example, cyclopropylcarbonyloxy, cyclobutylcarbonyloxy, cyclopentylcarbonyloxy or cyclohexylcarbonyloxy, or a corresponding radical substituted, for example, in the 1-position, for example by hydroxy or amino.

A cycloalkyl-lower alkanoyloxy radical $R_a$ has 5 to 9 carbon atoms and is, for example, cyclopropylacetoxy, cyclobutylacetoxy, cyclohexylacetoxy or cyclohexylpropionoxy, or a corresponding radical substituted, for example, in the 1-position, for example by hydroxy or amino.

A benzoyloxy or phenyl-lower alkanoyloxy radical $R_a$, for example a phenylacetoxy radical, may be substituted, preferably in the aromatic radical, for example, by lower alkyl, such as methyl or ethyl, by lower alkoxy, such as methoxy, by halogen, such as fluorine or chlorine, by nitro or by optionally protected hydroxy or amino. In the phenyl-lower alkanoyloxy radical, optionally substituted, for example protected, hydroxy or optionally substituted, for example protected, amino, may also stand in the aliphatic moiety, especially in the 2-position.

An etherified mercapto group $R_a$ is etherified by an optionally substituted aliphatic, cycloaliphatic, cycloaliphatic-aliphatic, aromatic or araliphatic hydrocarbon radical having up to 18, especially up to 10 carbon atoms, and is especially optionally substituted lower alkylthio, cycloalkylthio, cycloalkyl-lower alkylthio, phenylthio or phenyl-lower alkylthio. Examples of substituents of such radicals are optionally functionally modified, such as optionally etherified or esterified, hydroxy or mercapto, for example, hydroxy, lower alkoxy, for example methoxy or ethoxy, lower alkanoyloxy, for example acetoxy or propionoxy, halogen, for example chlorine or bromine, lower alkylthio, for example methylthio; or optionally functionally modified carboxyl groups, such as carboxyl, lower alkoxycarbonyl, for example methoxycarbonyl or ethoxycarbonyl, carbamoyl or cyano; also nitro; or optionally substituted amino, such as amino mono-substituted or di-substituted by lower alkyl, for example methyl or ethyl, or by acyl, such as lower alkanoyl, for example acetyl, or amino di-substituted by lower alkylene, for example by 1,4-butylene or 1,5-pentylene.

A lower alkylthio radical $R_a$ contains up to a especially up to 4, carbon atoms, and is, inter alia methylthio, ethylthio, propylthio, isopropylthio, butylthio, isobutylthio, tert.-butylthio or pentylthio. Substituted lower alkylthio $R_a$ is especially substituted methylthio, ethylthio or propylthio, the substituents standing in the 1-, 2- or 3-position, such as methoxymethylthio, ethoxymethylthio, methoxyethylthio or methoxypropylthio; lower alkanoyloxymethylthio, lower alkanoyloxyethylthio or lower alkanoyloxypropylthio, such as acetoxymethylthio, acetoxyethylthio or acetoxypropylthio; halomethylthio, haloethylthio or halopropylthio, for example chloroethylthio or bromoethylthio, or chloropropylthio or bromopropylthio; lower alkoxycarbonylmethylthio or lower alkoxycarbonylethylthio, for example methoxycarbonylethylthio; cyanomethylthio; cyanoethylthio; or optionally protected, for example N-acylated, aminomethylthio, aminoethylthio or aminopropylthio.

A cycloalkylthio group $R_a$ has, for example, 3 to 7 carbon atoms and is, for example, cyclopropylthio, cyclobutylthio, cyclopentylthio or cyclohexylthio.

A cycloalkyl-lower alkylthio radical $R_a$ has, for example, 4 to 7 carbon atoms and is, for example, cyclopropylmethylthio, cyclobutylmethylthio, cyclopentylmethylthio or cyclohexylmethylthio.

A phenylthio or phenyl-lower alkylthio radical $R_a$, for example a benzylthio or 1- or 2-phenyl-lower alkylthio radical, for example a benzylthio or 1- or 2-phenylethylthio radical, may be substituted, preferably in the aromatic radical, for example may lower alkyl, such as methyl or ethyl, by lower alkoxy, such as methoxy, by halogen, such as fluorine or chlorine, by nitro or by amino.

An esterified mercapto group $R_a$ is a mercapto group esterified by an acyl radical of an optionally substituted aliphatic, cycloaliphatic, cycloaliphaticaliphatic, aromatic or araliphatic carboxylic acid having up to 18 carbon atoms. Such radicals are especially optionally substituted lower alkanoylthio, cycloalkanoylthio, cycloalkyl-lower alkanoylthio, benzoylthio or phenyl-lower alkanoylthio. Substituents of such radicals are, for example, optionally functionally modified, such as optionally etherified or esterified, hydroxy or mercapto groups, for example hydroxy, lower alkoxy, for example methoxy or ethoxy, aryloxy, for example phenoxy, lower alkanoyloxy, for example acetoxy or propionoxy, halogen, for example chlorine or bromine, or lower alkylthio, for example methylthio; or optionally functionally modified carboxyl groups, such as carboxyl, lower alkoxycarbonyl, for example methoxycarbonyl or ethoxycarbonyl, carbamoyl or cyano; also nitro; or optionally substituted amino, such as amino mono-substituted or di-substituted for example by lower alkyl, for example methyl or ethyl, by acyl, such as lower alkanoyl, for example acetyl, or amino di-substituted by lower alkylene, for example 1,4-butylene or 1,5-pentylene.

A lower alkanoylthio radical $R_a$ contains up to 7, especially up to 4, carbon atoms and is, for example, formylthio, acetylthio, propionylthio or butyrylthio. Substituted lower alkanoylthio $R_a$ or $R_a$ is especially substituted acetylthio, for example hydroxyacetylthio, methoxyacetylthio or phenoxyacetylthio; haloacetylthio, for example chloroacetylthio or bromoacetylthio; cyanoacetylthio or optionally protected glycylthio.

A cycloalkanoylthio radical $R_a$ has 4 to 8 carbon atoms and is, for example, cyclopropylcarbonylthio, cyclobutylcarbonylthio, cyclopentylcarbonylthio or cyclohexylcarbonylthio, or a corresponding radical substituted, for example, in the 2-position, for example by hydroxy or amino.

A cycloalkyl-lower alkanoylthio radical $R_a$ has 5 to 9 carbon atoms and is, for example, cyclopropylacetylthio, cyclobutylacetylthio, cyclohexylacetylthio or cyclohexylpropionylthio, or a corresponding radical substituted, for example, in the 2-position, for example by hydroxy or amino.

A benzoylthio or phenyl-lower alkanoylthio radical $R_a$, for example a phenylacetylthio radical, may be substituted, preferably in the aromatic radical, for example by lower alkyl such as methyl or ethyl, by lower alkoxy, such as methoxy, by halogen, such as fluorine or chlorine, by nitro or by optionally protected hydroxy or amino. In the phenyl-lower alkanoylthio radical, optionally substituted, for example protected hydroxy or optionally substituted for example protected amino may also stand in the aliphatic moiety, especially in the 2-position.

$R_a$ in the meaning of a halogen atom is iodine or especially fluorine, chlorine or bromine.

An organic radical $R_1$ bonded by a carbon atom to the ring carbon atom is especially a saturated or unsaturated, optionally substituted aliphatic, cycloaliphatic, cycloaliphatic-aliphatic, aromatic or araliphatic hydrocarbon radical having up to 18, preferably up to 10, carbon atoms, or an optionally substituted heterocyclyl or heterocyclyl-lower alkyl radical having up to 10 carbon atoms and up to 4 ring hetero atoms selected from the group nitrogen, oxygen and/or sulphur, especially optionally substituted lower alkyl or lower alkenyl, optionally functionally modified carboxyl, or optionally substituted cycloalkyl, cycloalkenyl, cycloalkyl-lower alkyl, cycloalkyl-lower alkenyl, cycloalkenyl-lower alkyl, phenyl, phenyl-lower alkyl or phenyl-lower alkenyl. Examples of substituents such radicals are optionally functionally modified, such as optionally etherified or esterified, hydroxy or mercapto groups, for example hydroxy, lower alkoxy, for example methoxy or ethoxy, or lower alkanoyloxy, for example acetoxy or propionoxy groups, halogen atoms, for example chlorine or bromine, or lower alkylthio groups, for example methylthio, or a heterocyclylthio radical; this heterocyclyl radical is optionally substituted, has aromatic properties or is partially saturated; substituents are, inter alia, lower alkyl, especially methyl; hydroxy-lower alkyl, for example hydroxymethyl; carboxy-lower alkyl, for example carboxymethyl or 1- or 2-carboxyethyl; optionally N-substituted amino-lower alkyl, such as di-lower alkylamino-lower alkyl, for example dimethylaminoethyl; sulpho-lower alkyl present in salt form, for example sulphomethyl or 1- or 2-sulphoethyl present in the form of a sodium salt; cycloalkyl, for example cyclopentyl or cyclohexyl; aryl, such as phenyl optionally substituted by halogen, for example chlorine, or by nitro; aryl-lower alkyl, for example benzyl; or functional group, such as halogen, for example fluorine, chlorine or bromine; optionally substituted amino, such as amino optionally mono-substituted or di-substituted by lower alkyl, for example amino, methylamino or dimethylamino; nitro; hydroxy; lower alkoxy, for example methoxy or ethoxy; or optionally functionally modified carboxyl, such as carboxyl, esterified carboxyl, such as lower alkoxycarbonyl, for example methoxycarbonyl or ethoxycarbonyl, optionally substituted, such as N-mono-lower alkylated or N,N-di-lower alkylated carbamoyl, for example N-methylcarbamoyl, or N,N-dimethylcarbamoyl, or cyano; as well as oxo or oxido; wherein one or more such substituents are present and these are bonded especially to ring carbon atoms, but alternatively, especially lower alkyl and oxido, are bonded to ring carbon atoms; such heterocyclic radicals are especially monocyclic, five-membered, diaza-, triaza-, tetraza-, thiaza-, tiadiaza, thiatriaza-, oxaza- or oxadiazacyclic radicals of aromatic nature optionally containing the above-mentioned substitutents, or corresponding radicals that are optionally substituted, for example by the above-mentioned substituents, having a fused benzene ring, such as benzodiaza- or benzooxazacyclic radicals; monocyclic, six-membered monoazacyclic or diazacyclic radicals of aromatic nature optionally containing the above-mentioned substituents, especially oxido; or corresponding partially saturated radicals optionally substituted, for example by the above-mentioned substituents, especially oxo; or bicyclic, triazacyclic or tetrazacyclic radicals of aromatic nature optionally substituted, for example by the above-mentioned substitutents; or corresponding partially saturated radicals optionally substituted, for example by the above-mentioned substitutents, especially oxo. Examples of such heterocyclyl radicals are imidazolyl, for example imidazol-2-yl; triazolyl optionally substituted by lower alkyl and/or phenyl, for example 1,2,3-triazol-4-yl, 1-methyl-1H-1,2,3-triazol-4-yl, 1H-1,2,4-triazol-3-yl, 5-methyl-1H-1,2,4-triazol-3-yl, 3-methyl-1-phenyl-1H-1,2,4-triazol-5-yl, 4,5-dimethyl-4H-1,2,4-triazol-3-yl or 4-phenyl-4H-1,2,4-triazol-3-yl; tetrazolyl optionally substituted by lower alkyl, -phenyl or halo-phenyl, for example 1H-tetrazol-5-yl, 1-methyl-1H-tetrazol-5-yl, 1-phenyl-1H-tetrazol-5-yl, 1-(4-chlorophenyl)-1H-tetrazol-5-yl, 1-carboxymethyl-1H-tetrazol-5-yl, 1-(2-dimethylaminoethyl)-1H-tetrazol-5-yl or 1-sodium sulphomethyl-1H-tetrazol-5-yl; thiazolyl or isothiazolyl optionally substituted by lower alkyl or thienyl, for example thiazol-2-yl, 4-(thien-2-yl)-thiazol-2-yl, 4,5-dimethylthiazol-2-yl, isothiazol-3-yl, isothiazol-4-yl or isothiazol-5-yl; thiadiazolyl optionally substituted by lower alkyl, for example 1,2,3-thiadiazol-4-yl, 1,2,3-thiadiazol-5-yl, 1,3,4-thiadiazol-2-yl, 2-methyl-1,3,4-thiadiazol-5-yl, 1,2,4-thiadiazol-5-yl or 1,2,5-thiadiazol-3-yl; thiatriazolyl, for example 1,2,3,4-thiatriazol-5-yl; oxazolyl or isoxazolyl optionally substituted by lower alkyl or phenyl, for example oxazol-5-yl, 4-methyloxazol-5-yl, oxazol-2-yl, 4,5-diphenyloxazol-2-yl or 3-methylisoxazol-5-yl oxadiazolyl optionally substituted by lower alkyl, -phenyl, nitro-phenyl or thienyl, for example 1,2,4-oxadiazol-5-yl, 2-methyl-1,3,4-oxadiazol-5-yl, 2-phenyl-1,3,4-oxadiazol-5-yl, 5-(4-nitrophenyl)-1,3,4-oxadiazol-2-yl or 2-(thienyl)-1,3,4-oxadiazol-5-yl; benzimidazolyl optionally substituted by halogen, for example benzimidazol-2-yl or 5-chlorobenzimidazol-2-yl; or benzoxazolyl optionally substituted by halogen or nitro, for example benzoxazol-2-yl, 5-nitrobenzoxazol-2-yl or 5-chlorobenzoxazol-2-yl; 1-oxidopyridyl, for example 1-oxidopyrid-2-yl or 4-chloro-1-oxidopyrid-2-yl; pyridazinyl optionally substituted by hydroxy, for example 3-hydroxypyridazin-6-yl; N-oxidopyridazinyl optionally substituted by lower alkyl, lower alkoxy or halogen, for example 2-oxido pyridazin-6-yl, 3-chloro-1-oxidopyridazin-6-yl, 3-methyl-2-oxidopyridazin-6-yl, 3-methoxy-1-oxidopyridazin-6-yl, 3-ethoxy-1-oxidopyridazin-6-yl, 3-n-butoxy-1-oxidopyridazin-6-yl or 3-(2-ethylhexyloxy)-1-oxidopyridazin-6-yl; or 2-oxo-1,2-dihydropyrimidinyl, optionally substituted by lower alkyl, amino, di-lower alkylamino or carboxy, for example 2-oxo-1,2-dihydropyrimidin-4-yl, 6-methyl-2-oxo-1,2-dihydropyrimidin-4-yl, 5-methyl-2-oxo-1,2-dihydropyrimidin-4-yl, 6-amino-2-oxo-1,2-dihydropyrimidin-4-yl, 6-dimethylamino-2-oxo-1,2-dihyiropyrimidin-4-yl, 5-carboxy-2-oxo-1,2-dihydropyrimidin-4-yl or 6-carboxy-2-oxo-1,2-dihydropyrimidin-4-yl; triazolopyridyl, for example s-triazolo[4,3-a]pyrid-3-yl or 3H-v-triazolo[4,5-b]pyrid-5-yl; or purinyl optionally substituted by halogen and/or lower alkyl, for example purin-2-yl, purin-6-yl or 8-chloro-2-methylpurin-6-yl; also 2-oxo-1,2-dihydropurinyl, for example 2-oxo-1,2-dihydropurin-6-yl]; or optionally functionally modified carboxyl groups, such as carboxyl, lower alkoxy carbonyl, for example methoxycarbonyl or ethoxycarbonyl, carbamoyl or cyano; also nitro; or optionally substituted amino, for example amino mono-substituted or di-substituted by lower alkyl, for example methyl or ethyl, by acyl, such as lower alkanoyl, for example acetyl, or amino di-substituted by lower alkylene, for example 1,4-butylene or 1,5-pentylene.

A lower alkyl radical $R_1$ contains up to 7, especially up to 4, carbon atoms, and is, for example, methyl, ethyl, propyl, isopropyl, butyl, isobutyl, tert.-butyl or pentyl. Substituted lower alkyl is especially substituted methyl, ethyl or propyl, the substituents standing especially in the 1-, but also in the 2- or 3-position, such as hydroxymethyl, hydroxyethyl or hydroxypropyl; lower alkoxymethyl, lower alkoxyethyl or lower alkoxypropyl, for example methoxmethyl, methoxyethyl or methoxypropyl; lower alkanoyloxymethyl, lower alkanoyloxyethyl or lower alkanoyloxypropyl, for example, acetoxymethyl, propionoxymethyl, acetoxyethyl or acetoxypropyl; halomethyl, haloethyl or halopropyl, for example chloroethyl or bromoethyl, or chloropropyl or bromopropyl; methylthiomethyl, methylthioethyl, methylthiopropyl, tert.-butylthiomethyl, 1,2,3-triazol-4-ylthiomethyl, 1H-tetrazol-5-ylthiomethyl, 1-methyl-1H-tetrazol-5-ylthiomethyl, 1-carboxymethyl-1H-tetrazol-5-ylthiomethyl, 1-(2-dimethylaminoethyl)-1H-tetrazol-5-ylthiomethyl or 1-sodium sulphomethyl-1H-tetrazol-5-ylthiomethyl, 1H-tetrazol-5-ylthioethyl, (1-methyl-1H-tetrazol-5-ylthio)-ethyl, 2-methyl-1,3,4-thiadiazol-5-ylthiomethyl; lower alkoxycarbonylmethyl or lower alkoxycarbonylethyl, for example methoxycarbonylmethyl, ethoxycarbonylmethyl or methoxycarbonylethyl; cyanomethyl, cyanoethyl; or optionally protected aminomethyl, aminoethyl or aminopropyl.

A lower alkenyl radical $R_1$ contains 2 to 7, especially 2 to 4, carbon atoms, and is, for example, vinyl, allyl or but-2-enyl or but-3-enyl. Substituted lower alkenyl may carry the same substituents as substituted lower alkyl and is, for example, 2-aminovinyl or 2-acylaninovinyl, such as 2-acetylaminovinyl.

An optionally functionally modified carboxyl group $R_1$ is a free carboxyl group or one of the, for example esterified or oxidated, carboxyl groups mentioned under the groups $-C(=O)-R_2^4$, such as lower alkoxycarbonyl, for example methoxycarbonyl ethoxycarbonyl or tert.-butoxycarbonyl; aryl-lower alkoxycarbonyl, such as benzyloxycarbonyl, p-nitrobenzyloxycarbonyl or diphenylmethoxycarbonyl; aryloxycarbonyl, such as phenoxycarbonyl optionally substituted, for example, by halogen, such as chlorine, by lower alkoxy, such as methoxy, or by nitro, such as phenoxycarbonyl, o-, m- or p-chlorophenoxycarbonyl, pentachlorophenoxycarbonyl, o-, m- or p-methoxyhenoxycarbonyl or p-nitrophenoxycarbonyl; or aminocarbonyl or substituted aminocarbonyl such as aminocarbonyl mono- or disubstituted by, for example lower alkyl, for example methyl or ethyl.

A cycloalkyl radical $R_1$ has, for example, 3 to 7 carbon atoms and is, for example, cyclopropyl, cyclobutyl, cyclopentyl or cyclohexyl, whilst a cycloalkyllower alkyl radical $R_1$ has, for example, 4 to 7 carbon atoms and is, for example, cyclopropylmethyl, cyclobutylmethyl, cyclopentylmethyl or cyclohexylmethyl.

A cycloalkenyl radical $R_1$ is a corresponding cycloalkyl radical having one or optionally two C—C double bonds, such as cyclohexenyl, for example cyclohex-1-enyl, or cyclohexadienyl, for example cyclohexa-1,4-dienyl.

A cycloalkyl-lower alkenyl radical or cycloalkenyl-lower alkyl radical $R_1$ is, for example, cyclohexylvinyl or cyclohexylallyl, or cyclohexenylmethyl or cyclohexa-1,4-dienylmethyl respectively.

A phenyl or phenyl-lower alkyl radical $R_1$, for example a benzyl or 1- or 2-phenylethyl radical, may be substituted, preferably in the aromatic radical, for example by lower alkyl, such as methyl or ethyl, by lower alkoxy, such as methoxy, or by halogen, such as fluorine or chlorine, or also by nitro or amino.

A radical $R_1$ may alternatively represent a heterocyclic or heterocyclic-aliphatic radical bonded by a carbon atom and preferably of aromatic nature, such as pyridyl, for example pyrid-2-yl, pyrid-3-yl or pyrid-4-yl; thienyl, for example thien-2-yl, or furyl, for example fur-2-yl; a corresponding pyridyl-lower alkyl, thienyl-lower alkyl or furyl-lower alkyl radicals, especially pyridylmethyl, thienylmethyl or furylmethyl radicals.

A phenyl- or heterocyclyl-lower alkenyl radical $R_1$ is a lower alkenyl radical substituted in the same manner as a corresponding lower alkyl radical, for example phenylvinyl or furylallyl.

An etherified mercapto group $R_1$ is etherified by an optionally substituted aliphatic, cycloaliphatic, cycloaliphatic-aliphatic, aromatic or araliphatic hydrocarbon radical having up to 18, especially up to 10 carbon atoms, or a heterocyclic radical and is optionally substituted lower alkylthio, lower alkenylthio, cycloalkylthio, cycloalkyl-lower alkylthio, phenylthio, phenyl-lower alkylthio or heterocyclylthio. Substituents of such radicals are, for example, optionally functionally modified, such as optionally etherified or esterified, hydroxy or mercapto, for example hydroxy, lower alkoxy, for example methoxy or ethoxy, lower alkanoyloxy, for example acetoxy or propionoxy, halogen, for example chlorine or bromine, or lower alkylthio, for example methylthio; or optionally functionally modified carboxyl groups, such as carboxyl, lower alkoxycarbonyl, for example methoxycarbonyl or ethoxycarbonyl, carbamoyl or cyano; also nitro; or optionally substituted amino, such as amino mono- or di-substituted such as by lower alkyl, for example methyl or ethyl, or by acyl, such as lower alkanoyl, for example acetyl, or amino di-substituted by lower alkylene, for example by 1,4-butylene or 1,5-pentylene; or the substituents listed below in the case of the individual etherified mercapto groups $R_1$.

A lower alkylthio radical $R_1$ contains up to 7, especially up to 4, carbon atoms, and is, for example, methylthio, ethylthio, propylthio, isopropylthio, butylthio, isobutylthio, tert.-butylthio or pentylthio. Substituted lower alkylthio $R_1$ is, primarily, substituted methylthio, ethylthio or propylthio, the substituents standing in the 1-, 2- or 3-position such as methoxymethylthio, ethoxymethylthio, methoxyethylthio or methoxypropylthio; lower alkanoyloxymethylthio, lower alkanoyloxyethylthio or lower alkanoyloxypropylthio, such as acetoxymethylthio, acetoxyethylthio or acetoxypropylthio; halomethylthio, haloethylthio or halopropylthio, for example chloroethylthio or bromoethylthio, or chloropropylthio or bromopropylthio; lower alkoxycarbonylmethylthio or lower alkoxycarbonylethylthio, for example methoxycarbonylethylthio; cyanomethylthio; cyanoethylthio; or optionally protected, for example acetylated, aminomethylthio, aminoethylthio or aminopropylthio.

A lower alkenylthio radical $R_1$ contains 2 to 7, especially 2 to 4, carbon atoms and is especially 1-lower alkynylthio, for example, vinylthio, prop-1-enylothio, but-1-enylthio or pent-1-enylthio or also 2-lower alkenylthio, for example allylthio. Substituted lower alkenylthio $R_1$ is especially substituted in the 2-position, wherein the substituents that chiefly come into consideration are lower alkoxy, lower alkanoyloxy and optionally protected amino. Thus $R_1$ is, for example, 2-methoxyvinylthio, 2-acetoxyvinylthio, 2-acetylaminovinylthio or correspondingly substituted prop-1-enylthio.

A cycloalkylthio group $R_1$ has, for example, 3 to 7 carbon atoms, and is, for example, cyclopropylthio, cyclobutylthio, cyclopentylthio or cyclohexylthio.

A cycloalkyl-lower alkylthio radical $R_1$ has, for example, 4 to 7 carbon atoms and is, for example, cyclopropylmethylthio, cyclobutylmethylthio, cyclopentylmethylthio or cyclohexylmethylthio.

A phenylthio radical $R_1$ or a phenyl-lower alkylthio radical $R_1$, for example a benzyl- or 1- or 2-phenylethylthio radical, may be substituted, preferably in the aromatic radical, for example by lower alkyl, such as methyl or ethyl, by lower alkoxy, such as methoxy, by halogen, such as fluorine or chlorine, or by nitro or amino.

Heterocyclically etherified mercapto groups $R_1$ are especially etherified by an optionally substituted heterocyclic radical that has 1 to 4 ring nitrogen atoms and optionally a further ring hetero atom selected from oxygen and sulphur and that is bonded to the mercapto group by a ring carbon atom.

Such heterocyclic radicals are especially optionally substituted, for example by the substituents mentioned below, monocyclic, five-membered diaza-, triaza-, tetraza-, thiaza-, thiadiaza-, thiatriaza-, oxaza- or oxadiazacyclic radicals of aromatic nature, or optionally substituted monocyclic six-membered aza- or diaza-cyclic radicals of aromatic or partially saturated character.

Substituents of such heterocyclyl radicals are, inter alia, lower alkyl, especially methyl, as well as ethyl, n-propyl, isopropyl or straight-chained or branched butyl: or lower alkyl substituted by hydroxy, as lower alkoxycarbonyl, sulpho, amidated sulphomono- or di-lower alkylamino, acylamino, as lower alkanoylamino, or by substituted lower alkanoylamino, such as lower alkanoylamino substituted by carboxy or halogen, for example, 2-hydroxyethyl, 2-acetoxyethyl, 2-chloroethyl, carboxymethyl, 2-carboxyethyl, ethoxycarbonylmethyl, 2-ethoxycarbonylethyl, sulphomethyl, 2-sulphoethyl, sulphamylmethyl, 2-sulphamylethyl, 2-aminoethyl, 2-dimethylaminoethyl, or 2-acetylaminoethyl. Further substituents of the heterocyclic radical are cycloalkyl, for example cyclopentyl or cyclohexyl; aryl, such as phenyl optionally substituted by halogen, for example chlorine, or by nitro; aryl-lower alkyl, for example benzyl; or a heterocyclyl radical such as furyl, for example fur-2-yl, thienyl, for example thien-2-yl, or oxazolyl, for example oxazol-2-yl or oxazol-5-yl; or functional groups, such as: halogen, for example fluorine, chlorine or bromine; optionally substituted amino such as amino optionally mono-substituted or di-substituted by lower alkyl, for example, amino, methylamino or dimethylamino; acylamino, such as lower alkanoylamino or lower alkanoylamino substituted by halogen or carboxy, such as acetylamino, 3-chloropropionylamino or 3-carboxypropionylanino; nitro; hydroxy; lower alkoxy, for example methoxy, ethoxy, n-butoxy or 2-ethylhexyloxy; or optionally functionally modified carboxyl, such as carboxy, esterified carboxy, such as lower alkoxycarbonyl, for example methoxycarbonyl or ethoxycarbonyl, optionally substituted, for example N-mono- or N,N-di-lower alkylated carbamcyl, for example, N-methylcarbamoyl or N,N-dimethylcarbamoyl; or cyano; as well as oxo or oxido; wherein one or more such substituents are present and these are bonded especially to ring carbon atoms, but alternatively, especially lower alkyl and oxido, are bonded to ring nitrogen atoms.

Preferred heterocyclically etherified mercapto groups $R_1$ in which the heterocyclic radical is a corresponding monocyclic, five-membered radical, are inter alia imidazolylthio, for example imidazol-2-ylthio; triazolylthio optionally substituted by lower alkyl and/or phenyl, for example, 1H-1,2,3-triazol-4-ylthio, 1-methyl-1H-1,2,3-triazol-4-ylthio, 1H-1,2,4-triazol-3-ylthio, 5-methyl-1H-1,2,4-triazol-3-ylthio, 3-methyl-1- phenyl-1H-1,2,4-triazol-5-ylthio, 4,5-dimethyl -4H-1,2,4-triazol-3-ylthio or 4-phenyl -4H-1,2,4-triazol-3-ylthio; especially tetrazolylthio optionally substituted as stated, for example 1H-tetrazol-5-ylthio, 1-methyl-1H-tetrazol-5-ylthio, 1-carboxymethyl-1H-tetrazol-5-ylthio, 1-(2-carboxyethyl)-1H-tetrazol-5-ylthio, 1-sulphomethyl-1H-tetrazol- 5-ylthio, 1-(2-sulphoethyl)-1H-tetrazol-5-ylthio, 1-(2-dimethylaminoethyl)1H-tetrazol-5-ylthio, 1-phenyl-1H-tetrazol-5-ylthio or 1-(4-chlorophenyl)-1H-tetrazol-5-ylthio; thiazolylthio or isothiazolylthio optionally substituted by lower alkyl or thienyl, for example thiazol-2-ylthio, 4-(thien-2-yl)-thiazol-2-ylthio, 4,5-dimethylthiazol-2-ylthio, isothiazol-3-ylthio, isothiazol-4-ylthio or isothiazol-5-ylthio; especially thiadiazolylthio optionally substituted as stated, for 5-ylthio, 1,3,4-thiadiazol-2-ylthio, 2-methyl-1,3,4-thiadiazol-5-ylthio 2-(3-carboxypropionylamino)-1,3,4-thiadiazol-5-ylthio, 1,2,4-thiadiazol-5-ylthio or 1,2,5-thiadiazol-3-ylthio; thiatriazolylthio, for example 1,2,3,4-thiatriazol-5-ylthio; oxazolylthio or isoxazolylthio optionally substituted as stated, for example oxazol-5-ylthio, 4-methyloxoazol-5-ylthio, oxazol-2-ylthio, 4,5-diphenyloxazol-2-ylthio or 3-methylisoxazol-5-ylthio; or oxadiazolylthio optionally substituted as stated, for example 1,2,4-oxadiazol-5-ylthio, 2-methyl-1,3,4-oxadiazol-5-ylthio, 2-phenyl-1,3,4-oxadiazol-5-ylthio, 5-(4-nitrophenyl)-1,3,4-oxadiazol-2-ylthio or 2-(thien-2-yl)-1,3,4-oxadiazol-5-ylthio.

Preferred heterocyclically etherified mercapto groups $R_1$, in which the heterocyclic radical is a corresponding monocyclic, six-membered radical or a corresponding partially saturated radical, are, inter alia, 1-oxidopyridylthio, optionally substituted by halogen, for example 1-oxidopyrid-2-ylthio or 4-chloro-1-oxidopyrid-2-ylthio; pyridazinylthio optionally substituted by hydroxy, for example 3-hydroxypyridazin-6-ylthio; N-oxidopyridazinylthio optionally substituted by lower alkyl, lower alkoxy or halogen, for example 2-oxidopyridazin-6-ylthio, 3-chloro-1-oxidopyridazin-6-ylthio, 3-methyl-2-oxidopyridazin-6-ylthio, 3-methoxy-1-oxidopyridazin-6-ylthio, 3-ethoxy-1-oxidopyridazin- 6-ylthio, 3-n-butoxy-1-oxidopyridazin-6-ylthio or 3-(2-ethylhexyloxy)-1-oxidopyridazin-6-ylthio; or 2-oxo-1,2-dihydropyrimidinylthio optionally substituted by lower alkyl, amino, di-lower alkylamino 4-ylthio, 6-methyl-2-oxo-1,2-dihydropyrimidin-4-ylthio, 5-methyl-2-oxo-1,2-dihydropyrimidin-4-ylthio, 6-amino-2-oxo-1,2-dihydropyrimidin-4-ylthio, 6-dimethylamino-2-oxo-1,2-dihydropyrimidin-4-ylthio, 5-carboxy-2-oxo-1,2-dihydropyrimidin-4-ylthio or 6-carboxy-2-oxo-1,2-dihydropyrimidin-4-ylthio.

A protected carboxyl group of the formula —C(=O)—$R_2^A$ is especially an esterified carboxyl group in which $R_2^A$ represents a hydroxy group etherified by an organic radical or an organic silyl or stannyl group. Organic radicals, also as substituents in organic silyl or stannyl groups, are aliphatic, cycloaliphatic, cycloaliphatic-aliphatic, aromatic or araliphatic radicals, especially optionally substituted hydrocarbon radicals of this type, and heterocyclic or heterocyclic-aliphatic radicals, preferably having up to 18 carbon atoms.

An etherified hydroxy group $R_2^A$ forms together with the carbonyl grouping an esterified carboxyl group that can preferably be readily split, for example by reduction, such as by hydrogenolysis, or by solvolysis, such as acid hydrolysis or, especially, basic or neutral hydrolysis, oxidatively, or under physiological conditions, or an esterified carboxyl group that is readily convertible into another functionally modified carboxyl group, such as into another esterified carboxyl group or into a hydrazinocarbonyl group. Such a group $R_2^A$ is, for example, 2-halo-lower alkoxy, in which the halogen preferably has an atomic weight of more than 19, for example 2,2,2-trichloroethoxy or 2-iodoethoxy, also 2-chloroethoxy or 2-bromoethoxy which may readily be converted into the latter, or 2-lower alkylsulphonyl-lower alkoxy, for example, 2-methylsulphonylethoxy. The group $R_2^A$ is optionally substituted hydrocarbon radicals, especially saturated aliphatic or aromatic hydrocarbon radicals, such as lower alkyl, for example methyl, and/or phenyl, or is a methoxy group monosubstituted by an unsaturated aliphatic hydrocarbon radical, such as lower alkenyl, for example 1-lower alkenyl, such as vinyl, by a carbocyclic aryl group having electron-donating substituents, or by a heterocyclic group of aromatic nature having oxygen or sulphur as ring member. Examples of such groups $R_2^A$ are tert.-lower alkoxy, for example tert.-butoxy or tert.-pentoxy; optionally substituted diphenylmethoxy, for example diphenylmethoxy or 4,4'-dimethoxydiphenylmethoxy; lower alkenyloxy, especially 2-lower alkenyloxy, for example allyloxy; lower alkoxyphenyl-lower alkoxy, for example lower alkoxybenzyloxy, such as methoxybenzyloxy (in which methoxy is especially in the 3-, 4- and/or 5-position), especially 3- or 4-methoxybenzyloxy or 3,4-dimethoxybenzyloxy; or, above all, nitrobenzyloxy, for example, 4-nitrobenzyloxy, 2-nitrobenzyloxy or 4,5-dimethoxy-2-nitrobenzyloxy; or furfuryloxy, such as 2-furfuryloxy. The group $R_2^A$ is furthermore a 2-oxoethoxy group that is optionally substituted in the 2-position by lower alkyl, such as methyl, by lower alkoxy, such as methoxy or ethoxy, by aralkyl, such as benzyl, or by aryl, such as phenyl, and is substituted in the 1-position by lower alkyl, such as methyl, lower alkoxycarbonyl, such as methoxycarbonyl, lower alkylcarbonyl, such as methylcarbonyl, aralkylcarbonyl, such as benzylcarbonyl, or arylcarbonyl, such as benzoyl. Thus $R_2^A$ represents, for example, acetonyloxy, phenacyloxy, 2,4-dioxo-3-pentoxy, 1-methoxycarbonyl-2-oxopropoxy or 1-ethoxycarbonyl-2-oxopropoxy. The group $R_2^A$ is alternatively a 2-cyanoethoxy group that is optionally substituted in the 1- and/or in the 2-position, for example by lower alkyl, such as methyl, or by aryl, such as optionally substituted phenyl, and represents, for example, 2-cyanoethoxy or 2-cyano-2-phenylethoxy. $R_2^A$ is alternatively a 2-$(S_1)(S_2)(S_3)$-silylethoxy group, in which each of the substituents $S_1$, $S_2$ and $S_3$ independently of one another represents an optionally substituted hydrocarbon radical and the individual radicals may be linked by a single C—C bond A hydrocarbon radical $S_1$, $S_2$, $S_3$ is, for example, an alkyl radical, a cycloalkyl radical or an aryl radical, preferably such a radical having a maximum of 12 carbon atoms, wherein the radical of one kind may be substituted by a radical of a different kind, or by lower alkoxy, such as methoxy, or by halogen, such as fluorine or chlorine; and is especially lower alkyl having up to 7, preferably up to 4, carbon atoms, such as methyl, ethyl, propyl or butyl cycloalkyl having up to 7 carbon atoms, such as cyclopropyl or cyclohexyl; cycloalkylalkyl, such as cyclopentylmethyl; aryl having up to 10 carbon atoms, such as phenyl, tolyl or xylyl; or aryl-lower alkyl, such as benzyl or phenylethyl. Radicals $R_2^A$ of this kind to be given special mention are 2-tri-lower alkylsilylethoxy, such as 2-trimethylsilylethoxy or 2-(dibutylmethylsilyl)-ethoxy, and 2-triarylsilylethoxy, such as 2-triphenylsilylethoxy.

$R_2^A$ may alternatively be 2-oxa- or 2-thia-cycloalkoxy or -cycloalkenyloxy having 5–7 ring members, such as 2-tetrahydrofuryloxy, 2-tetrahydropyranyloxy or 2,3-dihydro-2-pyranyloxy or a corresponding thia group, or $R_2^A$ forms together with the —C(=O)— grouping an activated ester group and is, for example, nitrophenoxy, for example 4-nitrophenoxy or 2,4-dinitrophenoxy, or polyhalo-phenoxy, for example pentachlorophenoxy. $R_2^A$ may, however, alternatively be lower alkoxy, for example methoxy or ethoxy.

An organic silyloxy or organic stannyloxy group $R_2^A$ is especially a silyloxy or stannyloxy group substituted by 1 to 3 optionally substituted hydrocarbon radicals, preferably having up to 18 carbon atoms. It contains as substituents preferably optionally substituted, for example by lower alkoxy, such as methoxy, or by halogen, such as chlorine, aliphatic, cycloaliphatic, aromatic or araliphatic hydrocarbon radicals, such as lower alkyl, halo-lower alkyl, cycloalkyl, phenyl or phenyl-lower alkyl and represents especially tri-lower alkylsilyloxy, for example, trimethylsilyloxy, halo-lower alkoxy-lower alkylsilyloxy, for example, chloromethoxymethylsilyloxy; or tri-lower alkylstannyloxy, for example tri-n-butylstannyloxy.

The group $R_2^A$ may alternatively be an etherified hydroxy group that together with the carbonyl grouping —C(=O)— forms an esterified carboxyl group that can be split under physiological conditions.

These ester groups impart to the inherently active carboxylic acids improved absorption for oral administration and/or prolonged activity. Numerous such ester groups are known in the field of penicillins and cephalosporins. There may be mentioned, for example, —C(=O)—$R_2^A$ groups in which $R_2^A$ represents a methoxy group substituted by acyl, acyloxy, acylthio, acylamino or etherified hydroxy and optionally a further organic radical, in which the methyl group may be bonded to the carbonyl of the acyl group also by means of a bridge containing carbon, or represents a 2-amino-aliphatyloxy group. In such groups acyl represents the radical of an organic carboxylic acid having up to approximately 18 carbon atoms, and is, for example, optionally substituted alkanoyl, cycloalkanoyl, aroyl, heterocyclylcarbonyl; for example also the heterocyclylcarbonyl radical of a carboxylic acid of the formula I, or of a biologically active penam-3- or cephem-4-carboxylic acid, or is the acyl radical of a semi-seter of carbonic acid. Etherified hydroxy in the methoxy group is etherified by a hydrocarbon radical, especially by lower alkyl. The organic radical that optionally additionally substitutes the methoxy group has up to 7 carbon atoms and is especially lower alkyl, such as methyl, or aryl, such as phenyl. The said carbon bridge contains one to three, especially two, carbon atoms, so that a lactone, especially a γ-lactone, is present. The aliphatyl group in the said 2-aminoaliphatyl group may be of aliphatic or cycloaliphatic nature and is saturated or unsaturated. The 2-amino group is preferably substituted by alkylene containing two lower alkyl groups or optionally an oxa group. In such ester groups —C(=O)—$R_2^A$ that can be split physiologically, $R_2^A$ is, for example, lower alkanoyloxymethoxy, for example acetoxymethoxy or pivaloyloxymethoxy; amino-lower alkanoyloxymethoxy, especially α-amino-lower alkanoyloxymethoxy, for example glycyloxymethoxy, L-valyloxymethoxy, L-leucyloxymethoxy; lower alkoxycarbonyloxymethoxy or 1-lower alkoxycarbonyloxyethoxy, for example 1-ethoxycarbonyloxyethoxy; lower alkanoylthiomethoxy, for example acetylthiomethoxy or pivaloylthiomethoxy; lower alkanoylaminomethoxy, in which lower alkanoyl may optionally be substituted by halogen, such as chlorine, for example acetylaminomethoxy or 2,2-dichloroacetylaninomethoxy; aroylaminomethoxy, for example benzoylaminomethoxy; or, as an example of $R_2^A$ containing lactone, phthalidyloxy. The etherified hydroxymethoxy group $R_2^A$ is, for example, lower alkoxymethoxy, especially methoxymethoxy. A 2-aminoaliphatyloxy group $R_2^A$ is, for example, a 2-amino-lower alkoxy group, such as a 2-aminoethoxy group, in which amino is substituted by two lower alkyl groups or by alkylene optionally containing an oxa group, and represents, for example, 2-dimethylaminoethoxy, 2-diethylaminoethoxy or 2-(1-morpholino)ethoxy, or 2-aminocycloalkyloxy, for example 2-dimethylaminocyclohexyloxy.

A radical $R_2^A$ forming with a —C(=O)— grouping an optionally substituted hydrazinocarbonyl group is, for example, hydrazino or 2-lower alkylhydrazino, for example 2-methylhydrazino.

Preferred groups $R_2^A$ are those that can be converted into a free hydroxy group under neutral, basic or physiological conditions.

Salts are especially those of compounds of the formula I with an acid grouping such as a carboxyl group, or alternatively a hydroxysulphonyloxy group or sulpho group, especially metal or ammonium salts, such as alkali metal and alkaline earth metal salts, for example sodium, potassium, magnesium or calcium salts; as well as ammonium salts with ammonia or suitable organic amines, especially aliphatic, cycloaliphatic, cycloaliphatic-aliphatic or araliphatic primary, secondary or tertiary mono-, di- or polyamines, or heterocyclic bases being suitable for the salt formation, such as lower alkylamines, for example triethylamine; hydroxy-lower alkylamines, for example 2-hydroxyethylamine, di-(2-hydroxyethyl)amine or tri-(2-hydroxyethyl)-amine; basic aliphatic esters of carboxylic acids, for example 4-aminobenzoic acid 2-diethylaminoethyl ester; lower alkyleneamines, for example 1-ethylpiperidine; cycloalkylamines, for example bicyclohexylamine; or benzylamines, for example N,N'-dibenzylethylenediamine; and also, bases of the pyridine type, for example pyridine, collidine or quinoline. Compounds of the formula I that have a basic group may likewise form acid addition salts, for example with inorganic acids, such as hydrochloric acid, sulphuric acid or phosphoric acid, or with suitable organic carboxylic or sulphonic acids, for example trifluoroacetic acid or p-toluenesulphonic acid. Compounds of the formula I having an acid and a basic group may also occur in the form of inner salts, that is in the zwitterion form. Pharmaceutically acceptable salts are preferred.

In the penem compounds of the formula I the two asymmetric carbon atoms in the 5- and 6-positioned may occur in the R-, the S- or the racemic R,S-configuration. Preferred are the compounds in which the configuration of the 5-carbon atom corresponds to that of natural penicillin (5R-configuration). The substituents in the 5- and 6-positions may be in the cis- or trans-position in relation to one another.

The compounds of the present invention have valuable pharmacological properties or may be used as intermediate for the manufacture of compounds having such properties. Compounds of the formula I in which $R_a$ and $R_1$ have the meanings given above and $R_2$ represents hydroxy or an etherified hydroxy group $R_2^4$ forming together with the carbonyl group an esterified carboxyl group that can be readily split preferably under physiological conditions, or pharmacologically acceptable salts of such compounds having salt-forming groups have anti-bacterial activities. They inhibit, for example, the growth, of gram-positive and gram-negative bacteria, such as *Staphylococcus aureus* and penicillin-resistant *Staphylococcus aureus*, *Escherichia coli*, *Proteus vulgaris*, *Pseudomonas aeruginosa* and *Pseudomonas aeruginosa* R. Using the compounds of the formula I according to the invention in the disc-plate test with the specific bacteria with a 0.5% strength solution on filter paper (6 mm diameter) inhibiting zones of approximately 12 to 33 mm diameter are found.

Penicillin V tested analogously at the same time, in the case of penicillin-sensitive *Staphylococcus aureus* bacteria causes inhibiting zones of 29 to 33 mm diameter and in the case of penicillin-resistant bacteria inhibiting zones of a maximum of 9 to 12 mm. Neither Penicillin V nor Penicillin G is effective against *Pseudomonas aeruginosa*.

The anti-bacterial activity in vitro may also be ascertained in the Agar Dilution Test (according to Ericsson) in which against gram-positive and gram-negative cocci MIC values of 0.06 to 8 mcg/ml are ascertained and against gram-negative bacilli, such as entero bacteria, Pseudomonas and Haemophilus, MIC values of from 2 to 128 mcg/ml are ascertained In vivo, in the systemic infection of mice with *Streptococcus pyoqenes Aronson*, on subcutaneous administration of the compounds according to the invention ED$_{50}$ values of approximately $\leq 1$ to approximately 50 mg/kg result.

Attention is drawn in particular to the activity against *Pseudomonas aeruginosa*.

The compounds inhibit β-lactamases and have a synergistic effect in combination with other β-lactam antibiotics.

These new compounds, especially the preferred ones, or their pharmacologically acceptable salts, may therefore be used, alone or in combination with other antimicrobica, for example, in the form of antibiotically-active preparations, in the treatment of corresponding systemic or organ infections, as fodder additives, for preserving foodstuffs or as disinfectants.

Compounds of the formula I, in which $R_a$ and $R_1$ have the meanings given above, in which functional groups optionally present may be protected, and in which $R_2$ represents a radical $R_2^4$ forming together with the —C(=O)— grouping a protected carboxyl group that can preferably be readily split, wherein a carboxyl group protected in this manner is different from a carboxyl group that can be split physiologically, are valuable intermediates that can be converted in a simple manner, for example as described below, into the above-mentioned, pharmacologically active compounds.

The invention relates especially to the 2-penem compounds of the formula I, in which $R_a$ represents lower alkyl, hydroxy-lower alkyl, especially 1-hydroxy-lower alkyl, lower alkoxy-lower alkyl, lower alkanoyloxy-lower alkyl, hydroxysulphonyloxy-lower alkyl in salt form, especially 1-hydroxysulphonyloxy-lower alkyl, hydroxy, lower alkoxy, lower alkanoyloxy or lower alkanoyloxy substituted by phenoxy, hydroxy, halogen, amino or cyano, or phenyl-lower alkanoyloxy or phenyl-lower alkanoyloxy substituted by hydroxy or amino; $R_1$ represents hydrogen, lower alkyl, hydroxy-lower alkyl, lower alkoxy-lower alkyl, lower alkanoyloxy-lower alkyl, lower alkylthio-lower alkyl, heterocyclylthio-lower alkyl, amino-lower alkyl, acylamino-lower alkyl, carboxy-lower alkyl, lower alkoxycarbonyl-lower alkyl, phenyl-lower alkyl, phenyl: phenyl substituted by lower alkyl, lower alkoxy, hydroxy, halogen, nitro or by amino; furyl, thienyl, pyridyl; lower alkenylthio or lower alkylthio optionally substituted by hydroxy, lower alkoxy, lower alkanoyloxy, lower alkylthio, lower alkoxycarbonyl, carbamoyl, cyano, nitro, amino or by amino mono-substituted or di-substituted by lower alkyl or lower alkanoyl; or triazolylthio, tetrazolylthio, thiazolylthio, thiatriazolylthio, thiadiazolylthio, oxazolylthio or oxadiazolylthio, in which the heterocyclic rings may optionally be substituted, for example by lower alkyl, N,N-di-lower alkylamino-lower alkyl, carboxy-lower alkyl, sulpho-lower alkyl, amino, carboxy-lower alkanoylamino or by carbamoyl; and $R_2$ represents hydroxy, a hydroxy group etherified by an easily, especially physiologically, splittable organic radical or an organic silyl or stannyl group, or an optionally substituted hydrazino group $R_2^4$, and relates to salts of such compounds with salt-forming groups.

In a 2-penem compound of the formula I or in a salt of such a compound having salt-forming groups, $R_a$ especially represents lower alkyl having up to 4 carbon atoms, for example methyl, ethyl, propyl or butyl; hydroxy-lower alkyl especially 1-hydroxylower alkyl, having up to 4 carbon atoms, for example hydroxymethyl, hydroxyethyl or hydroxypropyl; lower alkoxy-lower alkyl, especially 1-lower alkoxy-lower alkyl, in which lower alkyl contains up to 4 carbon atoms, for example 1-methoxymethyl, 1-methoxyethyl or methoxypropyl; lower alkanoyloxy-lower alkyl, especially 1-lower alkanoyloxy-lower alkyl, in which lower alkanoyloxy and lower alkyl each contain up to 4 carbon atoms, for example acetoxymethyl, propionoxymethyl or 1-acetoxyethyl; hydroxysulphonyloxy-lower alkyl in salt form, in which lower alkyl contains up to 4 carbon atoms, especially 1-hydroxysulphonyloxy-lower alkyl, for example hydroxysulphonyloxymethyl, 1-hydroxysulphonyloxyethyl or 1-hydroxysulphonyloxypropyl; hydroxy; lower alkoxy containing up to 4 carbon atoms, for example methoxy, ethoxy, propoxy or butoxy; lower alkanoyloxy having up to 4 carbon atoms, for example formyloxy, acetoxy or propionoxy, or such a lower alkanoyloxy substituted by phenoxy, hydroxy, halogen, amino or cyano, for example phenoxyacetoxy, hydroxyacetoxy, haloacetoxy, aminoacetoxy or cyanoacetoxy; phenyl-lower alkanoyloxy, in which lower alkanoyloxy contains up to 4 carbon atoms, for example phenylacetoxy, or phenyl-lower alkanoyloxy substituted by hydroxy or amino, in which lower alkanoyl contains up to 4 carbon atoms, for example hydroxyphenylacetoxy or aminophenylacetoxy, in which hydroxy or amino is preferably in the p-position, or α-hydroxyphenylacetoxy or α-aminophenylacetoxy; $R_1$ especially represents hydrogen; lower alkyl having up to 4 carbon atoms, for example methyl, ethyl, propyl or butyl; hydroxy-lower alkyl, especially ω-hydroxy-lower alkyl, having up to 4 carbon atoms, for example hydroxymethyl, hydroxyethyl or hydroxypropyl; lower alkoxy-lower alkyl, especially ω-lower alkoxy-lower alkyl, in which lower alkoxy and lower alkyl contain up to 4 carbon atoms, for example methoxymethyl, methoxyethyl or methoxypropyl; lower alkanoyloxy-lower alkyl, especially ω-lower alkanoyloxy-lower alkyl, in which lower alkanoyloxy and lower alkyl each contain up to 4 carbon atoms, for example acetoxymethyl, acetoxyethyl or acetoxypropyl; lower alkylthio-lower alkyl, especially ω-lower alkylthio-lower alkyl, in which lower alkyl contains up to 4 carbon atoms, for example methylthiomethyl, tert.-butylthiomethyl, methylthioethyl or methylthiopropyl; heterocyclylthio-lower alkyl, in which lower alkyl contains up to 4 carbon atoms and heterocyclyl represents a five-membered aromatic diaza-, thiaza-, tetraza-, thiaza-, thiadiaza-, thiatriaza-, oxaza- or oxadiaza-cyclic radical optionally substituted by lower alkyl, such as methyl, carboxy-lower alkyl, for example carboxymethyl or 1- or 2-carboxyethyl, optionally N-substituted amino-lower alkyl, such as di-lower-alkylamino-lower alkyl, for example dimethylaminoethyl, sulpho-lower alkyl in salt form, for example sulphomethyl or 1- or 2-sulphoethyl in the form of a sodium salt, for example imidazol-2-ylthiomethyl, 1,2,3-triazol-4-ylthiomethyl, 1-methyl-1H-1,2,3-triazol-4-ylthiomethyl, 1H-tetrazol-5-ylthiomethyl, 1-methyl-1H-tetrazol-5-ylthiomethyl, 1-carboxymethyl-1H-tetrazol-5-ylthiomethyl, 1-(2-dimethylaminoethyl)-1H-tetrazol-5-ylthiomethyl, 1-sodium sulphomethyl-1H-tetrazol-5-ylthiomethyl or 2-methyl-1,3,4-thiadiazol-5-ylthiomethyl or an ethyl radical correspondingly substituted in the 2-position; amino-lower alkyl, especially ω-amino-lower alkyl in which lower alkyl contains up to 4 carbon atoms, for example aminomethyl, aminoethyl or aminopropyl; acylamino-lower alkyl, in which acyl is lower alkanoyl or a substituted oxycarbonyl group that can be used as an amino-protective group, for example acetylaminomethyl, acetylaminoethyl, acetylaminopropyl or tert.-butyl-, 2,2,2-trichloroethyl-, diphenylmethyl- or p-nitrobenzyloxycarbonylaninomethyl, -ethyl or -propyl; carboxy-lower alkyl, in which lower alkyl contains up to 4 carbon atoms and carboxy is especially carbonyl-lower alkyl each contain up to 4 carbon atoms, for example, methoxy-, ethoxy- or tert.-butoxycarbonylmethyl or -ethyl; or phenyl-lower alkyl, in which lower alkyl contains up to 4 carbon atoms, for example benzyl, phenylethyl or phenylpropyl; phenyl; hydroxyphenyl; aminophenyl; furyl, thienyl or pyridyl, such as fur-2-yl; thien-2-yl, pyrid-2-yl; pyrid-3-yl; pyrid-4-yl; lower alkylthio, for example methyl-, ethyl- or propylthio, lower alkenylthio, for example vinylthio or allylthio, or lower alkylthio or lower alkenylthio substituted, especially in the Ω-position, by amino, mono- or di-lower alkylamino or lower alkanoyl amino, for example 2-aminoethylthio, 2-methylaminoethylthio, 2-dimethylaminoethylthio, 2-acetylaminoethylthio, 3-aminopropylthio, 3-methylaminopropylthio, 3-dimethylaminopropylthio or 3-acetylaminopropylthio, 2-acetylaminoethylthio; tetrazolylthio or thiadiazolthio optionally substituted by lower alkyl, sulfo-lower alkyl, carboxy-lower alkyl, or by di-lower alkylamino-lower alkyl, especially 1-methyl-1H-tetrazol-5-ylthio, 1-sulphomethyl-1H-tetrazol-5-ylthio, 1-carboxymethyl-1H-tetrazol-5-ylthio, 1-(2dimethylaminoethyl)-1H-tetrazol-5-ylthio; 2-methyl-1,3,4-thiadiazol-5-ylthio or 1,3,4-thiadiazol-1-ylthio; and $R_2$ especially represents hydroxy, optionally α-polybranched lower alkoxy, for example, methoxy or tert.-butoxy; or 2-halo-lower alkoxy, for example 2,2,2-trichloroethoxy, 2-iodoethoxy, or 2-chloroethoxy or 2-bromoethoxy readily convertible into the 2-iodoethoxy; or phenacyloxy; 1-phenyl-lower alkoxy having 1-3 phenyl radicals optionally substituted by lower alkoxy and/or nitro, for example 4-methoxybenzyloxy, 4-nitrobenzyloxy, 2-nitro-4,5-dimethoxybenzyloxy, diphenylmethoxy, 4,4'-dimethoxydiphenylmethoxy or trityloxy; acetonyloxy; 2-cyanoethoxy; 2-tri-lower alkylsilylethoxy, for example 2-trimethylsilylethoxy; lower alkancyloxymethoxy, for example acetoxymethoxy or pivaloyloxymethoxy; αamino-lower alkanoyloxymethoxy, for example glycyloxymethoxy, phthalidyloxy, pentachlorophenoxy; also tri-lower alkylsilyloxy, for example trimethylsilyloxy; and lower alkenyloxy, such as 2-lower alkenyloxy, for example allyloxy.

The invention relates especially to 2-$R_1$—6-$R_2$—2-penem-3-carboxylic acid compounds in which $R_a$ represents lower alkyl having up to 4 carbon atom, especially methyl, ethyl, propyl, isopropyl, or butyl; 1-hydroxy-lower alkyl having up to 4 carbon atom, especially hydroxymethyl, 1-hydroxmethyl; 1-hydroxypropyl or 1-hydroxyisopropyl; phenyl-lower alkyl having up to 10 carbon atoms, especially benzyl; phenoxy-lower alkanoyloxy having up to 10 carbon atoms, especially phenoxyacetoxy; or lower alkoxy having up to 4 carbon atoms, especially methoxy;

and $R_1$ represents hydrogen; lower alkyl having up to 4 carbon atoms, especially methyl: amino- lower alkyl, especially ω-amino-lower alkyl, in which lower alkyl contains up to 4 carbon atoms, for example aminomethyl, aminoethyl or aminopropyl; acylamino-lower alkyl, in which acyl is lower alkanoyl or a substituted oxycarbonyl group that can be used as an amino-protective group, for example acetylaminomethyl acetylaminoethyl, acetylaminopropyl or tert.-butyl-, 2,2,2-trichloroethyl-, diphenylmethyl- or p-nitrobenzyloxycarbonylaminomethyl, -ethyl or -propyl; lower alkylthio, especially ethylthio; lower alkylthio or lower alkenylthio substituted, especially in the Ω-position, by amino, mono- or di-lower alkylamino or lower alkanoylamino, for example 2-aminoethylthio, 2-methylaminoethylthio, 2-dimathylaminoethylthio, 2-acetylaminoethylthio, 3-aminopropylthio, 3-methylamincpropylthio, 3-dinethylaminopropylthio or 3-acetylaninopropylthio, 2-acetylaninovinylthio, 1-methyl-1H-tetrazol-5-ylthio, 1-(2-dimethylaminoethyl)-1H-tetrazol-5-ylthio, 2-methyl-1,3,4-thiadiazol-5-ylthio or 1,3,4-thiadiazol-2-ylthio; and to the esters, especially the esters that can be split under neutral or basic conditions, such as nitrobenzyl esters, for example 4-nitrobenzyl, diphenylmethyl, pentachlorophenyl, acetonyl, 2-cyanoethyl or 2-trimethylsilylethyl ester, and to esters of such compounds that can be split under physiological conditions, and to the salts, especially the pharmacologically acceptable salts, of such compounds having salt-forming groups, The invention relates especially to the compounds of the formula I mentioned in the Examples, to the salts thereof, especially the -pharmaceutically acceptable salts, and to the new starting materials and intermediates that can be used for their manufacture.

On account of its particularly good antibacterial activity, 6-ethyl-2-(3-aminopropyl)-2-penem 3-carboxylic acid, especially the corresponding 5R-compound, and the pharmacologically acceptable salts and physiologically split-table esters are to be given special attention.

The new compounds are produced by ring closing an ylid compound of the formula

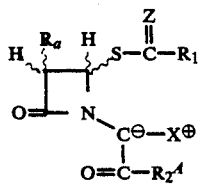

(II)

in which $R_a$, $R_1$ and $R_2^A$ have the meanings given, wherein the functional groups in these radicals are preferably present in protected form, Z represents oxygen or sulphur, and in which $X^\oplus$ represents either a phosphonio group substituted three times or a phosphono group esterified twice, together with a cation and, if desired or necessary, converting the protected carboxyl group of the formula —C(=O)—$R_2^A$ in a compound of the formula I obtained into the free or into a different protected carboxyl group, and/or, if desired, in a compound of the formula I obtained, converting a group $R_a$ and/or $R_1$ within the definition into a different group $R_a$ and/or $R_1$, and/or, if desired, converting a compound obtained having a salt-forming group into a salt, or a salt obtained into the free compound or into a different salt, and/or, if desired, separating a mixture of isomeric compounds obtained into the individual isomers.

In the starting material of the formula II $R_a$, $R_1$ and $R_2^A$ have especially the preferred meanings, wherein functional groups are usually present in the protected form, amino, for example, is present in the form of the nitro or azido group.

In a starting material of the formula II, $R_2^A$ preferably represents an etherified hydroxy group forming together with the —C(=O)—grouping an esterified carboxyl group that can readily be split, especially under mild conditions, wherein functional groups that are optionally present in a carboxyl protective group $R_2^A$ may be protected in a manner known per se, for example as indicated above. A group $R_2^A$ is inter alia lower alkoxy, especially α-polybranched lower alkoxy, for example methoxy or tert.-butoxy; lower alkenyloxy, especially 2-lower alkenyloxy, for example allyloxy; or 2-halo-lower alkoxy, for example 2,2,2-trichloroethoxy, 2-bromoethoxy, or 2-iodoethoxy; 2-lower alkylsulphonyllower alkoxy, for example 2-methylsulphonylethoxy; or an optionally substituted, such as lower alkoxy, for example methoxy-, or nitro-containing, 1-phenyl-lower alkoxy group, such as diphenylmethoxy or benzyloxy optionally substituted, for example as mentioned, for example benzyloxy, 4-methoxybenzyloxy,4-nitrobenzyloxy, diphenylmethoxy or 4,4'-dimethoxydiphenylmethoxy: pentachlorophenoxy; acetonyloxy; 2-cyanoethoxy; a 2-($S_1$)($S_2$)($S_3$)-silylethoxy group, such as 2-trimethylsilylethoxy, 2-(dibutylmethylsilyl)-ethoxy or 2-triphenylsilylethoxy; also an organic silyloxy or stannyloxy group, such as tri-lower alkylsilyloxy, for example trimethylsilyloxy; or one of the mentioned etherified hydroxy groups that can be split physiologically.

The group $X^\oplus$ in the starting material of the formula II is one of the phosphonio or phosphono groups customary in the Wittig condensation reaction, especially a triaryl-, for example triphenyl-, or trilower alkyl-, for example tributylphosphonio group, or a phosphono group esterified twice by lower alkyl, for example ethyl, wherein the symbol $X^\oplus$ in the case of the phosphono group additionally includes the cation of a strong base, especially a suitable metal, for example a lithium sodium or potassium, ion. Preferred as group $X^\oplus$ is in one case triphenylphosphonio and in the other case diethylphosphono together with an alkali metal ion, for example a sodium ion.

In phosphonio compounds of the formula II, which in the isomeric ylene form are alternatively called phosphorane compounds, the negative charge is neutralised by the positively charged phosphonio group. In phosphono compounds of the formula II, which in their isomeric form can alternatively be called phosphonate compounds, the negative charge is neutralised by the cation of a strong base, which cation, depending on the method of production of the phosphono starting material, may be, for example, an alkali metal ion, for example, a sodium, lithium or potassium ion. The phosphonate starting substances are therefore used as salts in the reaction.

Formula II shows the starting material in the form in which the ring closure takes place. Normally the corresponding phosphoranylidene compound of the formula

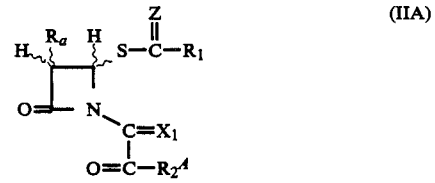

(IIA)

in which $X_1$ represents a tri-substituted, especially a triaryl-, for example triphenyl-, or a tri-lower alkyl-, for example tri-n-butyl-phosphoranylidene radical, or the corresponding phosphono compound of the formula

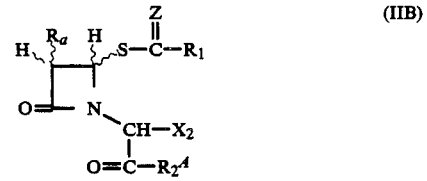

(IIB)

which $X_2$ represents a phosphono-, especially a dialkylphosphono-, for example a diethylphosphono group, is used, wherein a phosphono starting material of the formula IIB is converted into the form suitable for the ring closure that is into the compound of the formula II, by treating with a suitable basic reagent, such as an inorganic base, for example an alkali metal carbonate, such as sodium or potassium carbonate, or with an organic base, such as a tri-lower alkylamine, for example triethylamine, or a cyclic base of the amidine type, such as an appropriate diaza-bicycloalkene compound, for example 1,5-diaza-bicyclo[5,4,0]undec-5-ene.

Preferred starting materials are the phosphoranylidene compounds of the formula IIA.

The ring closure can take place spontaneously, that is to say during the production of the starting materials, or by heating, for example in a temperature range of approximately 30° C. to approximately 160° C., preferably of approximately 50° C. and approximately 100° C.

The reaction is preferably carried out in the presence of a suitable inert solvent, such as in an aliphatic, cycloaliphatic or aromatic hydrocarbon, for example hexane, cyclohexane, benzene, toluene, xylene or mesitylene; a halogenated hydrocarbon, for example methylene chloride; an ether, for example diethyl ether; a lower alkylene glycol di-lower alkyl ether, for example dimethoxyethane or diethylene glycol dimethyl ether, or a cyclic ether, for example dioxan or tetrahydrofuran; a carboxylic acid amide, for example dimethylformamide; a di-lower alkyl sulphoxide, for example dimethylsulphoxide; or a lower alkanol, for example methanol, ethanol or tert.-butanol; or in a mixture thereof, and, if necessary, in an inert gas atmosphere, for example an argon or nitrogen atmosphere.

In a compound of the formula I obtainable according to the invention having a protected, especially an esterified, carboxyl group of the formula —C(=O)—$R_2^4$, the latter can be converted in a manner known per se, for example depending on the type of protective group, into the free carboxyl group. For example, a carboxyl group esterified by a suitable 2-halo-lower alkyl group, an arylcarbonylmethyl group or a 4-nitrobenzyl group can be converted into the free carboxyl group for example by treating with a chemical reducing agent, such as a metal, for example zinc, or a reducing metal salt, such as a chromium(II) salt, for example chromium(II) chloride, usually in the presence of a hydrogen-yielding agent, which together with the metal enables nascent hydrogen to be produced, such as an acid, especially acetic or formic acid, or an alcohol, wherein water is preferably added; a carboxyl group esterified by an arylcarbonylmethyl group can be converted into the free carboxyl group by treating with a nucleophilic, preferably salt-forming reagent, such as sodium thiophenolate or sodium iodide; and also a carboxyl group esterified by 4-nitrobenzyl can be converted into the free carboxyl group by treating with an alkali metal dithionite, for example sodium dithionite. A carboxyl group esterified by a 2-lower alkylsulphonyl-lower alkyl group can be split and released, for example by treating with a basic agent, for example one of the nucleophilic-reacting bases mentioned further below; a carboxyl group esterified by a suitable arylmethyl grouping can be split and released, for example by radiation, preferably with ultra-violet light, for example of less than 290 mμ when the arylmethyl group is, for example, a benzyl radical optionally substituted in the 3-, 4- and/or 5-position, for example by lower alkoxy and/or nitro groups, or with longer-wave ultraviolet light, for example of above 290 mμ, when the arylmethyl group is, for example, a benzyl radical substituted in the 2-position by a nitro group; a carboxyl group esterified by a suitably substituted methyl group, such as tert.-butyl or di-phenylmethyl, can be split and released, for example, by treating with a suitable acid agent, such as formic acid or trifluoroacetic acid, optionally with the addition of a nucleophilic compound, such as phenol or anisole; and an esterified carboxyl group that can be split by hydrogenolysis, for example benzyloxycarbonyl or 4-nitrobenzyloxycarbonyl, can be split and released by hydrogenolysis, for example by treating with hydrogen in the presence of a noblemetal, for example a palladium, catalyst. In addition, a carboxyl group esterified with a lower alkenyl group, such as with 2-lower alkenyl, especially allyl, can be converted oxidatively, for example by treating with ozone, followed by a reducing agent, for example dimethyl sulphide, into a formylmethoxycarbonyl group, from which the carboxyl group can be released by treating with a base, such as a secondary amine, for example dimethylamine; or a 2-lower alkenyloxycarbonyl group, for example allyloxycarbonyl, can be isomerised, for example by treating with tristriphenylohosphine rhodium chloride, palladium-on-carbon, or an alkali metal-lower alkanolate, for example potassium tert.-butylate, in dimethyl sulphoxide to form a 1-lower alkenyloxycarbonyl group and this can be split hydrolytically under weakly acidic or weakly basic conditions. A 2-oxoethoxycarbonyl or 2-cyanoethoxycarbonyl group optionally substituted in the 2-position by lower alkyl or by aryl, for example the acetonyloxycarbonyl or 2-cyanoethoxycarbonyl group, can be converted under mild conditions, that is at room temperature or while cooling, by treatment with a suitable base, into the corresponding salt of this carboxyl group, from which the free carboxyl group can be obtained by acidification. Suitable bases are nucleophilic-reacting metal, such as alkaline earth metal, and especially alkali metal, bases, such as corresponding hydroxides, carbonates, bicarbonates, alkoxides, phenolates, mercaptides, thiophenolates or amides, for example sodium hydroxide, sodium carbonate, sodium bicarbonate, sodium ethanolate, sodium thiophenolate, sodium amide or sodium morpholide, or corresponding lithium or potassium compounds, which are used in water or in aqueous or hydroxyl group-containing or alternatively polar inert solvents with subsequent treatment with water. To split the 2-cyanoethoxycarbonyl groups, it is also possible to use tertiary amines, such as tri-lower alkylamine, for example triethylamine or Hünig base, or cyclic or bicyclic amines or imines such as N-methylmorpholine or 1,5-diazabicyclo[5,4,0]undec-5-ene, in an inert solvent, such as methylene chloride or tetrahydrofuran, wherein the corresponding ammonium salts of the carboxyl compound are obtained directly A substituted silylet hoxycarbonyl group can be converted into the free carboxyl group by treatment with a salt of hydrofluoric acid that yields fluoride anions, such as an alkali metal fluoride, for example sodium or potassium fluoride, in the presence of a macrocyclic polyether ("crown ether"), or with a fluoride of an organic quaternary base such as tetraalkylammonium fluoride or trialkylarylammonium fluoride, for example tetraethylammonium fluoride or tetrabutylammonium fluoride, in the presence of an aprotic polar solvent, such as dimethyl sulphoxide or N,N-dimethylacetamide. A pentachlorophenoxycarbonyl group can be converted into a free carboxyl group under mild conditions, for example by dilute sodium carbonate solution or sodium bicarbonate solution or by an organic base in the presence of water.

A carboxyl group protected, for example, by silylation or stannylation, can be released in the usual manner by solvolysis, for example by treating with water or an alcohol.

If there is more than one protected carbcxyl group present in a compound obtainable in accordance with the invention these may be converted into free carboxyl groups either jointly or selectively.

In a compound of the formula I obtainable in accordance with the process that contains a free carboxyl group, such a group can be converted in a manner known per se into a protected carboxyl group. For example, esters are obtained, for example, by treating with a suitable diazo compound, such as a diazo-lower alkane, for example diazomethane or diazobutane, or a phenyldiazo-lower alkane, for example diphenyldiazomethane, if necessary in the presence of a Lewis acid, such as, for example, boron trifluoride, or by reacting with an alcohol suitable for esterification in the presence of an esterifying agent, such as a carbodiimide, for example dicyclohexylcarbodiimide, or carbonyldiimidazole, or further with an N,N'-disbustituted O- or S-substituted isourea or isothiourea, in which an O- and S-substituent is, for example, lower alkyl, especially tert.-butyl, phenyl-lower alkyl or cycloalkyl, and N- or N'-substituents are, for example, lower alkyl, especially isopropyl, cycloalkyl or phenyl, or according to any other known and suitable method of esterification, such as reacting a salt, optionally produced in situ, of the acid with a reactive ester of an alcohol and a strong inorganic acid or strong organic sulphonic acid. Further, acid halides, such as acid chlorides (produced, for example, by treating with oxalyl chloride), activated esters (formed, for example, with N-hydroxy nitrogen compounds, such as N-hydroxysuccinimide) or mixed anhydrides (obtained, for example, with haloformic acid lower alkyl esters, such as chloroformic acid ethyl ester or chloroformic acid isobutyl ester, or with haloacetic acid halides, such as trichloroacetic acid chloride) can be converted into an esterified carboxyl group by reacting with alcohols, optionally in the presence of a base, such as pyridine.

In a compound of the formula I having an esterified carboxyl group, this group can be converted into a different esterified carboxyl group, for example 2-chloroethoxycarbonyl or 2-bromoethoxycarbonyl can be converted into 2-iodoethopxycarbonyl by treating with an iodine salt, such as sodium iodide, in the presence of a suitable solvent, such as acetone.

In a compound having a free carboxyl group obtainable according to the process, such a group can also be converted into an optionally substituted hydrazinocarbonyl group, by reacting preferably reactive functionally modified derivatives, such as the above-mentioned activated esters, or mixed anhydrides of the corresponding acid with hydrazines.

A carboxyl group protected by an organic silyl or stannyl group can be formed in a manner known per se, for example by treating the compound containing carboxyl or a salt thereof, such as an alkali metal salt, for example a sodium salt, thereof, with a suitable silylation or stannylation agent.

In the process according to the invention, and in additional steps to be carried out where applicable or where necessary, if required free functional groups that do not participate in the reaction are transiently protected in a manner known per se: for example, free amino groups are transiently protected, for example, by acylation, tritylation or silylation; free hydroxy and mercapto groups, for example by etherification or esterification, inclusive of silylation; and can, if desired, be released individually or jointly in a manner known per se after the reaction. For example amino, hydroxy, mercapto, carboxyl or sulpho groups present in a starting material may be protected, for example in the form of acylamino groups, such as those mentioned above, for example the 2,2,2-trichloroethoxycarbonylamino group, 2-bromoethoxycarbonylamino group, 4-methoxybenzyloxycarbonylamino group or tert.-butoxycarbonylamino group, or in the form of aryl- or aryl-lower alkylthioamino groups, for example the 2-nitro-phenylthioamino group or arylsulphonylamino group, for example the 4-methylphenylsulphonylamino group, in the form of 1-lower alkoxycarbonyl-2-propylideneamino groups or of the o-nitrophenoxyacetylamino groups, or of acyloxy groups, such as those mentioned above, for example the tert.-butoxycarbonyloxy group, 2,2,2trichloroethoxycarbonyloxy group, 2-bromoethoxycarbonyloxy group or p-hitrobenzyloxycarbonyloxy group, or corresponding acylthio groups, or in the form of esterified carboxy groups, such as those mentioned above, for example the tert.-butoxycarbonyloxy group, 2,2,2-trichloroethoxycarbonyl group, 2-bromoethoxycarbonyloxy group or p-nitrobenzyloxycarbonyloxy group, or corresponding acylthio groups, or in the form of esterified carboxy groups, such as those mentioned above, for example the diphenylmethoxycarbonyl group, p-nitrobenzyloxycarbonyl group, acetonyloxycarbonyl group or 2-cyanoethoxycarbonyl group, or of substituted sulpho groups, such as the above-mentioned lower alkylsulpho groups, for example the methylsulcho group, and when the reaction is complete may be released, where applicable after converting the protective group. For example, a 2,2,2-trichloroethoxycarbonylamino group or 2-iodoethoxycarbonylamino group or alternatively a p-nitrobenzyloxycarbonylamino group may be split by treating with suitable reducing agents, such as zinc in the presence of aqueous acetic acid or hydrogen in the presence of a palladium catalyst a diphenylmethoxycarbonylamino group or tert.-butylcarbonylamino group may be split by treating with formic acid or trifluoroacetic acid: an aryl- or aryl-lower alkylthioamino group may be split by treating with a nucleophilic reagent such as sulphurouse acid; an arylsulphonylamino group may be split by means of electrolytic reduction; a 1-lower alkoxycarbonyl-2-propylideneamino group by treating with aqueous mineral acid, and a tert.-butoxycarbonyloxy group by treating with formic or trifluoroacetic acid or a 2,2,2-trichloroethoxycarbonyloxy group or p-nitrobenzyloxycarbonyloxy group may be split by treating with a chemical reducing agent, such as zinc in the presence of aqueous acetic acid, or with hydrogen in the presence of a palladium catalyst; and a diphenylmethoxycarbonyl group may be split by treating with formic or trifluoroacetic acid or by hydrogenolysis: an acetonyloxy- or cyanoethoxycarbonyl group may be split by treating with bases, such as sodium bicarbonate or 1,5-diazabicyclo[5,4,0]undec-5-ene, and a substituted sulpho group by treating with an alkali metal halide; the splitting may, if desired, in each case be carried out in stages.

Furthermore, in a resulting compound functional substituents, such as free amino, hydroxy, mercapto, carboxy or sul-oho groups, may be functionally modified by processes known per se, for example by alkylation, acylation or esterification or substitution.

Thus, an amino, hydroxy, mercapto, carboxy or sulpho group may be alkylated, for example methylated, by treating with an alkylating reagent, such as a diazo compound, for example diazomethane, or with a reactive ester of an alcohol, for example dimethyl sulphate, or amino, hydroxy or mercapto groups may be acylated, for example, acetylated, by treating with a reactive functional derivative of an acid, for example an anhydride or acid chloride, such as acetic anhydride or acetyl chloride. Further, for example an amino group may be converted into a sulphoamino group by treating with sulphur trioxide, preferably in the form of a complex with an organic base such as a tri-lower alkylamine, for example triethylamine.

A hydroxy group in the substituent $R_a$, especially the hydroxy group in a 1-hydroxy-lower alkyl radical, may be converted into a hydroxysulphonyloxy group present in corresponding salt form by treating with a sulphur trioxide complex, for example the complex with dioxan or with a tertiary nitrogen base, such as tri-lower alkylamine, for example triethylamine, N,N-di-lower alkylaniline, for example, N,N dimethylaniline, or especially with pyridine, or alternatively by treating with the amidosulphonic acid, optionally in the presence of pyridine, and the hydroxysulphonyloxy group in salt form can be converted into a hydroxysulphonyloxy group present in metal salt form by double reaction with a corresponding metal hydroxide, metal carbonate, or metal bicarbonate, such as an alkali metal, for example sodium, hydroxide, carbonate or bicarbonate.

In compounds obtainable according to the invention, in a manner known per se, primary and secondary hydroxy groups may also be converted into aldehyde or keto groups by oxidation, for example according to Pfitzner-Moffatt, or, if necessary after acylation, may be split off together with an adjacent removable hydrogen atom to form a C—C double bond. Aldehyde or keto groups may be converted into hydroxy groups by reduction, for example with complex metal hydrides, or into acetals or ketals by treating with alcohols, into the corresponding imines, oximes or hydrazones by treating with an amine, hydroxylamine or hydrazine, or into the corresponding methylidene compounds by treating with a Wittig reagent. Resulting acetals or ketals may be converted into the corresponding aldehydes or ketones, for example by treating with trimethyliodosilane. In compounds obtained according to the invention, furthermore, in a manner known per se, C—C double bonds may be reduced, for example with catalytically activated hydrogen. Halogen, such as bromine or iodine, substituents may be replaced by hydrogen by treating, for example, with zinc/silver in methanol or methanol/acetic acid, or may be converted into 1-substituted 1-hydroxymethyl groups, for example the 1-hydroxyethyl group, by treating with an organometal compound, such as methyl magnesium bromide or butyl lithium, followed by an aldehyde, for example acetaldehyde. A nitro or azido group may be converted into an amino group, for example by treating with catalytically activated, for example by a palladium or platinum oxide catalyst, hydrogen. The mentioned subsequent reactions can be carried out both at the appropriate places in the radicals $R_a$ and in the radicals $R_1$.

Salts of compounds of the formula I may be produced in a manner known per se. For example, salts of such compounds with acid groups can be formed for example by treating with metal compounds such as alkali metal salts of suitable carboxylic acids, for example the sodium salt of α-ethylcaproic acid, or with ammonia or a suitable organic amine, wherein preferably stoichiometric amounts or only a small excess of the salt-forming agent is used. Salts of carboxylic acids of the formula I may also be obtained by splitting under basic conditions the mentioned esters of such compounds that can be split under such conditions, for example 2-cyanoethyl or acetonyl esters. Acid addition salts of compounds of the formula I with basic groupings are obtained in the usual manner, for example by treating with an acid or a suitable anion exchange reagent. Inner salts of compounds of the formula I that contain, for example, a salt-forming amino group and a free carboxyl group may be formed, for example, by neutralising salts such as acid addition salts to the isoelectric point, for example with weak bases, or by treating with liquid ion exchangers. Salts of 1-oxides of compounds of the formula I with salt-forming groups may be produced in an analogous manner.

Salts may be converted in the usual manner into the free compounds: metal and ammonium salts, for example, by treating with suitable acids, and acid addition salts, for example, by treating with a suitable basic agent.

Mixtures of isomers obtained may be separated into the individual isomers by methods known per se: mixtures of diastereoisomeric isomers, for example, by fractional crystallisation, adsorption chromatography (column or thin-layer chromatography) or other suitable separating processes. Resulting racemic compounds can be separated into the antipodes in the usual manner, optionally after introducing suitable salt-forming groupings, for example by forming a mixture of diastereoisomeric salts and converting the optically active salts into the free compounds, or by fractional crystallisation from optically active solvents.

In all subsequent conversions of the compounds obtained, the reactions that are preferred are those carried out under neutral, alkaline or weakly basic conditions.

The process also includes those embodiments according to which compounds produced as intermediates are used as starting substances and the remaining process steps are carried out with these, or according to which the process is interrupted at any stage; furthermore, starting substances may be used in the form of derivatives or may be formed in situ, optionally under the conditions of the reaction. For example, a starting material of the formula II in which Z is oxygen may be produced in situ from a compound of the formula II in which Z is an optionally substituted methylidene group, by ozonisation and subsequent reduction of the ozonide formed, analogously to the method given in stage 2.5, whereupon, especially when $R_1$ is hydrogen, the cyclisation to the compound of the formula I takes place in the reaction solution.

The starting compounds of the formula II and the preliminary stages may be produced, for example, according to the following reaction schemes 1, 2 and 3.

Reaction scheme 1

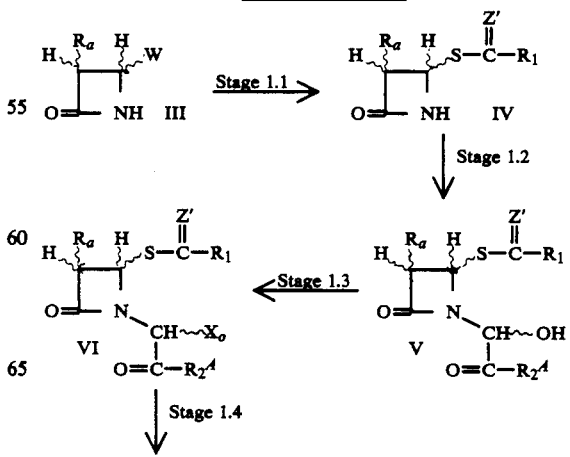

-continued
Reaction scheme 1

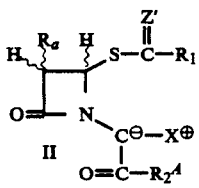

In the compounds of the formulae IV, V, VI and II in the reaction scheme I and in the compounds of the formulae Xa, XI, XII and IVa in the reaction scheme 2, Z' is oxygen, sulphur or alternatively, especially when $R_1$ is hydrogen, a methylidene group optionally substituted by ono or two substituents Y, which group can be converted by oxidation into an oxo group Z. A substituent Y of this methylidene group is an organic radical, for example one of the organic radicals mentioned under $R_1$, such as one of the mentioned, optionally substituted, lower alkyl, cycloalkyl, cycloalkyl-lower alkyl, phenyl or phenyl-lower alkyl radicals, and especially one of the functionally modified, such as esterified, carboxyl groups. Esterification with an optically active alcohol such as l-menthol is included. This methylidene group preferably carries one of the substituents mentioned. The methoxycarbonylmethylidene and the (1)-menthyloxycarbonylmethylidene group Z' are given special mention. The latter can be used for the production of optically active compounds of the formulae IV to VI and II.

Stage 1.1

A thioazetidinone of the formula IV is obtained by treating a 4-W-azetidinone of the formula III, in which W represents a nucleofuge leaving group with a mercapto compound $R_1-C(=Z')-SH$ or with a salt, for example an alkali metal salt such as a sodium or potassium salt thereof, and, if desired, separating an isomeric mixture obtained into the individual isomers, and/or if desired converting a group $R_a$ or $R_1$ in a compound obtained into a different group $R_a$ or L $R_1$ respectively, and/or, if desired, converting an optionally substituted methylidene group Z' into an oxo group Z.

The nucleofuge leaving group W in a starting material of the formula III is a radical that can be replaced by the nucleophilic radical $R_1-C(=Z')-S-$. Such groups W are, for example, acyloxy radicals, sulphonyl radicals $R_\sigma-SO_2-$, in which $R_o$ is an organic radical, azido or halogen. In an acyloxy radical W, acyl is the radical or an organic carboxylic acid, including an optically active carboxylic acid, and has, for example, the same meaning as the acyl radical $R_1-CO-$, in which $R_1$ is hydrogen or one of the mentioned organic radicals bonded by a carbon atom, for example, one of the mentioned, optionally substituted lower alkyl, cycloalkyl, cycloalkyl-lower alkyl, phenyl or phenyl-lower alkyl radicals. In a sulphonyl radical $R_\sigma-SO_2-$, $R_o$ is, for example, an optionally substituted aliphatic, araliphatic or aromatic hydrocarbon radical having up to 12 carbon atoms, and is especially lower alkyl, such as methyl, ethyl or a methyl substituted by an optically active radical, such as camphoryl, or benzyl, phenyl or toluyl. A halogen radical W is bromine, iodine or especially chlorine. W is preferably acetoxy or chlorine.

The nucleophilic substitution may be carried out under neutral or weakly basic conditions in the presence of water and optionally a water-miscible organic solvent. The basic conditions may be established, for example, by the addition of an inorganic base such as an alkali metal or an alkaline earth metal hydroxide, carbonate or bicarbonate, for example sodium, potassium or calcium hydroxide, carbonate or bicarbonate. The organic solvents that may be used are, for example, water-miscible alcohols, for example, lower alkanols such as methanol or ethanol; ketones, for example lower alkanones such as acetone; amides, for example lower alkanecarboxylic acid amides such as dimethylformamide, and the like. The reaction is usually carried out at room temperature but can be carried out at elevated or reduced temperature. The reaction can be accelerated by adding a salt of hydriodic acid or thiocyanic acid, for example an alkali metal salt, such as a sodium salt.

Both optically inactive cis- or trans-compounds of the formula III and mixtures thereof, or corresponding optically active compounds, can be used in the reaction The group $R_1-C(=Z')-S-$ which is introduced is directed by the group $R_a$ especially into the trans-position, irrespective of whether W is in the cis- or trans-position with respect to the $R_a$ group. Although predominantly the trans-isomers are formed, occasionally also cis-isomers are isolated. The separation of the cis- and trans-isomers is carried out according to conventional methods, especially by chromatography and/or by crystallisation.

The subsequent ozonisation of a methylidene group Z' can be carried out as described further below. A resulting racemate of the formula IV can be separated into the optically active compounds.

The compounds of the formula IV are new.

The optically active compounds of the formula IVa covered by the formula IV can also be produced according to the reaction scheme 2 given below Azetidinones of the formula III, in which $R_a$ is methyl and W is acetyl, phenylsulphonyl or camphor-10-sulphonyl, are known (German Offenlegungsschrift No. 1 906 401 or K. Clauss et. al., Liebigs Ann. Chem. 974, 539–560). The remaining compounds of the formula III are new. They can be produced according to methods that are known per se.

The azetidinones of the formula III are produced, for example, by the addition of chlorosulphonyl isocyanate to correspondingly substituted vinyl esters and subsequently splitting off the chlorosulphonyl group. In this synthesis, usually mixtures of cis- and trans-isomers are obtained, which if desired can be separated into the pure cis- or trans-isomers, for example by chromatography and/or crystallisation or distillation. The pure cis- and trans-isomers are present in the form of racemic compounds and can be separated into their optical antipodes, for example when the acyl in the acyloxy radical W in compounds of the formula III stems from an optically active acid The optically active compounds of the formula IIIa covered by the formula III can be produced according to reaction scheme 3 given below.

Stage 1.2

An α-hydroxycarboxylic acid compound of the formula V is obtained by reacting a compound of the formula IV with a glyoxylic acid compound of the formula $OHC-C(=C)-R_2^4$ or a suitable derivative such as a hydrate, hemihydrate or semiacetal, for example a semiacetal with a lower alkanol, for example, methanol or ethanol, and, if desired, separating a so obtained isomeric mixture into the individual isomers, and/or, if desired, converting a group $R_a$ or $R_1$ in a compound obtained into a different group $R_a$ or $R_1$ respectively, and/or, if desired, converting an optionally substituted methylidene group $Z'$ into an oxo group $Z$.

The compound V is usually obtained as a mixture of the two isomers (with reference to the grouping

It is possible, however, also to isolate the pure isomers therefrom.

The addition reaction of the glyoxylic acid ester compound to the nitrogen atom of the lactam ring takes place at room temperature or, if necessary, while heating, for example up to approximately 100° C., and in the absence of an actual condensation agent and/or without the formation of a salt. When using the hydrate of the glyoxylic acid compound, water is formed which, if necessary, is removed by distillation, for example azeotropically, or by using a suitable dehydration means such as a molecular sieve. Preferably the process is carried out in the presence of a suitable solvent, such as, for example, dioxan, toluene or dimethylformamide, or of a solvent mixture, if desired or necessary in an inert gas atmosphere, such as a nitrogen atmosphere.

Both pure optically inactive cis- or trans-compounds of the formula IV and mixtures thereof, or corresponding optically active compounds, can be used in the reaction. A racemic compound of the formula V obtained can be separated into the optically active compounds.

Stage 1.3

Compounds of the formula VI, in which $X_o$ represents a reactive esterified hydroxy group, especially halogen or organic sulphonyloxy, are produced by converting the secondary hydroxy group in a compound of the formula V into a reactive esterified hydroxy group, especially into halogen, for example chlorine or bromine, or into an organic sulphonyloxy group such as lower alkylsulphonyloxy, for example methylsulphonyloxy, or arylsulphonyloxy, for example 4-methylphenylsulohonyloxy, if desired separating an isomeric mixture obtained into the individual isomers, and, if desired, converting a group $R_a$ or $R_1$ in a compound obtained into a different group $R_a$ or $R_1$ respectively, and/or, if desired, converting an optionally substituted methylidene group $Z'$ into an oxo group $Z$.

The compound VI may be obtained in the form of mixtures of the isomers (with reference to the grouping

or in the form of pure isomers.

The above reaction is carried out by treating with a suitable esterifying agent, using, for example, a halogenating agent such as a thionyl halide, for example the chloride, a phosphorus oxyhalide, especially the chloride, or a halophosphonium halide such as triphenylphosphine dibromide or diiodide, and a suitable organic sulphonic acid halide such basic, especially an organic basic, agent such as an aliphatic tertiary amine, for example triethylamine, diisopropylethylamine or "polystyrene-Hünig base", or a heterocyclic base of the pyridine type, for example pyridine or collidine. Preferably the reaction is carried out in the presence of a suitable solvent, for example dioxane or tetrahydrofuran, or of a solvent mixture, if necessary while cooling and/or in an inert gas atmosphere, such as a nitrogen atmosphere.

In a compound of the formula VI obtainable in this manner, a reactive esterified hydroxy group $X_o$ can be converted into a different reactive esterified hydroxy group in a manner known per se. For example, a chlorine atom can be exchanged for a bromine or iodine atom by treating the corresponding chlorine compound with a suitable bromine or iodine reagent, especially with an inorganic bromide or iodide salt such as lithium bromide., preferably in the presence of a suitable solvent such as ether.

Both pure optically inactive cis- or trans-compounds of the formula V and mixtures thereof, or corresponding optically active compounds, can be used in the reaction. A racemic compound of the formula VI obtained can be separated into the optically active compounds.

Stage 1.4

A starting material of the formula II is obtained by treating a compound of the formula VI in which $S_o$ represents a reactive esterified hydroxy group, with a suitable phosphine compound such as a tri-lower alkylphosphine, for example tri-n-butylphosphine, or a triaryl-phosphine, for example triphenylphosphine, or with a suitable phosphite compound such as a tri-lower alkyl phosphite, for example triethyl phosphite, or an alkali metal dimethyl phosphite, wherein depending on the choice of reagent a compound of the formula IIA or IIB can be obtained, and if desired converting a group $R_a$ or $R_1$ in a compound obtained into a different group $R_a$ or $R_1$ respectively, and/or if desired converting an optionally substituted methylidene group $Z'$ into an oxo group $Z$.

The above reaction is preferably carried out in the presence of a suitable inert solvent such as a hydrocarbon, for example hexane, cyclohexane, benzene, toluene or xylene; or an ether, for example dioxan, tetrahydrofuran or diethylene glycol dimethyl ether, or of a solvent mixture. Depending on the reactivity, the operation is carried out while cooling or at elevated temperature, approximately between $-10°$ $+100°$, preferably at approximately 20° to 80°, and/or in an inert gas atmosphere, such as a nitrogen atmosphere. In order to prevent oxidative processes, catalytic amounts of an antioxidant, for example hydroquinone, may be added.

When using a phosphine compound the reaction is usually carried out in the presence of a basic agent, such as an organic base, for example an amine, such as triethylamine, diisopropylethylamine or "polystyrene-Hünig base", and thus the phosphoranylidene starting material of the formula IIA, which is formed from the corresponding phosphonium salt, is obtained directly.

Both pure optically inactive cis- or trans-compounds of the formula VI and mixtures thereof, be used in the reaction. A racemic compound of the formula II obtained can be separated into the optically active compounds.

In the compounds of the formulae II to VI $R_a$ preferably represents one of the mentioned organic radicals bonded by a carbon atom to the ring carbon atom, or alternatively an etherified hydroxy group, in which functional groups optionally present in such a radical $R_a$ are preferably in protected form.

The separation of the above-mentioned cis- trans compounds into the pure cis- and trans-isomers is effected according to customary separation methods, for example by chromatography and/or by distillation or crystallisation.

The above-mentioned racemic compounds are split into their optical antipodes by methods known per se.

One of these methods consists in reacting a racemic compound with an optically active auxiliary, separating the resulting mixture of two diastereoisomeric compounds by means of suitable physical/chemical methods and then splitting the individual diastereoisomeric compounds into the optically active compounds.

Particularly suitable racemic compounds for separating into antipodes are those that possess an acidic group, for example racemic compounds of the compounds of the formula I. Others of the described racemic compounds can be converted into acidic racemic compounds by simple reactions. For example, racemic compounds carrying aldehyde or keto groups react with a hydrazine derivative carrying acid groups, for example 4-(4-carboxyphenyl)-semicarbazide to form the corresponding hydrazone derivatives, or compounds containing alcohol groups react with a dicarboxylic acid anhydride, for example phthalic acid anhydride, to form the racemic compound of an acidic semiester.

These acidic racemic compounds may be reacted with optically active bases, for example esters of optically active amino acids, or (−)-brucine, (+)-quinidine, (−)-quinine, (+)-cinchonine, (+)-dehydroabietylamine, (+)- and (−)-ephedrine, (+)- and (−)-1-phenylethylamine or their N-mono- or N,N-dialkylated derivatives, to form mixtures consisting of two diastereoisomeric salts.

In racemic compounds containing carboxyl groups, for example in racemic compounds that contain a functionally modified carboxymethylidene group Z', this carboxyl group may already be esterified by, or esterification may be carried out by, an optically active alcohol such as (−)-menthol, (+)-borneol, (+)- or (−)-2-octanol, whereupon after subsequent isolation of the desired diastereoisomer, the carboxyl group is released, or the part of the molecule containing the esterified carboxyl group, for example the esterified carboxymethylidene radical, is split off.

Racemic compounds containing hydroxy groups may likewise be split into their optical antipodes, for which especially optically active acids or their reactive functional derivatives that form diastereoisomeric esters with the said alcohols are used. Such acids are, for example (−)-abietic acid, D(+)- and L(−)-malic acid, N-acylated optically active amino acids, (+)- and (−)-camphanic acid, (+)- and (−)-ketopinic acid, L(+)-ascorbic acid, (+)-camphoric acid, (+)-camphor-10-sulphonic acid(β), (+)- or (−)-α-bromocamphor-π-sulphonic acid, D(−)-quinic acid, D(−)-isoascorbic acid, D(−)- and L(+)-mandelic acid, (+)-1-menthoxyacetic acid, D(−)- and L(+)-tartaric acid and their di-O-benzoyl- and di-O-p-toluyl derivatives. The acyl radicals of the optically active acids mentioned may be present, for example, as acyl in compounds of the formula III or as $R_1-C(=O)-$ in compounds of the formulae II and IV to VI, and render possible the splitting of the racemates of such compounds. If desired or necessary, when the splitting of the racemic compound is complete the optically active group $R_1-C(=O)-$ can be converted into a desired optically inactive group $R_1-C(=O)-$.

Racemic compounds containing hydroxy groups may be converted into a mixture of diastereoisomeric urethanes, for example by reacting with optically active isocyanates, such as with (+)- or (−)-1-phenylethyl isocyanate.

Basic racemic compounds can form diastereoisomeric salts with the optically active acids. Racemic compounds containing double bonds may be converted, for example by platinum chloride and (+)-1-phenyl-2-aminopropane, into mixtures of diastereoisomeric complex salts.

Physical/chemical methods, especially fractional crystallisation, are suitable for separating the diastereoisomeric mixtures. It is also possible, however, to use chromatographic methods, above all solid-liquid chromatography. Readily volatile diastereoisomeric mixtures may also by separated by distillation or gas chromatography.

Splitting the separated diastereoisomers into the optically active starting materials is likewise carried out according to customary methods. The acids or the bases are freed from the salts, for example by treating with stronger acids or bases respectively than those originally used. The desired optically active compounds are obtained from the esters and urethanes, for example by alkaline hydrolysis or by reduction with a complex hydride such as lithium aluminium hydride.

A further method of separating the racemic compounds consists in the chromatography on optically active absorption layers, for example on cane sugar.

According to a third method, the racemic compounds can be dissolved in optically active solvents and the more sparingly soluble optical antipode is crystallised out.

In a fourth method the different reactivity of the optical antipodes in comparison with the biological material, such as microorganisms or isolated enzymes, is used.

According to a fifth method, the racemic compounds are dissolved and one of the optical antipodes is crystallised out by injecting a small amount of an optically active product obtained according to the above methods.

Optically active trans-compounds of the formula IVa that can be used according to the invention may also be produced in accordance with the following reaction scheme:

Reaction scheme 2

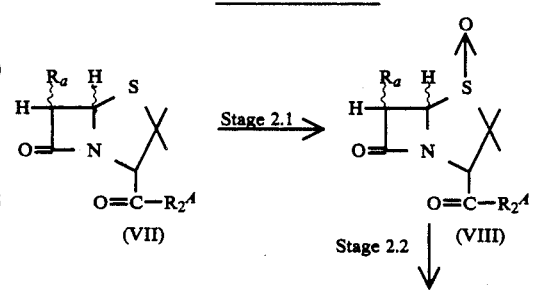

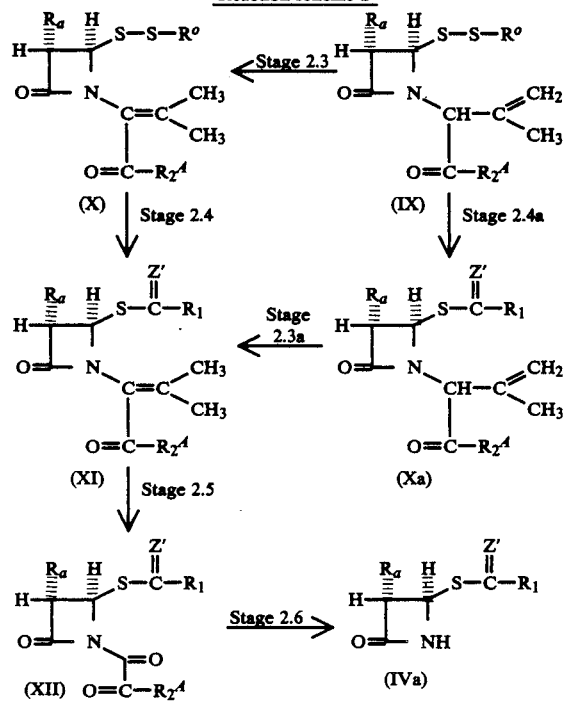

Stage 2.1

An oxide of a penicillanic acid compound of the formula VIII is obtained by oxidizing a penicillanic acid compound of the formula VII in the 1-position and if desired converting an $R_a$ group in a resulting compound into a different $R_a$ group. The oxidation is carried out in a manner known per se with suitable oxidising agents, such as hydrogen peroxide or inorganic or organic peracids. Suitable inorganic peracids are, for example, periodic or persulphuric acid. Suitable organic peracids are, for example, percarboxylic acids, such as performic acid, peracetic acid, trifluoroperacetic acid, permaleic acid, perbenzoic acid, 3-chloroperbenzoic acid or monoperphthalic acid, or persulphonic acids, for example p-toluenepersulphonic acid. The peracids may also be produced in situ from hydrogen peroxide and the corresponding acids. The oxidation is carried out under mild conditions, for example at temperatures of approximately $-50°$ to approximately $+100°$, preferably at approximately $-10°$ to approximately $+40°$, in an inert solvent.

Racemic 1-oxides of the formula VIII, in which $R_a$ is phenoxy or methoxy, and $R_2^A$ is methoxy, are known [A. K. Bose et al., Tetrahedron 28, 5977 (1972)]. The optically active compounds of the formula VIII are new and are also part of the present invention.

Starting compounds of the formula VII are known or can be produced according to known processes. For example, they may be obtained according to D. Hauser and H. P. Sigg, Helv. Chimica Acta 50, 1327 (1967), by reacting a 6-diazopenicillanic acid ester, which is optionally produced in situ from a 6-amino-penicillanic acid ester and nitrous acid, with water or an alcohol or an acid of the formula H-$R_a$. Compounds of the formula VII, in which $R_a$ is an acyloxy group, may likewise be obtained according to D. Hauser, by pyrolysing a corresponding 6α- or 6β-N-nitrosoacylaminopenicillanic acid ester in an inert solvent. Compounds of the formula VII, in which $R_a$ is hydroxy, have also been described by J. C. Sheehan et al., J. Org. Chem. 39, 1444 (1974) (manufacture from the corresponding 6-diazopenicillanic acid compounds). Further starting materials of the formula VII, in which $R_a$ is optionally protected 1-hydroxyethyl, bromine or iodine, are described by DiNinno et al. (J. Org. Chem. 42 (1967), 2960). In a resulting compound of the formula VIII, an $R_a$ group can be converted into a different $R_a$ group.

Stage 2.2

A 3-methylenebutyric acid compound of the formula IX is obtained by treating a 1-oxide of a penicillanic acid compound of the formula VIII with a mercapto compound $R^o$—SH, and if desired, converting a group $R_a$ in a resulting compound into a different group $R_a$.

In the mercapto compound $R^o$—SH and in the reaction product of the formula IX, $R^o$ is an optionally substituted aromatic heterocyclic radical having up to 15, preferably up to 9, carbon atoms, and at least one ring nitrogen atom, and optionally a further ring hetero atom, such as oxygen or sulphur, which radical is bonded to the thio group —S— by one of its ring carbon atoms that is bonded to a ring nitrogen atom by a double bond. Radicals of this type are monocyclic or bicyclic and may be substituted, for example by lower alkyl, such as methyl or ethyl, lower alkoxy, such as methoxy or ethoxy, halogen, such as fluorine or chlorine or aryl, such as phenyl.

Radicals $R^o$ of this type are, for example, monocyclic five-membered thiadiazacyclic, thiatriazacyclic, oxadiazacyclic or oxatriazacyclic radicals of aromatic character, especially monocyclic five-membered diazacyclic, oxazacyclic and thiazacyclic radicals of aromatic character, and/or especially the corresponding benzdiazacyclic, benzoxazacyclic or benzthiazacyclic radicals, in which the heterocyclic part is five-membered and has an aromatic character, wherein in $R^o$ radicals a substitutable ring nitrogen atom may be substituted, for example, by lower alkyl. Representative of such $R^o$ groups are 1-methylimidazol-2-yl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, 2-quinolyl, 1-methylbenzimidazol-2-yl, benzoxazol-2-yl and especially benzthiazol-2-yl.

The reaction is carried out in an inert solvent, such as an aliphatic or aromatic hydrocarbon, for example benzene or toluene, while warming up to the reflux temperature of the solvent used.

Stage 2.3

A 3-methylcrotonic acid compound of the formula X is obtained by isomerising a 3-methylenebutyric acid compound of the formula IX by treating with a suitable basic agent and, if desired, converting a group $R_a$ in a resulting compound into a different group $R_a$.

Suitable basic agents are, for example, organic nitrogen bases such as tertiary amines, for example tri-lower alkylamines such as triethylamine or Hünig base, or inorganic bases, which are used in an inert solvent, such as an optionally halogenated hydrocarbon, for example methylene chloride, at room temperature or optionally slightly reduced or elevated temperature.

Stage 2.4

A thio compound of the formula XI is obtained by treating a compound of the formula X with a suitable reducing agent and simultaneously or subsequently reacting with an acylation derivative of an acid of the formula $R_1$—C(=Z)—OH, or, when Z' represents a methylidene group optionally substituted by Y, reacting with an alkyne of the formula $R_1$—C≡C—Y, and, if desired, converting a group $R_a$ or $R_1$ in a compound so obtained into a different group $R_a$ or $R_1$ respectively, and/or, if desired, converting an optionally substituted methylidene group Z' into an oxo group Z.

Suitable reducing agents are, for example, hydride reducing agents such as alkali metal borohydrides, for example sodium borohydride, or also zinc in the presence of a carboxylic acid, for example a carboxylic acid of the formula $R_1$—C(=O)—OH. The hydride reducing agents are usually used in the presence of suitable solvents, such as dimethylformamide. The hydride reduction is preferably carried out in dimethylformamide with sodium borohydride at temperatures of approximately $-50°$ to approximately $-10°$, preferably at approximately $-20°$, whereupon at the same temperature the acylating agent and optionally a tertiary base, such as pyridine, are added. The reduction with zinc and a carboxylic acid is optionally carried out in a solvent, for which the carboxylic acid, if liquid, can itself be used, at temperatures of approximately $-10$ to approximately $+50°$, preferably at approximately $0°$ to room temperature. The acylating agent can be added to the reduction mixture from the beginning or when reduction is complete and optionally after evaporating off the carboxylic acid used and/or the solvent. Suitable acylating agents are especially anhydrides of the carboxylic acids mentioned, such as symmetric anhydrides, for example acetic anhydride, or mixed anhydrides, preferably those with hydrohalic acids, that is the corresponding carboxylic acid halides, for example the chlorides and bromides, such as acetyl bromide. For example a compound of the formula X may be converted with zinc in a mixture of acetic acid and acetic anhydride at $0°$ to approximately $20°$ into a compound of the formula XI, in which $R_1$ is methyl. Owing to the reduced risk of racemisation, the zinc/carboxylic acid reduction is preferred. The alkyne can also be added to the reduction mixture from the beginning or when reduction is complete. The addition of the 4-mercaptoazetidin-2-one, produced as an intermediate in the reduction, to the triple bond of the alkyne takes place spontaneously at the reduction temperature.

Stage 2.3a

A thio compound of the formula XI is also obtained by isomerising a compound of the formula Xa in accordance with the reaction conditions of stage 2.3 by treating with a suitable basic agent, if desired converting a group $R_a$ or $R_1$ in a compound obtained into different group $R_a$ or $R_1$ respectively, and/or, if desired, converting an optionally substituted methylidene group Z' into an oxo group Z.

Stage 2.4a

A compound of the formula Xa is obtained by treating a 3-methylenebutyric acid compound of the formula IX in accordance with the reaction conditions of stage 2.4 with a suitable reducing agent, and simultaneously or subsequently reacting with an acylating derivative of a carboxylic acid of the formula $R_1$—C(=Z)—OH, or, when Z' represents a methylidene group optionally substituted by Y, with an alkyne of the formula $R_1$—C≡C—Y, and, if desired, converting a group $R_a$ or $R_1$ in a compound obtained into a different group $R_a$ or $R_1$ respectively, and/or, if desired, converting an optionally substituted methylidene group Z' into an oxo group Z.

Stage 2.5

A 2-oxoacetic acid compound of the formula XII is obtained by ozonising a compound of the formula XI and splitting the ozonide formed to the oxo compound by means of reduction, and if desired converting a group $R_a$ or $R_1$ in a compound obtained into a different group $R_a$ or $R_1$ respectively, and/or, if desired, converting an optionally substituted methylidene group Z' into an oxo group Z.

The ozonisation is usually carried out with an ozone/oxygen mixture in an inert solvent, such as a lower alkanol, for example methanol or ethanol, a lower alkanone, for example acetone, an optionally halogenated aliphatic, cycloaliphatic or aromatic hydrocarbon, for example a halogen-lower alkane, such as methylene chloride or carbon tetrachloride, or in a solvent mixture, including an aqueous mixture, preferably while cooling, for example at temperatures of approximately $-90°$ to approximately $0°$.

An ozonide obtained as intermediate is, usually without being isolated, split reductively to form a compound of the formula XII, wherein catalytically activated hydrogen, for example hydrogen in the presence of a heavy metal hydrogenating catalyst, such as a nickel catalyst or palladium catalyst, preferably on a suitable carrier material, such as calcium carbonate or carbon, is used; or chemical reducing agents, such as reducing heavy metals, including heavy metal alloys or amalgams, for example zinc, in the presence of a hydrogen donor such as an acid, for example acetic acid, or of an alcohol, for example a lower alkanol, are used; or reducing inorganic salts, such as alkali metal iodides, for example sodium iodide, or alkali metal bisulphites, for example, sodium bisulphite, in the presence of a hydrogen donor, such as an acid, for example acetic acid, or water, are used; or reducing organic compounds such as formic acid are used. It is also possible to use as reducing agents compounds that may readily be converted into corresponding epoxy compounds or oxides, wherein the epoxide formation can take place on account of a C,C-double bond and the oxide formation on account of an oxide-forming hetero atom, such as a sulphur, phosphorus or nitrogen atom. Compounds of this type are, for example, suitably substituted ethylene compounds (which are converted into ethylene oxide compounds in the reaction), such as tetracyanoethylene, in particular suitable sulphide compounds (which in the reaction are converted into sulphoxide compounds), such as di-lower alkyl sulphides, especially dimethyl sulphide, suitable organic phosphorus compounds, such as a phosphine, which contains optionally substituted aliphatic or aromatic hydrocarbon radicals as substituents (and which in the reaction is converted into a phosphine oxide), such as tri-lower alkylphosphines, for example tri-n-butylphosphine, or triarylphosphines, for example triphenylphosphine, or phosphites, which contain optionally substituted aliphatic hydrocarbon radicals as substituents (and in the reaction are converted into phosphoric acid triesters), such as tri-lower alkyl phosphites, usually in the form of corresponding alcohol adduct compounds, such as trimethyl phosphite, or phosphorous acid triamides, which contain optionally substituted aliphatic hydrocarbon radicals as substituents, such as hexa-lower alkyl phosphorous acid triamides, for example hexamethyl phosphorous acid triamide, the latter preferably in the form of a methanol adduct, or suitable nitrogen bases (which in the reaction are converted into the corresponding N-oxides), such as heterocyclic nitrogen bases of aromatic nature, for example bases of the pyridine types and especially pyridine itself. The splitting of the usually unisolated ozonide is normally carried out under the conditions used for its manufacture, that is to say, in the presence of a suitable solvent or solvent mixture, and while cooling or heating gently, wherein preferably temperatures of approximately −10° C. to approximately +25° C. are used and the reaction usually terminates at room temperature.

Stage 2.6

A compound of the formula IVa is obtained by solvolysing a compound of the formula XII and, if desired, converting a group $R_a$ or $R_1$ in a compound so obtained into a different group $R_a$ or $R_1$, and/or, if desired, converting an optionally substituted methylidene group $Z'$ into an oxo group Z.

The solvolysis may be carried out by hydrolysis alcoholysis or hydrazinolysis. The hydrolysis is carried out with water, optionally in a water-miscible solvent. The alcoholysis is usually carried out with a lower alkanol, for example methanol or ethanol, preferably in the presence of water and an organic solvent, such as a lower alkanecarboxylic acid lower alkyl ester, for example ethyl acetate, preferably at room temperature, if necessary while cooling or heating. The hydrazinolysis is carried out in a conventional manner with a substituted hydrazine, for example with phenylhydrazine or a nitrophenylhydrazine, such as 2-nitrophenylhydrazine, 4-nitro-phenylhydrazine or 2,4-dinitrophenylhydrazine, which is preferably used in an approximately equimolar amount, in an organic solvent, such as an ether, for example tetrahydrofuran, dioxan, diethyl ether, an aromatic hydrocarbon, such as benzene or toluene, a halogenated hydrocarbon, such as methylene chloride, chlorobenzene or dichlorobenzene, an ester, such as ethyl acetate, or the like, at temperatures between approximately room temperature and approximately 65° C. The α-keto. compound of the formula XII does not necessarily have to be isolated. If, for example, the ozonide is split in the presence of a solvolysing agent, such as, for example, water, a compound of the formula IVa can be obtained directly.

Optically active cis-, trans- and cis-trans compounds of the formula IIIa may also be obtained in accordance with the following reaction scheme:

Reaction scheme 3

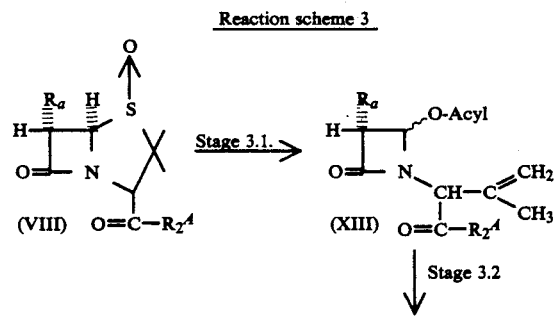

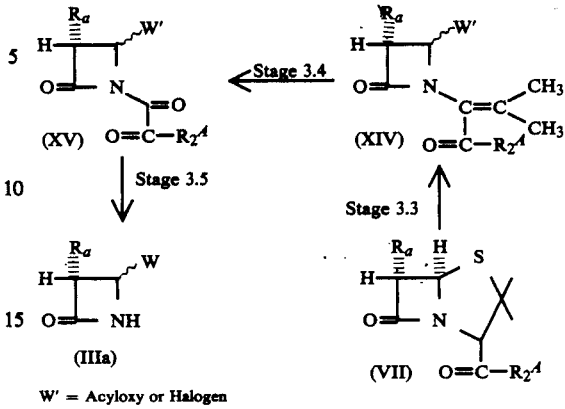

W' = Acyloxy or Halogen

Stage 3.1

A 3-methylenebutyric acid compound of the formula XIII is obtained by treating a 1-oxide of a penicillanic acid compound of the formula VIII in the presence of a tri-lower alkyl phosphite with an organic carboxylic acid acyl-OH, if desired converting a group $R_a$ in a resulting compound into a different group $R_a$, and/or isolating the cis- and/or the trans-compound from a resulting cis-trans compound.

A suitable tri-lower alkyl phosphite is, for example, trimethylphosphite. A suitable organic carboxylic acid acyl-OH is, for example, a carboxylic acid $R_1$—COOH, in which $R_1$ represents hydrogen or one of the mentioned organic radicals bonded by a carbon atom, for example one of the mentioned lower alkyl, cycloalkyl, cycloalkyl-lower alkyl, phenyl or phenyl-lower alkyl radicals. Preferred are lower alkanecarboxylic acids, including formic acid, especially acetic acid.

The reaction is effected, analogously to A. Suarato et. al., Tetrahedron Letters, 42, 4059–4062, 1978, in an inert organic solvent, for example a hydrocarbon, such as benzene, toluene or xylene, or an ether-type solvent, such as dioxan or tetrahydrofuran, or a solvent mixture, at elevated temperature, approximately up to the reflux temperature of the solvent used, at approximately 50° to 150° C., preferably at approximately 80° to approximately 100° C.

In the reaction a mixture of the cis- and trans-compounds is obtained. By means of customary separating methods, such as crystallisation or chromatography, the cis- and/or trans- compound can be obtained in pure form.

Stage 3.2

A 3-methylcrotonic acid compound of the formula XIV, in which W' represents acyloxy, is obtained by isomerising a 3-methylenebutyric acid compound of the formula XIII by treating with a suitable basic agent, and if desired converting a group $R_a$ in a resulting compound into a different group $R_a$, and/or, if desired isolating the cis- and/or trans-compound from a resulting cis-trans compound.

The basic isomerisation is carried out as described in stage 2.3. The subsequent separation into pure compounds, to be carried out if desired, is effected as described in stage 3.1.

Stage 3.3

A compound of the formula XIV, in which W' represents halogen, is obtained by treating a penicillanic acid compound of the formula VII with a halogenating agent yielding positive halogen ions and, if necessary, treating a possibly resulting intermediate with a base, and if desired converting a group $R_a$ in a resulting compound of the formula XIV into a different group $R_a$, and/or isolating the cis- and/or the trans-compound from a resulting cis-trans compound.

Halogenating agents that yield positive halogen ions are for example elemental halogens, such as chlorine, bromine or iodine; mixed halogens, such as BrCl, ClI or BrI; sulphuryl halides, such as sulphuryl chloride or sulphuryl bromide; N-haloamides or N-haloimides, such as N-chloroacetamide, N-bromoacetamide, N-chlorosuccinimide, N-bromosuccinimide or N,N'-dibromohydantoine; or organic hypohalites, especially lower alkanoyl hypohalites, such as acetyl hypochlorite, propionyl hypochlorite, butyryl hypochlorite, acetyl hypobromite, propionyl hypobromite, butyryl hypobromite and the like.

The reaction is carried out analogously to U.S. Pat. No. 3,920,696 or St. Kukolja, Journ. Am. Chem. Soc. 93, 6267 (1971), in an inert aprotic solvent, especially in a halogenated hydrocarbon, such as methylene chloride or carbon tetrachloride, at temperatures between approximately $-80°$ and approximately $+80°$ C., preferably at approximately $-76°$ C. to approximately room temperature.

The molar ratio of halogenating agent to compound of the formula VII is between 1:1 and 3:1 or even higher. If the molar ratio is approximately 1:1, a compound of the formula

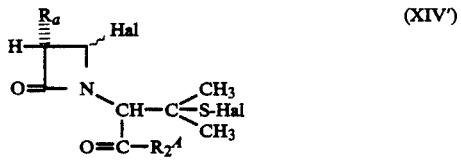

is obtained as intermediate, which can be converted into a compound of the formula XIV by treating with a base, such as a tertiary amine, for example triethylamine. By using at least 2 moles of halogenating agent or more per mole of penicillanic acid compound, the desired compound of the formula XIV is obtained even without subsequent treatment with a base.

In the ring opening reaction a mixture of the cis- and trans-compound is obtained, the trans-compound preferably being formed. By customary separating methods, such as crystallisation or chromatography, the cis- and/or the trans-compounds can be obtained in pure form.

Stage 3.4

A 2-oxoacetic acid compound of the formula XV, in which W' represents acyloxy or halogen, is obtained by ozonising a compound of the formula XIV and splitting the ozonide formed by reduction to form the oxo group, and, if desired, converting a group $R_a$ in a resulting compound into a different group $R_a$, and/or, if desired, isolating the cis- and/or trans- compound from a resulting cis-trans compound.

The ozonisation and the reduction of the ozonide formed are carried out as described in stage 2.5. The separation into pure compounds carried out subsequently if desired, is effected as described in stage 3.1.

Stage 3.5

A compound of the formula IIIa, in which W has the meaning given under formula III, is obtained by solvolysing a compound of the formula XV, in which W' represents acyloxy or halogen, and if desired converting a group $R_a$ in a resulting compound into a different group $R_a$, and/or, if desired, converting a group W' into a different group W' or W, and/or if desired isomerising a resulting cis-compound to form the corresponding trans-compound, and/or isolating the cis- and/or trans-compound from a resulting cis-trans compound.

The solvolysis is carried out as described in stage 2.6. When W is halogen, hydrazinolysis is preferably used. In this case too it is not necessary to isolate the intermediate of the formula XV after the ozonisation and reduction reaction, but it can be produced in situ and solvolysed directly.

In a resulting compound of the formula IIIa in which W represents acyloxy or halogen, this group can be converted into a different group W by nucleophilic exchange, wherein the group W being introduced must be more nucleophilic than that leaving. This exchange may be carried out analogously to stage 1.1, for example, by treating with an alkali metal salt, such as a sodium or potassium salt of an acid H-W.

In this exchange of W for a different W, and in the subsequent exchange for a group $R_1$—C(=Z')—S— according to stage 1.1, the optically active trans-compounds of the formula IIIa and IVa respectively are obtained in excess, irrespective of whether a cis- or trans-compound was used as starting material.

By isomerisation, for example by treating with a mild Lewis acid in catalytic amounts, a resulting cis-compound can be converted into a trans-compound. The isomerisation with a Lewis acid is carried out in an inert solvent at elevated temperature, approximately at 50° to 150° C., for example under reflux in benzene.

In the compounds II, IV to XV, IIIa and IVa, a group $R_a$, $R_1$ or $R_2^A$ can be converted according to methods known per se into a different $R_a$, $R_1$ or $R_2^A$ group respectively, wherein, taking into consideration the various functional groups, it is possible to use the same methods as are given for converting these substituents in the compounds of the formula I.

In the compounds IV (including IVa) to VI and II, an optionally substituted methylidene group Z' may be converted into an oxo group Z by ozonisation and subsequent reduction of the ozonide formed, according to the process described in stage 2.5.

The invention likewise includes the new intermediates, such as those of the formulae IIIa and IV (including IVa) to XV and especially of the formula II, and the processes for their production.

The pharmacologically acceptable compounds of the invention may be used, for example, for the production of pharmaceutical preparations that contain an effective amount of the active substance together or in admixture with inorganic or organic, solid or liquid, pharmaceutically acceptable carriers that are suitable for enteral or parenteral administration. For example, tablets or gelatin capsules that contain the active substance together with diluents, for example lactose, dextrose, sucrose, mannitol, sorbitol, cellulose and/or glycine, and lubricants, for example silica, talcum, stearic acid or salts thereof, such as magnesium or calcium stearate, and/or polyethylene glycol; tablets also contain binders, for example magnesium aluminium silicate, starches such as maize, wheat, rice or arrowroot starch, gelatin, tragacanth, methylcellulose, sodium carboxymethylcellulose and/or polyvinylpyrrolidone, and, if desired, disintegrating agents, for example starches, agar, alginic acid or a salt thereof, such as sodium alginate, and/or effervescing mixtures, or adsorbents, dyestuffs, flavouring substances and sweeteners. Also, the new pharmacologically active compounds can be used in the form of injectable, for example intravenously administrable, preparations or in the form of infusion solutions. Solutions of this type are preferably isotonic aqueous solutions or suspensions, wherein these can be produced before use, for example, from lyophilised preparations that contain the active substance alone or together with a carrier, for example mannitol. The pharmaceutical preparations may be sterilised and/or contain auxiliaries, for example preservatives, stabilisers, wetting agents and/or emulsifiers, solubilisers, salts for regulating the osmotic pressure and/or buffers. The pharmaceutical preparations of the invention which, if desired, may contain other pharmacologically valuable substances are produced in a manner known per se, for example by means of conventional mixing, granulating, pill-coating, dissolving or lyophilising processes and contain from approximately 0.1% to 100%, especially from approximately 1% to approximately 50%, in the case of the lyophilisates up to 100%, of the active substance.

Referring to the present description, organic radicals referred to as "lower", unless expressly defined, contain up to 7, preferably up to 4, carbon atoms; acyl radicals contain up to 20, preferably up to 12, and especially up to 7, carbon atoms.

The following Examples serve to illustrate the invention; temperatures are in degrees Centigrade. The following abbreviation is used: TLC=thin layer chromatogram over silica gel

EXAMPLE 1

4-acetylthio-3-methyl-2-oxoazetidine (racemic cis and trans compound)

A solution of 0.33 ml of thioacetic acid in 4.5 ml of 1N sodium hydroxide solution is added dropwise at room temperature under a nitrogen atmosphere to a solution of 438 mg (3.06 mmoles) of 4-acetoxy-3-methylazetidin-2-one (produced according to K. Clauss et al., Lieb, Ann. Chem., 1974, 539; racemic mixture of cis- and trans-isomer in a ratio of 3:1; Mp 53°–65°) in 1.13 ml of water and 0.27 ml of acetone, and the mixture is stirred at the same temperature for 3 hours. The reaction mixture is exhaustively extracted with methylene chloride. The combined organic phases are dried over sodium sulphate and concentrated by evaporation in vacuo. The residue is chromatographed over silica gel with toluene/ethyl acetate (4:1 to 3:2) and yields first of all the pure trans-compound, then a mixture of the cis- and trans-isomers of the title compound and subsequently the pure cis-compound.

TLC: $R_f=0.31$ (cis-isomer); 0.36 (trans-isomer) (toluene/ethyl acetate 2:3); IR spectrum (CH$_2$Cl$_2$): absorption bands at 2.95, 5.6, 5.87, 8.65, 8.85 and 10.45μ. NMR spectrum (in CDCl$_3$/100 Mc, in ppm): cis-compound: 6.2, 1H, wide (exchange with D$_2$O); 5.45, 1H, d(J=5.5 Hz); 3.5–3.9, 1H, m; 2.4, 3H, s; 1.3, 3H, d; trans-compound 6.5, 1H, wide (exchange with D$_2$O); 4.93, 1H, d (J~2.5 Hz); 3.0–3.4, 1H, m; 2.4, 3H, s; 1.42, 3H, d.

EXAMPLE 2

2-(4-acetylthio-3-methyl-2-oxoazetidin-1-yl)-2-hydroxyacetic acid p-nitrobenzyl ester (racemic cis-trans mixture)

A solution of 500 mg of 2-ethoxy-2-hydroxyacetic acid p-nitrobenzyl ester in a mixture of 10 ml of toluene and 2.5 ml of dimethylformamide is added at room temperature to 129 mg (0.81 mmole) of 4-acetylthio-3-methyl-2-oxoazetidine (racemic cis-trans mixture). After adding freshly dried molecular sieves, the mixture is stirred under nitrogen for 15 hours at room temperature and subsequently for 2 hours at 50°. The molecular sieves are filtered off, washed with toluene and the filtrate and washing liquid are together concentrated by evaporation in vacuo. The residue is dried under high vacuum and chromatographed over silica gel with toluene/ethyl acetate (9:1 to 8:2). After elution of the unreacted 2-ethoxy-2-hydroxyacetic acid p-nitrobenzyl ester a mixture of the cis-trans isomers of the title compound having the following physico-chemical properties is eluted:

TLC : $R_f=0.38$ (toluene/ethyl acetate 2:3); IR spectrum (CH$_2$Cl$_2$): absorption bands at 2.85, 5.62, 5.7, 5.9, 6.2, 6.55, 7.4 and 8.25μ.

EXAMPLE 3

2-(4-acetylthio-3-methyl-2-oxoazetidin-1-yl)-2-triphenylphosphoranylideneacetic acid p-nitrobenzyl ester (racemic cis-trans mixture)

(a) A solution of 225 mg of 2-(4-acetylthio-3-methyl-2-oxoazetidin-1-yl)-2-hydroxyacetic acid p-nitrobenzyl ester (racemic cis-trans mixture) in 5 ml of absolute dioxan is added to a solution of 1 g of poly-Hünig base in 2.5 ml of absolute dioxan that has already been stirred for 30 minutes. After adding a solution of 0.175 ml of thionyl chloride in 1.5 ml of absolute dioxan, the reaction mixture is stirred for 100 minutes at room temperature under nitrogen The poly-Hünig base is filtered off and washed with dioxan and the filtrate is concentrated by evaporation in vacuo. TLC of the crude 2-(4-acetylthi-o-3-methyl-2-oxoazetidin-1-yl)-2-chloroacetic acid p-nitrobenzyl ester (racemic cis-trans mixture): $R_f=0.62$ (toluene/ethyl acetate 2:3).

(b) The crude 2-(acetylthio-3-methyl-2-oxo-azetidin-1-yl)-2-chloroacetic acid p-nitrobenzyl ester obtained is dissolved in 12 ml of absolute dioxan, 1 g of poly-Hünig base is added and the mixture is stirred for 30 minutes, then 312 mg of triphenylphosphine are added and the mixture is stirred under nitrogen for 15 hours at 50°. The poly-Hünig base is filtered off, washed with dioxan and the filtrate and washing liquid are together concentrated by evaporation in vacuo. The residue is chromatographed over silica gel with toluene/ethyl acetate and yields a cis-trans mixture of the title compound having the following physico-chemical properties:

TLC : $R_f=0.28$ (toluene/ethyl acetate 2:3; IR spectrum (CH$_2$Cl$_2$): absorption bands at 5.67, 5.9, 6.15, 6.55, 6.95, 7.4, 9.0 and 9.25μ.

EXAMPLE 4

2,6-dimethyl-2-penem-3-carboxylic acid p-nitrobenzyl ester (racemic cis-trans mixture)

A catalytic amount of p-hydroxyquinone is added to a solution of 118 mg of 2-(4-acetylthio-3-methyl-2-oxoazetidin-1-yl)-2-triphenylphosphoranylideneacetic acid p-nitrobenzyl ester (racemic cis-trans mixture) in 50 ml of absolute toluene, and the mixture is stirred for 48 hours at 90° under nitrogen. The solvent is evaporated off in vacuo and the residue is chromatographed over silica gel with toluene/ethyl acetate (19:1). A cis-trans mixture (1:4) of the title compound is obtained in the form of a yellowish oil having the following physico-chemical properties:

TLC : $R_f=0.59$ (toluene/ethyl acetate 2:3); IR spectrum ($CH_2Cl_2$): absorption bands at 5.6, 5.85 6.3, 6.55, 7.4, 7.6, 8.3 and 9.25$\mu$; NMR spectrum (in $CDCl_3$/100 Mc, in ppm): 8.4–8.2, 2H; 7.75–7.76, 2H, m; 5.7–5.2, 3H, m; 4.1–3.6, 1H, m; 2.4, 2.43, 3H, 2s; 1.6–1.4, 3H, 2d.

EXAMPLE 5

2,6-dimethyl-2-penem-3-carboxylic acid (racemic cis-trans mixture)

2 ml of 0.2M aqueous sodium bicarbonate solution and 100 mg of 10% palladium/carbon catalyst are added to a solution of 47 mg (0.14 mmole) of 2,6-dimethyl-2-penem-3-carboxylic acid p-nitrobenzyl ester (racemic cis-trans mixture 1:4) in 3 ml of absolute ethyl acetate and the mixture is stirred at normal pressure for 40 minutes under hydrogen. The catalyst is filtered off from the hydrogenated mixture over diatomaceous earth, the residue is washed with 0.2M sodium bicarbonate solution and several times with ethyl acetate. The aqueous phase is washed with methylene chloride, acidified with 5% aqueous citric acid solution and exhaustively extracted with methylene chloride. The combined organic phases are dried over sodium sulphate, filtered, concentrated by evaporation in vacuo and dried under high vacuum. The title compound obtained (cis-trans mixture~1:4) has the following physico-chemical properties:

TLC : $R_f=0.28$ (toluene/ethyl acetate/acetic acid 60:40:5); IR spectrum ($CH_2Cl_2$): absorption bands at 3.5, 5.6, 5.95 and 6.3$\mu$; NMR spectrum (DMSO d6/100 Mc, in ppm): 5.65, 1H, q; 3.3–3.9, 2H, m (+$H_2O$); 2.28, 3H, s, melting point 119°.

EXAMPLE 6

Sodium salt of 2,6-dimethyl-2-penem-3-carboxylic acid (racenic cis-trans mixture)

A solution of 50 mg of 2,6-dimethyl-2-penem-3-carboxylic acid in the equivalent amount of aqueous sodium bicarbonate solution is concentrated by evaporation in vacuo and dried under high vacuum.

EXAMPLE 7

4-acetylthio-3-methyl-2-oxoazetidine (racemic trans-compound)

A solution of 1.5 ml of thioacetic acid in 20.5 ml of 1N sodium hydroxide solution is added dropwise at room temperature, under nitrogen, to a solution of 2 g of 4-acetoxy-3-methyl-azetidin-2-one (produced according to K. Clauss et. al., Lieb. Ann. Chem., 1974, 539; racemic mixture of cis- and trans-isomer in a ratio of 3:1, Mp. 53°–65°) in 5.16 ml of water and 1.25 ml of acetone, and the mixture is stirred at the same temperature for 3 hours. The reaction mixture is exhaustively extracted with methylene chloride. The combined organic phases are dried over sodium sulphate and concentrated by evaporation in vacuo. The residue is chromatographed over 150 g of silica gel with toluene/ethyl acetate (9:1) and yields the almost pure trans-isomer of the title compound with the following physico-chemical properties:

TLC: 0.38 (toluene/ethyl acetate 2:3); IR spectrum ($CH_2Cl_2$): absorption bands at 2.95, 5.6, 5.87, 7.37, 7.45, 8.62 and 8.82$\mu$. NMR spectrum (in $CD Cl_3$/100 Mc, in ppm) 6.55, 1H, m (exchange with $D_2O$); 4.9, 1H, d, J=2 Hz; 3.35–3.05, 1H, m; 2.38, 3H, s; 1.4, 3H, d, J=7 Hz. Subsequently a mixture of the cis- and trans-isomers is isolated.

EXAMPLE 8

2-(4-acetylthio-3-methyl-2-oxoazetidin-1-yl)-2-hydroxyacetic acid p-nitrobenzyl ester (racemic trans-compound)

At room temperature a solution of 5 g of 2-ethoxy-2-hydroxyacetic acid p-nitrobenzyl ester in a mixture of 100 ml of toluene and 25 ml of dimethylformamide is added to 1.35 g (8.49 mmole) of 4-acetylthio-3-methyl-2-oxoazetidine (racemic trans-compound). After adding freshly dried molecular sieves the mixture is stirred under nitrogen for 15 hours at room temperature and then for 2 hours at 50°. The molecular sieves are filtered off, washed with toluene and the filtrate and washing liquid are together concentrated by evaporation in vacuo. The residue is dried under high vacuum and chromatographed over 100 g of silica gel with toluene/ethyl acetate (9:1). After elution of the unreacted 2-ethoxy-2-hydroxyacetic acid p-nitrobenzyl ester, the title compound having the following physicochemical properties is eluted:

TLC : $R_f=0.33$ (toluene/ethyl acetate 2:3); IR spectrum ($CH_2Cl_2$): absorption bands at 2.85, 5.6, 5.7, 5.87, 6.2, 6.52, 7.4, 8.28 and 9–9.2$\mu$.

EXAMPLE 9

2-(4-acetylthio-3-methyl-2-oxoazetidin-1-yl)-2-triphenylph-os-phoranylideneacetic acid p-nitrobenzyl ester racemic trans-compound (a) A solution of 3 g of 2-(4-acetylthio-3-methyl-2-oxoazetidin-1-yl)-2-hydroxyacetic acid p-nitrobenzyl ester (racemic trans-compound) in 75 ml of absolute dioxan is added to a solution of 13.5 g of poly-Hünig base in 35 ml of absolute dioxan that has already been stirred for 30 minutes. After adding a solution of 2.4 ml of thionyl chloride in 22.4 ml of absolute dioxan, the reaction mixture is stirred for 100 minutes at room temperature under nitrogen. The poly-Hünig base is filtered off, washed with dioxan and the filtrate is concentrated by evaporation in vacuo.

TLC of the crude 2-(4-acetylthio-3-methyl-2-oxoazetidin-1-yl)-2-chloroacetic acid p-nitrobenzyl ester (racemic trans-compound): $R_f=0.59$ (toluene/ethyl acetate 2:3).

(b) The resulting crude 2-(4-acetylthio-3-methyl-2-oxoazetidin-1-yl)-2-chloroacetic acid p-nitrobenzyl ester is dissolved in 175 ml of absolute dioxan, 13.5 g of poly-Hünig base are added, then 4.2 mg of triphenylphosphine, and the mixture is stirred for 15 hours at 50° under nitrogen. The poly-Hünig base is filtered off, washed with dioxan and the filtrate and washing liquid are together concentrated by evaporation in vacuo. The residue is chromatographed over silica gel with toluene-/ethyl acetate and yields the trans-title compound with the following physico-chemical properties:

TLC: $R_f=0.24$ (toluene/ethyl acetate 2:3); IR spectrum ($CH_2Cl_2$) absorption bands at 5.67, 5.9, 6.15, 6.55, 7.4 and 9.0μ.

EXAMPLE 10

2,6-dimethyl-2-penem-3-carboxylic acid p-nitrobenzyl ester (racemic trans-compound)

A catalytic amount of p-hydroxyquinone is added to a solution of 363 mg of 2-(4-acetylthio-3-methyl-2-oxoazetidin-1-yl)-3-triphenylphospohoranylideneacetic acid p-nitrobenzyl ester (racemic trans-compound) in 180 ml of absolute toluene and the mixture is stirred under nitrogen for 48 hours at 90°. The solvent is evaporated off in vacuo and the residue is chromatographed over 20 g of silica gel with toluene/ethyl acetate (19:1). The trans-title compound is obtained in the form of yellowish crystals having a melting point of 141°–143° and the following physico-chemical properties:

TLC: $R_f=0.6$ (toluene/ethyl acetate 2:3); IR spectrum ($CH_2Cl_2$) absorption bands at 3.4, 5.57, 5.82, 6.27, 6.55, 7.4, 7.6, 8.3 and 9.22μ; NMR spectrum (in $CDCl_3$/100 Mc, in ppm): 8.25–8.15, 2H, m; 7.65–7.56, 2H, m; 5.55–5.12, 3H, m+d (J=1.5 Hz); 3.9–3.6 1H, m; 2.36, 3H, s: 1.5, 3H, d.

EXAMPLE 11

2,6-dimethyl-2-penem-3-carboxylic acid (racemic trans-compound)

3 ml of 0.2N aqueous sodium bicarbonate solution and 150 mg of 10% palladiun/carbon catalyst are added to a solution of 80 mg (0.24 mmole) of 2,3-dimethyl-2-penem-3-carboxylic acid p-nitrobenzyl ester (racemic trans-compound) in 5 ml of absolute ethyl acetate, and the mixture is stirred at normal pressure for 50 minutes under hydrogen. The catalyst is filtered off from the hydrogenated mixture over diatomaceous earth and washed with 0.2N sodium bicarbonate solution and several times with ethyl acetate. The aqueous phase is washed with methylene chloride, acidified with 5% aqueous citric acid solution and exhaustively extracted with methylene chloride. The combined organic phases are dried over sodium sulphate, filtered, concentrated by evaporation in vacuo and dried in a high vacuum. The resulting title compound has the following physico-chemical properties:

Melting Point 119° (decomposition): TLC: $R_f=0.3$ (toluene/ethyl acetate/acetic acid 60:40:5); IR spectrum (KBr): absorption bands at 3.3–3.5, 5.62, 6.0, 6.35, 6.95, 7.55 and 7.85μ; NMR spectrum (DMSO d6/100 Mc, in ppm): 5.38, 1H, d, (J=1.5 Hz); 3.7, 1H, m: 3.4, 1H, m (exchange with $D_2O$); 2.28, 3H, s; 1.34, 3H, d.

EXAMPLE 12

4-acetylthio-3-isopropyl-2-oxoazetidine (racemic trans-compound)

A solution of 0.52 ml of thioacetic acid in 7 ml of 1N sodium hydroxide solution is added dropwise at room temperature under a nitrogen atmosphere to a solution of 750 mg (4.38 mmole) of 4-acetoxy-3-isopropylazetidin-2-one (racemic mixture of cis- and trans-isomer in the ratio of 1:3) in 3.6 ml of water and 0.9 ml of acetone and the mixture is stirred at the same temperature for 75 minutes. The reaction mixture is exhaustively extracted with methylene chloride. The combined organic phases are dried over sodium sulphate and concentrated by evaporation in vacuo. The residue is chromatographed over 40 g of silica gel with toluene/ethyl acetate (4:1) and yields the trans-title compound.

TLC: $R_f=0.4$ (toluene/ethyl acetate 2:3); IR spectrum ($CH_2Cl_2$): absorption bands at 2.95, 3.37, 5.62, 5.87 and 8.8μ. NMR spectrum (in $CDCl_3$/100 Mc, in ppm): 6.35, 1H, m (exchange with $D_2O$); 5.04, 1H, d (J=2.5 Hz); 3.0, 1H, m; 2.37, 3H, s; 2.1, 1H, m; 1.05, 3H, m.

The starting material is produced as follows: (a) A mixture of 172.28 g (216.5 ml, 2 mole) of isovaleraldehyde, 306 g (283 ml) of acetic anhydride and 24 g of freshly molten potassium acetate is refluxed for 17 hours. The cooled mixture is washed with 5% sodium carbonate solution until the organic phase reacts neutrally. After washing with water and drying over magnesium sulphate the oil obtained is distilled. 3-methyl-but-1-enyl acetate (cis-trans mixture 1:4) having a boiling point of 135°–140°/760 mmHg is obtained. (b) A solution of 8.72 ml of N-chlorosulphonyl isocyanate in 10 ml of absolute methylene chloride is added dropwise to a solution of 12.8 g (0.1 mole) of 3-methylbut-1-enyl acetate (cis-trans mixture 1:4) in 40 ml of absolute methylene chloride at room temperature under nitrogen. After 4 hours the reaction mixture is slowly poured into a mixture of 10 ml of water, 45 g of ice, 24 g of sodium bicarbonate and 8.3 g of sodium sulphite, the temperature being maintained between 0° and 5° by the occasional addition of ice. After approximately 30 minutes the organic phase reacts neutrally, whereupon it is separated off. The aqueous phase is extracted with methylene chloride. The organic phases are combined, dried over sodium sulphate and concentrated by evaporation in vacuo. The residue is chromatographed over silica gel with toluene/ethyl acetate and yields a cis-trans mixture of 4-acetoxy-3-isopropylazetidin-2-one in a ratio of approximately 1:3.

TLC: $R_f=0.3$ (toluene/ethyl acetate 2:3); IR spectrum (in methylene chloride): absorption bands at 2.95, 3.37, 5.6, 5.72, 7.32, 8.1, 9.7 and 10.2μ; NMR spectrum ($CDCl_3$/100 Mc, in ppm): 6.75, 1H, m (exchange with $D_2O$); 5.85, d, J=4.5 Hz (cis) and 5.6, d, J =1.5 Hz (trans), 1H; 3.03, 1H, m; 2.1, 3H, 2s; 2.3–1.8, 1H, m; 1.1, 6H, m.

EXAMPLE 13

2-(4-acetylthio-3-isopropyl-2-oxoazetidin-1-yl)-2-hydroxyacetic acid p-nitrobenzyl ester (racemic trans-compound)

1.9 g of 2-ethoxy-2-hydroxyacetic acid p-nitrobenzyl ester are added at room temperature to a solution of 616 mg (3.3 mmole) of 4-acetylthio-3-isopropyl-2-oxoazetidine (racemic trans-compound) in 48 ml of toluene and 10.5 ml of dimethylformamide. After adding freshly dried molecular sieves the mixture is stirred under nitrogen for 15 hours at room temperature and then for 2 hours at 50°. The molecular sieves are filtered off, washed with toluene and the filtrate and washing liquid are together concentrated by evaporation in vacuo. The residue is dried in a high vacuum and chromatographed over 60 g of silica gel with toluene/ethyl acetate (9:1). The two transisomers of the title compound, contaminated slightly by unreacted 2-ethoxy-2-hydroxyacetic acid p-nitrobenzyl ester, are obtained with the following physicochemical properties:

TLC: R$_f$=0.4 and 0.37 (toluene/ethyl acetate 2:3); IR spectrum (CH$_2$Cl$_2$): absorption bands at 5.62, 5.68, 6.55 and 7.42μ.

EXAMPLE 14

2-(4-acetylthio-3-isopropyl-2-oxoazetidin-1-yl)-2-triphenylphosphoranylideneacetic acid p-nitrobenzyl ester (racemic trans-compound)

(a) A solution of 1.175 g of 2-(4-acetylthio-3-isopropyl-2-oxoazetidin-1-yl)-2-hydroxyacetic acid p-nitrobenzyl ester (racemic trans-compound) in 21 ml of absolute dioxan is added to a solution of 3.8 g of poly-Hünig base in 10 ml of absolute dioxan that has already been stirred for 30 minutes. After the dropwise addition of a solution of 0.67 ml of thionyl chloride in 6.3 ml of absolute dioxan, the reaction mixture is stirred for 90 minutes at room temperature under nitrogen. The poly-Hünig base is filtered off, washed with dioxan and the filtrate is concentrated by evaporation in vacuo. The resulting crude 2-(4-acetylthio-3-isopropyl-2-oxoazetidin-1-yl)-2-chloroacetic acid p-nitrobenzyl ester (racemic trans-compound) can be used in the next step without further purification.

(b) The resulting crude 2-(4-acetylthio-3-isopropyl-2-oxoazetidin-1-yl)-2-chloroacetic acid p-nitrobenzyl ester is dissolved in 50 ml of absolute dioxan, 3.8 g of poly-Hünig base are added, the mixture is stirred for 30 minutes, then 1.18 g of triphenylphosphine are added and the mixture is stirred for 15 hours at 50° under nitrogen. The poly-Hünig base is filtered off, washed with dioxan and the filtrate and washing liquid are together concentrated by evaporation in vacuo. The residue is chromatographed over 60 g of silica gel with toluene/ethyl acetate 7:3 and yields the trans-title compound with the following physico-chemical properties:

TLC: R$_f$=0.25 (toluene/ethyl acetate 2:3); IR spectrum (CH$_2$Cl$_2$): absorption bands at 5.7, 5.9, 6.17, 6.55, 7.42 and 9.05μ.

EXAMPLE 15

2-methyl-6-isoprooyl-2-penem-3-carboxylic acid p-nitrobenzyl ester (racemic trans-compound)

A catalytic amount of p-hydroxyquinone is added to a solution of 660 mg of 2-(4-acetylthio-3-isopropyl -2-oxoazetidin-1-yl)-2-triphenylphosphoranylideneacetic acid p-nitrobenzyl ester (racemic trans-compound) in 300 ml of absolute toluene, and the mixture is stirred for 48 hours at 90° under nitrogen. The solvent is evaporated off in vacuo and the residue is chromatographed over 30 g of silica gel with toluene/ethyl acetate (19:1). The trans-title compound is obtained, by crystallisation from diethyl ether/methylene chloride, in the form of colourless crystals having the following -physico-chemical properties: melting point: 138°-139°; TLC: R$_f$=0.59 (toluene/ethyl acetate 2:3): IR spectrum (CH$_2$Cl$_2$) absorption bands at 5.57, 5.82, 6.27, 6.55, 7.4 and 7.6μ; NMR spectrum (in CDCl$_3$/100 Mc, in ppm): 8.3-8.2, 2H, m; 7.5-7.4, 2H, m1 5.75-5.1, 3H, m; 3.6-3.5, 1H, dd, J=8 and 1.5 Hz; 2.35, 3H, s; 1.07, 6H, m.

EXAMPLE 16

2-methyl-6-isopropyl-2-penem-3-carboxylic acid (racemic trans-compound)

4 ml of 0.2N aqueous sodium bicarbonate solution and 50 mg of 10% palladium/carbon catalyst are added to a solution of 100 mg of 2-methyl-6-isopropyl-2-penem-3-carboxylic acid p-nitrobenzyl ester (racemic trans-compound) in 7 ml of absolute ethyl acetate, and the mixture is stirred at normal pressure for 30 minutes under hydrogen. The catalyst is filtered off from the hydrogenated mixture over diatomaceous earth and washed with 0.2N sodium bicarbonate solution and several times with ethyl acetate. The aqueous phase is washed with methylene chloride, acidified with 5% aqueous citric acid solution and exhaustively extracted with methylene chloride. The combined organic phases are dried over sodium sulphate, filtered, concentrated by evaporation in vacuo and dried in a high vacuum. The resulting title compound has the following physico-chemical properties:

Melting Point 140°-143° (decomposition); TLC: R$_f$=0.37 (toluene/ethyl acetate/acetic acid 60:40:5); IR spectrum (KBr): absorption bands at 3.5, 5.62, 6.0, 6.35, 6.9, 7.52, 7.8 and 8.0μ; NMR spectrum (DMSO d6/100 Mc, in ppm): 5.52, 1H, d, J =1.5 Hz; 3.56, 1H+2 H$_2$O, dd, J=1.5 and 7.5 Hz; 2.26, 3H; s; 2.04, 1H, m; 1–0.9, 6H, m.

EXAMPLE 17

4-acetylthio-3-benzyl-2-oxoazetidine (racemic trans-compound)

A solution of 0.76 g (10 mmole) of thioacetic acid in 10 ml of 1N sodium hydroxide solution is added dropwise to a solution of 2.19 g (10 mmole) of 4-acetoxy-3-benzylazetidin-2-one (racemic mixture of cis- and trans-isomer in the ratio of 9:13) in 10 ml of dioxan at room temperature under a nitrogen atmosphere, and the mixture is stirred at the same temperature for 3 hours. The reaction mixture is exhaustively extracted with methylene chloride. The combined organic phases are dried over sodium sulphate and concentrated bv evaporation in vacuo. The residue is chromatogra.ohed over silica gel with toluene/ethyl acetate (9:1) and yields a cis-trans mixture of the title compound in the ratio of 2:10. By recrystallisation from methylene chloride/hexane at −10° the pure trans-compound having a melting point of 42°-43° is obtained.

TLC: R$_f$=0.52 (toluene/ethyl acetate 1:1); IR spectrum (CH$_2$Cl$_2$) absorption bands at 2.95, 5.65, 5.95, 7.40, 8.8 and 10.5μ; NMR spectrum (in CDCl$_3$/100 Mc, in ppm): 7.24, 5 H, m; 1 6.60, 1H, b; 4.99, 1H, d, J=2 Hz; 3.45, 1H, dq, J$_B$=8 Hz, J$_C$=6 Hz, J$_D$=2 Hz; 3.18, 1H, q, J$_A$=15 Hz, J$_C$=6 Hz; 3.00, 1H, q, J$_A$=15 Hz, J$_B$=8 Hz: 2.30, 3H, s.

The starting material is produced as follows (a) A mixture of 25 g (0.186 mole) of 3-phenylpropionaldehyde, 50 ml of acetic anhydride and 50 ml of pyridine is stirred for 15 hours at 100° and then concentrated by evaporation in a water jet vacuum. The residue is dissolved in methylene chloride, washed with 5% aqueous sodium bicarbonate solution and citric acid solution, dried over sodium sulphate and freed of solvent in vacuo. The residue is distilled in vacuo. 3-phenylprop-1-enyl acetate (cis-trans mixture 1:1) having a boiling point of 61°-65°/1 mm Hg is obtained.

(b) A mixture, prepared at 0°, of 17.6 g (0.1 mole) of 3-phenylprop-1-enyl acetate (cis-trans mixture 1:1) and 14.15 g (0.1 mmole) of N-chlorosulphonyl isocyanate is stirred for 6 hours at 10°-15°. The reaction mixture is diluted with 100 ml of cold methylene chloride and is slowly poured into a mixture of 10 ml of water, 45 g of ice, 24 g of sodium bicarbonate and 17 g of sodium sulphite. After filtering, the organic phase is separated off. The aqueous phase is extracted with methylene chloride. The organic phases are combined, dried over sodium sulphate and concentrated by evaporation in vacuo. The residue is chromatographed over silica gel with toluene/ethyl acetate 9:1 to 8:2, and yields a cis-trans mixture of 4-acetoxy-3-benzylazetidin-2-one in a ratio of 9:13.

TLC: $R_f$=0.5 (toluene/ethyl acetate 1:1); IR spectrum (in methylene chloride): absorption bands at 2.95, 5.6, 5.75, 7.35, 8.15, 8.65, 9.6, and 10.25µ; NMR spectrum (CDCl$_3$/100 Mc, in ppm): 2.04, s and 2.08, s, 3H; 2.95–3.15, 2H, m: 3.35–3.8 1H, m 5.50, 0.6 H, d, J=2 Hz (trans); 5.86, 0.4 H, d, J=4 Hz (cis); further signals at 6.80–7.45.

EXAMPLE 18

2-(4-acetylthio-3-benzyl-2-oxoazetidin-1-yl)-2-hydroxyacetic acid p-nitrobenzyl ester (racemic trans-compound)

2 g of 2-ethoxy-2-hydroxyacetic acid p-nitropenzyl ester are added at room temperature to a solution of 0.73 g (3.1 mmole) of 4-acetylthio-3-benzyl-3-oxoazetidine (racemic trans-compound) in 50 ml of toluene and 20 ml of dimethylformamide. After adding freshly dried molecular sieves, the mixture is stirred under nitrogen overnight at room temperature and then for 2 hours at 50°. The molecular sieves are filtered off, washed with toluene and the filtrate and washing liquid are together concentrated by evaporation in vacuo. The residue is dried in a high vacuum and chromatographed over silica gel with toluene/ethyl acetate (9:1 to 4:1). The two trans-isomers of the title compound, slightly contaminated with unreacted 2-ethoxy-2-hydroxyacetic acid p-nitrobenzyl ester, are obtained with the following physico-chemical properties: TLC: $R_f$=0.57 (toluene/ethyl acetate 1:1); IR spectrum (CH$_2$Cl$_2$): absorption bands at 2.85, 5.60, 5.70, 6.00, 6.20, 6.55, 7.40, 8.25, 9.00 and 11.75µ.

EXAMPLE 19

2-(4-acetylthio-3-benzyl-2-oxoazetidin-1-yl)-2-trichenylphosphoranylideneacetic acid p-nitrobenzyl ester (racemic trans-compound)

(a) 6 g of poly-Hünig base are added to a solution of 1.5 g of 2-(4-acetylthio-3-benzyl-2-oxoazetidin-1-yl)-2-hydroxyacetic acid p-nitrobenzyl ester (racemic trans-compound) in 20 ml of dry dioxan. After dropwise addition of a solution cf 1.5 ml of thionyl chloride in 10 ml of dioxan, the reaction mixture is stirred for 60 minutes at room temperature under nitrogen. The poly-Hünig base is filtered off, washed with dioxan and the filtrate is concentrated by evaporation in vacuo. The resulting crude 2-(4-acetylthio-3-benzyl-2-oxoazetidin-1-yl)-2-chloroacetic acid -p-nitrobenzyl ester (racemic trans-compound) can be used in the next step without further purification.

(b) The crude 2-(4-acetylthio-3-isopropyl-2-oxoazetidin-1-yl)-2-chloroacetic acid p-nitrobenzyl ester obtained is dissolved in 20 ml of dry dioxan, 6 g of poly-Hünig base are added, the mixture is stirred for 30 minutes, then 1.5 g of triphenylphosphine are added and the mixture is stirred overnight at 50° under nitrogen. The poly-Hünig base is filtered off, washed with dioxan and the filtrate and washing liquid are together concentrated by evaporation in vacuo. The residue is chromatographed over silica gel with toluene/ethyl acetate (9:1 to 1:1) and yields the trans-title compound with the following physico-chemical properties:

TLC: $R_f$=0.50 (toluene/ethyl acetate 1:1); IR spectrum (CH$_2$Cl$_2$): absorption bands at 5.7, 5.9, 6.2, 6.55, 7.00, 7.42, 9.05 and 11.75µ.

EXAMPLE 20

2-methyl-6-benzyl-2-penem-3-carboxylic acid p-nitrobenzyl ester (racemic trans-compound)

A catalytic amount of p-hydroxyquinone is added to a solution of 0.90 g (1.3 mmole) of 2-(4-acetylthio-3-benzyl-2-oxoazetidin-1-yl)-2-triphenylphosphoranylideneacetic acid p-nitrobenzyl ester (racemic trans-compound) in 50 ml of dry toluene and the mixture is stirred under nitrogen for 2 days at 90°. The solvent is evaporated off in vacuo and the residue is chromatographed over silica gel with toluene/ethyl acetate (9:1). The trans-title compound is obtained by crystallisation from methylene chloride/diethyl ether and has the following physico-chemical properties:

Melting Point: 182°–183°; TLC: $R_f$=0.85 (toluene/ethyl acetate 1:1): IR spectrum (CH$_2$Cl$_2$): absorption bands at 5.60, 5.85, 6.30, 6.55, 7.4, 7.6, 8.25, 8.55, 9.25 and 11.70µ; NMR spectrum (CDCl$_3$/100 Mc, in ppm): 2.36, 3H, s; 3.12, 1H, dd, $J_A$=14 Hz, $J_B$=9 Hz, 3.34, 1H, dd, $J_A$=14 Hz, $J_C$=6 Hz; 4.03, 1H, dq, $J_B$=9 Hz, $J_C$=6 Hz, $J_D$=2 Hz: 5.40, 1H, d, $J_D$=2 Hz; 5.25, 1H, d, J =14 Hz; 5.45, 1H, d, J =14 Hz; 7.30, 5H, m; 7.66, 2H, d, J=9 Hz; 8.27, 2H, d, J=9 Hz.

EXAMPLE 21

2-methyl-6-benzyl-2-penem-3-carboxylic acid (racemic trans-compound)

8 ml of 0.2M aqueous sodium bicarbonate solution and 400 mg of 10% palladium/carbon catalyst are added to a solution of 200 mg of 2-methyl-6-benzyl-2-penem-3-carboxylic acid p-nitrobenzyl ester (racemic trans-compound) in 12 ml of absolute ethyl acetate and the mixture is stirred at normal pressure for 60 minutes under hydrogen. The catalyst is filtered off from the hydrogenated mixture over diatomaceous earth. The aqueous phase is separated off, acidified with 5% aqueous citric acid solution and exhaustively extracted with methylene chloride. The combined organic phases are dried over sodium sulphate, filtered, concentrated by evaporation in vacuo and dried in a high vacuum. The resulting title compound has the following physico-chemical properties:

TLC: $R_f$=0.31 (toluene/ethyl acetate/acetic acid 60:40:5);IR spectrum (KBr): absorption bands at 3.20–4.30 b, 5.65, 6.0, 6.35, 6.9, 7.5, 7.9 and 8.2µ.

EXAMPLE 22:

4-ethylthiothiocarbonylthio-3-isopropyl-2-oxoazetidine (racemic trans-compound)

A solution of 230 mg of potassium ethyl trithiocarbonate in 1.5 ml of water is added dropwise at room temperature, in a nitrogen atmosphere, to a solution of 195 mg (1.14 mmole) of 4-acetoxy-3-isopropylazetidin-2-one (racemic mixture of cis- and trans-isomer in the ratio of 1:3) in 1 ml of water and 0.2 ml of acetone and the mixture is stirred at the same temperature for 120 minutes. The reaction mixture is exhaustively extracted with methylene chloride. The combined organic phases are dried over sodium sulphate and concentrated by evaporation in vacuo. The residue is chromatographed over 12 g of silica gel with toluene/ethyl acetate (9:1) and yields the trans-title compound. Melting point:

65°–66° TLC: $R_f=0.5$ (toluene/ethyl acetate 2:3]; IR spectrum (CH$_2$Cl$_2$): absorption bands at 2.95, 3.37, 5.62 and 9.25µ. NMR spectrum (in CDCl$_3$/100 Mc, in ppm): 6.65, 1H, m (exchange with D$_2$O); 5.4, 1H, d (J=2.5 Hz): 3.39, 2H, q; 3.05, 1H, m; 2.15, 1H, m: 1.38, 3H, t; 1.1, 6H, m.

EXAMPLE 23

2-(4-ethylthiothiocarbonylthio-3-isopropyl-2-oxoazetidin-1-yl)-2-hydroxyacetic acid p-nitrobenzyl ester (racemic trans-compound)

311 mg of 2-ethoxy-2-hydroxyacetic acid p-nitrobenzyl ester are added at room temperature to a solution of 137 mg (0.55 mmole) of 4-ethylthiothiocarbonyltho-3-isopropyl-2-oxoazetidine (racemic trans-compound) in 8 ml of toluene and 2 ml of dimethylformanide. After adding freshly dried molecular sieves, the mixture is stirred under nitrogen for 15 hours at room temperature and then for 2 hours at 50°. The molecular sieves are filtered off, washed with toluene and the filtrate and washing liquid are together concentrated by evaporation in vacuo. The residue is dried in a high vacuum and chromatographed over 80 g of silica gel with toluene/ethyl acetate (9:1). The two trans-isomers of the title compound, contaminated slightly by unreacted 2-ethoxy-2-hydroxyacetic acid p-nitrobenzyl ester are obtained with the following physico-chemical properties:

TLC: $R_f=0.4$ (toluene/ethyl acetate 2:3]; IR spectrum (CH$_2$Cl$_2$): absorption bands at 5.62, 5.7, 6.55, 7.42, 8.2 and 9.2µ.

EXAMPLE 24

2-(4-ethylthiothiocarbonylthio-3-isopropyl-2-oxoazetidin-1-yl)-2-triphenylphosohoranylideneacetic acid p-nitrobenzyl ester (racemic transcompound)

A solution of 606 mg of 2-(4-ethylthiothiocarbonylthio-3-isopropyl-2-oxoazetidin-1-yl)-2-hydroxyacetic acid p-nitrobenzyl ester (racemic trans-compound) in 6 ml of absolute tetrahydrofuran is cooled to −15°, while stirring 0.16 ml (2.23 mmole) of thionyl chloride and then, slowly, a solution of 0.31 ml of triethylamine in 0.3 ml of absolute tetrahydrofuran are added. The reaction mixture is stirred for 1 hour at 0°, 30 ml of cold methylene chloride are added and the mixture is washed with ice-cold 2N hydrochloric acid. The organic phase is washed with water until there is neutral reaction, then is dried with sodium sulphate and concentrated by evaporation in vacuo. The resulting crude 2-(4-ethylthiothiocarbonylthio-3-isopropyl-2-oxoazetidin-1-yl)-2-chloroacetic acid p-nitrobenzyl ester is dissolved in 1.5 ml of dry tetrahydrofuran, 0.71 g of triphenylphosphine is added and the mixture is stirred overnight at room temperature under a nitrogen atomsphere. The reaction mixture is diluted with methylene chloride, washed in succession with saturated aqueous sodium bicarbonate solution and water, dried over sodium sulphate and concentrated by evaporation in vacuo. The residue yields the title compound by chromatography over silica gel with toluene/ethyl acetate (9:1).

TLC: $R_f=0.5$ (toluene/ethyl acetate 2:3]; IR spectrum (CH$_2$Cl$_2$): absorption bands at 3.4, 5.7, 6.15, 6.55, 7.45, 9.05 and 9.25µ.

EXAMPLE 25

2-ethylthio-6-isopropyl-2-penem-3-carboxylic acid p-nitrobenzyl ester (racemic transcompound)

A catalytic amount of p-hydroxyquinone is added to a solution of 600 mg (0.855 mmole) of 2-(4-ethylthiothiocarbonylthio-3-isopropyl-2-oxoazetidin-1-yl)-2-triphenylphosphoranylideneacetic acid p-nitrobenzyl ester (racemic trans-compound) in 250 ml of absolute o-xylene and the mixture is stirred under reflux in a nitrogen atmosphere for 48 hours. The solvent is evaporated off in vacuo and the residue is chromatographed over 35 g of silica gel with toluene/ethyl acetate (19:1). The trans-title compound is obtained in the form of colourless crystals by crystallisation from diethyl ether/methylene chloride;

TLC: $R_f=0.62$ (toluene/ethyl acetate 2:3]; IR spectrum, (CH$_2$Cl$_2$): absorption bands at 5.57, 5.9, 6.55, 7.4 and 7.52µ.

EXAMPLE 26

2-ethylthio-6-isopropyl-2-penem-3-carboxylic acid (racemic trans-compound)

4 ml of 0.2N aqueous sodium bicarbonate solution and 150 mg of 10% palladium/carbon catalyst are added to a solution of 100 mg of 2-ethylthio-6-isopropyl-2-penem-3-carboxylic acid p-nitrobenzyl ester (racemic trans-compound) in 6 ml of absolute ethyl acetate and the mixture is stirred at normal pressure for 240 minutes under hydrogen. The catalyst is filtered off from the hydrogenated mixture over diatomaceous earth, then washed once with 0.2N sodium bicarbonate solution and several times with ethyl acetate. The aqueous phase is washed with methylene chloride, acidified with 5% aqueous citric acid solution and exhaustively extracted with methylene chloride. The combined organic phases are dried over sodium sulphate, filtered, concentrated by evaporation in vacuo and dried in a high vacuum. The resulting title compound has the following physicochemical properties:

TLC: $R_f=0.35$ (toluene/ethyl acetate/acetic acid 60:40:5); IR spectrum (KBr): absorption bands at 3.5, 5.62, 6.0, 6.75, 6.9, 7.52, 7.9, 8.15 and 8.9µ.

EXAMPLE 27

6-diazopenicillanic acid methyl ester

Analogously to German Offenlegungsschrift No. 2 305 972, 1.01 g of crude 6β-(N-nitroso)phenoxyacetamidopenicillanic acid methyl ester (produced according to U.S. Pat. No. 3,880,837) are dissolved at room temperature in 75 ml of absolute chloroform and after adding 200 ml of saturated aqueous sodium bicarbonate solution the mixture is stirred for 9 hours at a temperature of between 10 and 20°. The chloroform solution is separated off, washed with water and dried over sodium sulphate. After evaporating off the solvent in vacuo at room temperature, the crude diazo compound is obtained in the form of an oil. It can be used in the next reaction without further purification.

IR spectrum (in methylene chloride): characteristic absorption bands at 3.40, 4.80, 5.55, 5.70, 6.23, 6.50, 6.68, 7.75, 8.22, 8.85, 10.6 and 11.42µ.

EXAMPLE 28

6α-methoxypenicillanic acid methyl ester 5 ml of methanol and a few drops of 30% aqueous perchloric acid are added to a solution of 2 g of crude 6-diazopenicillanic acid methyl ester in 15 ml of absolute methylene chloride and the mixture is stirred for 15 minutes at room temperature. The reaction mixture is diluted with 30 ml of methylene chloride and washed in succession with aqueous sodium bicarbonate solution, water and sodium chloride solution, dried over sodium sulphate and concentrated by evaporation in vacuo. The residue is chromatographed over silica gel with toluene/ethyl acetate (9:1 and 4:1) and yields the slightly contaminated title compound.

IR spectrum (in methylene chloride): characteristic bands at 3.40, 5.63, 5.70, 6.90, 7.30, 7.68, 8.25, 8.47, 8.90, 9.15, 9.70 and 9.86μ.

EXAMPLE 29

6α-methoxypenicillanic acid methyl ester 1-oxide

A solution of 473 mg of 6α-methoxypenicillanic acid methyl ester in 10 ml of methylene chloride is cooled to 0°, 334 mg of m-chloroperbenzoic acid are added and the resulting suspension is stirred for 1 hour at the same temperature. The reaction mixture is diluted with 50 ml of methylene chloride, washed twice with aqueous sodium bicarbonate solution and with water, and dried over sodium sulphate. The solvent is evaporated off in vacuo and the residue is chromatographed over silica gel. With toluene/ethyl acetate (9:1 and 4:1) the title compound is obtained in the form of a white powder. An analytical sample is recrystallised from methylene chloride/diethyl ether/pentane and has the following physico-chemical properties:

Mp. 121°; $\alpha_D = +281° \pm 1°$; IR spectrum (in methylene chloride): characteristic absorption bands at 3.40, 5.58, 5.70, 6.85, 6.97, 7.75, 8.20, 8.90 and 9.45μ.

EXAMPLE 30

2-[(3S,4R)-4-(benzthiazol-2-yldithio)-3-methoxy-2-oxoazetidin-1-yl]-3-methylenebutyric acid methyl ester A solution of 307 mg of 6α-methoxypenicillanic acid methyl ester 1-oxide is dissolved in 10 ml of toluene, 196.57 mg of 2-mercaptobenzthiazole are added and the mixture is refluxed for 90 minutes. The solvent is distilled off in vacuo and the residue is chromatographed over silica gel. By elution with toluene/ethyl acetate (9:1) the title compound is obtained in the form of a colourless oil. IR spectrum (in methylene chloride): characteristic bands at 3.40, 5.62, 5.72, 6.68, 6.85, 7.02, 7.25, 7.50, 8.10, 8.20, 8.60, 8.95, 9.55, 9.92 and 10.92μ.

EXAMPLE 31

2-[(3S,4R)-4-(benzthiazol-2-yldithio)-3-methoxv-2-oxoazetidin-1-yl]-3-methylcrotonic acid methyl ester 0.1 ml of triethylamine is added to a solution of 432 mg of 2-[(3S,4R)-4-(benzthiazol-2-yldithio)-3-methoxy-2-oxoazetidin-1-yl]-3-methylenebutyric acid methyl ester in 25 ml of methylene chloride and the mixture is stirred at room temperature for 100 minutes. The reaction mixture is diluted with methylene chloride, washed twice with aqueous citric acid solution and water, dried over sodiun sulphate and freed of solvent in vacuo. The residue is purified by chromatography over silica gel with toluene/ethyl acetate (9:1 and 4:1) and yields the title compound in the form of an oil.

IR spectrum (in methylene chloride): characteristic absorption bands at 3.40, 5.63, 5.78, 6.85, 7.03, 7.23, 7.32, 7.70, 8.15, 8.87, 9.00, 9.25 and 9.92μ.

EXAMPLE 32

2-[(3S,4R)-4-acetylthio-3-methoxy-2-oxoazetidin-1-yl]-3-methylcrotonic acid methyl ester A solution of 372 mg of 2-[(3S,4R)-4-(benzthiazol-2-yldithio)-3-methoxy-2-oxoazetidin-1-yl]-3-methylcrotonic acid methyl ester in 10 ml of dimethylformamide is cooled to −20°, 10 ml of a solution of 2 g of sodium borohydride in 200 ml of dimethylformamide are added and the mixture is stirred at the same temperature for 30 minutes. 5 ml of freshly distilled acetyl bromide are added to the reaction mixture and the mixture is further stirred for 110 minutes at 0°. After adding 150 ml of benzene, the reaction mixture is washed in succession with sodium bicarbonate solution and water, dried over sodium sulphate and concentrated by evaporation in vacuo. The residue yields, after chromatography over silica gel with toluene/ethyl acetate (9:1), the title compound in the form of a slightly yellowish oil.

IR spectrum (in methylene chloride): characteristic absorption bands at 3.40, 5.63, 5.77, 5.83, 6.10, 6.95, 7.20, 7.30, 7.70, 8.12, 8.90, 9.20, 9.90, 10.20, 10.50 and 11.83μ.

Example 33

2-[(3S,4R)-4-acetylthio-3-methoxy-2-oxoazetidin-1-yl-2-oxoacetic acid methyl ester 3 equivalents of ozone are conveyed through a solution, cooled to −30°, of 87 mg (0.31 mmole) of 2-[(3S,4R)-4-acetylthio-3-methoxy-2-oxoazetidin-1-yl]-3-methylcrotonic acid methyl ester in 5 ml of ethyl acetate. The reaction mixture is diluted with 30 ml of methylene chloride and is shaken for 2 minutes with a 10% aqueous sodium bisulphite solution. The organic phase is separated off, washed with saturated sodium chloride solution, dried over sodium sulphate and concentrated by evaporation in vacuo.

IR spectrum of the resulting oily title compound (in methylene chloride): characteristic bands at 3.40, 5.47, 5.67, 5.82, 6.97, 7.33, 8.10, 8.92, 9.88 and 10.40μ. The resulting product can be used in the next step without further purification.

EXAMPLE 34

(3S,4R)-4-acetylthio-3-methoxy-2-oxoazetidine

A solution of 71.20 mg of 2[(3S,4R)-4-acetylthio-3-methoxy-2-oxoazetidin-1-yl-2-oxoacetic acid methyl ester (crude product) in 10 ml of 1% aqueous methanol is stirred overnight at room temperature. The reaction mixture is diluted with methylene chloride, washed with water, dried over sodium sulphate and concentrated by evaporation in vacuo. The residue is chromatographed over silica gel with toluene/ethyl acetate (9:1) and yields the title compound.

IR spectrum (in methylene chloride): characteristic absorption bands at 2.95, 3.40, 5.60, 5.88, 7.00, 7.37, 7.52, 8.25, 8.70, 8.85, 10.5 and 12.15μ.

EXAMPLE 35

2-[(3S,4R)-4-acetylthio-3-methoxy-2-oxoazetidin-1-yl]-2-hydroxyacetic acid p-nitrobenzyl ester 714 mg of 2-ethoxy-2-hydroxyacetic acid p-nitrobenzyl ester and 4 g of molecular sieve A4 are added to a solution of 245 mg of (3S,4R)-4-acetylthio-3-methoxy-2-oxoazetidine in a mixture of 8 ml of toluene and 2 ml of dimethylformamide and the mixture is stirred overnight at room temperature. The molecular sieves are filtered off from the mixture and the filtrate is concentrated by evaporation in vacuo. The residue is chromatographed over silica gel, and by elution with toluene/ethyl acetate (9:1 and 4:1) the title compound, contaminated with some glyoxylate, is obtained.

EXAMPLE 36

2-[(3S,4R)-4-acetylthio-3-methoxy-2-oxoazetidin-1-yl]-2-triphenylphosphoranylideneacetic acid p-nitrobenzyl ester (a) A suspension of 2 g of poly-Hünig base in 8 ml of dioxan is stirred for 30 minutes at room temperature, 832 mg of 2-[(3S,4R)-4-acetylthio-3-methoxy-2-oxoazetidin-1-yl]-2-hydroxyacetic acid p-nitrobenzyl ester dissolved in 12 ml of dioxan are added and then slowly a solution of 0.54 ml of thionyl chloride in 10 ml of dioxan is added. The mixture is stirred for 2 hours at room temperature, the poly-Hünig base is filtered off and the filtrate is concentrated by evaporation in vacuo. The residue is purified by chromatography over silica gel with toluene/ethyl acetate (1:1) and yields the 2-[(3S,4R)-4-acetylthio-3-methoxy-2-oxoazetidin-1-yl]-2-chloroacetic acid p-nitrobenzyl ester in crude form.

(b) 812 mg of triphenylphosphine and 3 g of poly-Hünig base are added to a solution of 833 mg of 2-[(3S,4R)-4-acetylthio-3-methoxy-2-oxoazetidin-1-yl]-2-chloroacetic acid p-nitrobenzyl ester in 50 ml of dioxan and the mixture is stirred overnight at 50°. The poly-Hünig base is removed by filtration and the filtrate is concentrated by evaporation in vacuo. The residue is chromatographed over silica gel with toluene/ethyl acetate (9:1, 4:1 and 1:1) and yields the title comcound.

IR spectrum (in methylene chloride): characteristic absorption bands at 3.40, 5.67, 5.85, 6.15, 6.55, 6.97, 7.42, 8.0 and 9.03$\mu$.

EXAMPLE 37

(5R,6S)-2-methyl-6-methoxy-2-penem-3-carboxylic acid p-nitrobenzyl ester

A catalytic amount of hydroquinone is added to a solution of 244 mg of 2-[(3S,4R)-4-acetylthio-3-methoxy-2-oxoazetidin-1-yl]-2-triphenylphosphoranylideneacetic acid p-nitrobenzyl ester in 100 ml of absolute toluene and the mixture is stirred for 32 hours at 90° under nitrogen. The toluene is evaporated off in vacuo and the residue is chromatographed over silica gel with toluene/ethyl acetate (19:1). The title compound is obtained in the form of a solid white substance.

IR spectrum (in methylene chloride): characteristic absorption bands at 3.40, 5.55, 6.30, 6.55, 7.03, 7.42, 7.60, 8.20, 8.42, 8.60, 8.90, 9.20, 9.60 and 11.7$\mu$; NMR spectrum (CDCl$_3$/100 Mc, in ppm): 8.22, 2H, d, J=8 Hz; 7.64, 2H, d, J=8 Hz; 5.53, 1H, d, J=2 Hz; 5.35, 2H, AB; 4.91, 1H, d, J=2 Hz; 3.57, 3H, s; 2.37, 3H, s.

EXAMPLE 38

(5R,6S)-2-methyl-6-methoxy-2-penem-3-carboxylic acid 75 mg of 10% palladium/carbon catalyst are added to a solution of 34 mg of (5R,6S)-2-methyl-6-methoxy-2-penem-3-carboxylic acid p-nitrobenzyl ester in a mixture of 2 ml of ethyl acetate and 2 ml of 2M sodium bicarbonate solution, and the mixture is hydrogenated at room temperature for 1.5 hours under atmospheric pressure. The hydrogenated mixture is filtered through diatomaceous earth and the filter residue is washed with 1 ml of 2M aqueous sodium bicarbonate solution and ethyl acetate. The aqueous phase is separated off from the filtrate, acidified with 0.1M aqueous citric acid and extracted several times with methylene chloride. The combined methylene chloride extracts are dried over sodium sulphate and concentrated by evaporation in vacuo.

IR spectrum (in methylene chloride) of the resulting crude title compound: characteristic absorption bands at 3.40, 5.57, 5.80, 5.95, 6.30, 7.00, 8.20 and 9.90$\mu$.

EXAMPLE 39

6$\alpha$-phenoxyacetoxypenicillanic acid methyl ester

Analogously to D. Hauser and H. P. Sigg, Helv. Chim. Acta 50, 1327 (1967), a solution of 7.4 g (20.3 mmole) of 6$\beta$-(N-nitroso)-phenoxyacetamidopenicillanic acid methyl ester (crude product according to U.S. Pat. No. 3,880,837) in 100 ml of benzene is stirred for 3 hours at 50° in a nitrogen atmosphere. The solvent is evaporated off in vacuo and the residue is chromatographed over silica gel with toluene/ethyl acetate (9:1). The resulting oily product is recrystallised from diethyl ether/hexane and yields the title compound having a melting point of 71°; $\alpha_D$=114'±1° (CHCl$_3$); IR spectrum (in methylene chloride): characteristic absorption bands at 3.4, 5.6, 5.7, 6.25, 6.69, 7.17, 8.26, 8.55, 9.05 and 9.18$\mu$.

EXAMPLE 40: 6$\alpha$-phenoxyacetoxypenicillanic acid methyl ester 1-oxide 1.1 g (1 equivalent) of 50% m-chloroperbenzoic acid are added in portions at 0° to a solution of 1.16 g (3.18 mmole) of 6$\alpha$-phenoxyacetoxypenicillanic acid methyl ester in 30 ml of absolute methylene chloride. After addition is complete, the reaction mixture is stirred for 30 minutes at 0°, then diluted with methylene chloride, washed in succession with aqueous sodium bicarbonate solution, water and sodium chloride solution, and dried over sodium sulphate. After evaporating off the solvent the residue is chromatographed over silica gel with toluene/ethyl acetate (4:1). The title compound is obtained in the form of a foam;

TLC: Rf=0.24 (toluene/ethyl acetate 1:1), IR spectrum (in methylene chloride): characteristic absorption bands at 3.33, 3.41, 5.57, 5.72, 6.27, 6.72, 7.0, 8.25, 8.6, 9.21 and 9.46$\mu$.

EXAMPLE 41:

2-[(3S,4R)-4-(benzthiazol-2-yldithio)-3-phenoxyacetoxy-2-oxoazetidin-1-yl]-3-methylenebutyric acid methyl ester A solution of 1.01 (2.65 mmole) of 6$\alpha$-phenoxyacetoxypenicillanic acid methyl ester 1-oxide is dissolved in 30 ml of toluene, 445 mg (2.65 mmole) of 2-mercaptobenzthiazole are added and the mixture is refluxed for 60 minutes in a nitrogen atmosphere, The solvent is distilled off in vacuo and the residue is chromatographed over silica gel. By eluting with toluene-/ethyl acetate (19:1) the title compound is obtained in the form of a faintish brown oil.

IR spectrum (in methylene chloride): characteristic bands at 3.45, 5.62, 5.75, 6.27, 6.71, 6.89, 7.05, 7.30, 7.54, 7.68, 8.15, 8.55, 9.15, 9.35 and 9.95μ; TLC: Rf=0.63 (toluene/ethyl acetate 1:1).

EXAMPLE 42:

2[(3S,4R)-4-(benzthiazol-2-yldithio)-3-phenoxyacetoxy-2-oxoazetidin-1-yl-3-methylcrotonic acid methyl ester 0.4 ml of triethylamine is added to a solution of 1.28 g (2.41 mmole) of 2-(3S,4R)-4-(benzthiazol-2-yldithio)-3-phenoxyacetoxy-2-oxoazetidin-1-yl-3-methylenebutyric acid methyl ester in 30 ml of methylene chloride and the mixture is stirred at room temperature for 30 minutes. The reaction mixture is diluted with 50 ml of methylene chloride, washed in succession with 2N hydrochloric acid, water and sodium chloride solution, dried over sodium sulphate and freed from solvent in vacuo. The residue is purified by chromatography over silica gel with toluene/ethyl acetate (19:1) and yields the title compound in the form of a faint yellow oil.

IR spectrum (in methylene chloride): characteristic absorption bands at 3.46, 5.69, 5.82, 5.90, 6.28, 6.73, 6.90, 7.06, 7.28, 7.38, 7.75, 8.20, 8.60, 9.27 and 9.96 μ; TLC : Rf=0.61 (toluene/ethyl acetate 1:1).

EXAMPLE 43:

2-[(3S,4R)-4-acetylthio-3-phenoxyacetoxy-2-oxoazetidin-1-yl-3-methylcrotonic acid methyl ester A solution of 687 mg (1.29 mmole) of 2-[(3S,4R)-4-(benzthiazol-2-yldithio)-3-phenoxyacetoxy-2oxoazetidin-1-yl]-3-methylcrotonic acid methyl ester in 14 ml of dimethylformamide is added to a solution, cooled to −20°, of 76 mg (2 mmole) of sodium borohydride in 10 ml of dimethylformamide and the mixture is stirred at the same temperature for 10 minutes. 7 ml of freshly distilled acetyl bromide are added to the reaction mixture, which is further stirred at 0° for 40 minutes. After adding 400 ml of benzene, the reaction mixture is washed in succession with aqueous sodium bicarbonate solution, water and sodium chloride solution, dried over sodium sulphate and concentrated by evaporation in vacuo. After chromatography over silica gel with toluene/ethyl acetate (19:1) the residue yields the title compound in the form of an oil, which is further purified on silica gel plates with toluene/ethyl acetate (4:1). The title compound is obtained in oily form.

IR spectrum (in methylene chloride): characteristic absorption bands at 3.45, 5.63, 5.83, 6.27, 6.70, 7.00, 7.25, 7.35, 8.15, 8.58, 8.93 and 9.20 μ; TLC: Rf=0.54 (toluene/ethyl acetate 1:1).

EXAMPLE 44:

2[-(3S,4R)-4-acetylthio-3-phenoxyacetoxy-2-oxoazetidin-1-yl]-2-oxoacetic acid methyl ester 4 equivalents of ozone are conveyed through a solution, cooled to −20°, of 170 mg (0.42 mmole) of 2-[(3S,4R)-4-acetylthio-3-phenoxyacetoxy-2-oxoazetidin1-yl]-3-methylcrotonic acid methyl ester in 5 ml of ethyl acetate. The reaction mixture is diluted with 5 ml of ethyl acetate, and shaken vigorously with a 10% aqueous sodium bisulphite solution. The organic phase is separated off, washed with water and saturated sodium chloride solution, dried over sodium sulphate and concentrated by evaporation in vacuo.

IR spectrum of the resulting oily title compound (in methylene chloride): characteristic bands at 3.38, 5.48, 5.63, 5.70, 5.83, 6.27, 6.70, 7.00, 7.40, 8.07, 8.25, 8.63 and 8.95 μ. The resulting product can be used in the next step without further purification.

EXAMPLE 45:

(3S,4R)-4-acetylthio-3-phenoxyacetoxy-2-oxoazetidine

A solution of 129 mg (0.34 mmole) of (3S,4R)-2-(4-acetylthio-3-phenoxyacetoxy-2-oxoazetidin-1-yl)-2-oxoacetic acid methyl ester (crude product) in 10 ml of 1% aqueous methanol is stirred for 4 hours at room temperature. The reaction mixture is diluted with 50 ml of methylene chloride, washed in succession with water and saturated sodium chloride solution, dried over sodium sulphate and concentrated by evaporation in vacuo. The residue is chromatographed over silica gel with toluene/ethyl acetate (9:1) and yields the title compound.

IR spectrum (in methylene chloride): characteristic bands at 2.95, 3.45, 5.55, 5.60, 5.88, 6.25, 6.68, 8.33 and 8.85 82 ; TLC: Rf=0.36 (toluene/ethyl acetate 1:1).

EXAMPLE 46:

2-[(3S,4R)-4-acetylthio-3-phenoxyacetoxy-2-oxoazetidin-1yl]-2-hydroxyacetic acid p-nitrobenzyl ester 760 mg of 2-ethoxy-2-hydroxyacetic acid p-nitrobenzyl ester and 4 g of molecular sieve A4 are added to a solution of 283 mg of (3S,4R)-4-acetylthio-3-methoxy-2-oxoazetidine in a mixture of 8 ml of toluene and 2 ml of dimethylformamide, and the mixture is stirred overnight at room temperature. The molecular sieves are filtered off from the mixture and the filtrate is concentrated by evaporation in vacuo. The residue is chromatographed over silica gel, and the title compound, contaminated with some glyoxylate, is obtained by eluting with toluene/ethyl acetate (9:1 and 4:1).

EXAMPLE 47:

2-[(3S,4R)-4-acetylthio-3-phenoxyacetoxy-2-oxoazetidin-1-yl]-2-triphenylphosphoranylideneacetic acid p-nitrobenzyl ester (a) A suspension of 2 g of poly-Hünig base in 8 ml of dioxan is stirred at room temperature for 30 minutes, a solution of 962 mg of 2- (3S,4R)-4-acetylthio-3-phenoxyacetoxy-2-oxoazetidin-1-yl-2-hydroxyacetic acid p-nitrobenzyl ester in 10 ml of dioxan is added, then a solution of 0.38 ml of thionyl chloride in 8 ml of dioxan is added slowly. The mixture is stirred for 2 hours at room temperature, the poly-Hünig base is filtered off and the filtrate is concentrated by evaporation in vacuo. The residue is purified by chromatography over silica gel with toluene/ethyl acetate (1:1) and yields the 2-[(3S,4R)-4-acetylthio-3-methoxy-2-oxoazetidin-1-yl]-2-chloroacetic acid p-nitrobenzyl ester in crude form.

(b) 786 mg of triphenylphosphine and 3 g of poly-Hünig base are added to a solution of 960 mg of 2-[(3S,4R)-4-acetylthio-3-phenoxyacetoxy-2-oxoazetidin-1-yl]-2-chloroacetic acid p-nitrobenzyl ester in 40 ml of dioxan and the mixture is stirred overnight at 50° under nitrogen. The poly-Hünig base is removed by filtration and the filtrate is concentrated by evaporation in vacuo. The residue is chromatographed over silica gel with toluene/ethyl acetate (9:1, 4:1 and 1:1) and yields the title compound. IR spectrum (in methylene chloride): characteristic absorption bands at 5.7, 5.9, 6.17, 6.55 and 7.45 μ.

EXAMPLE 48:

(5R,6S)-2-methyl-6-phenoxyacetoxy-2-penem-3-carboxylic acid p-nitrobenzyl ester

A catalytic amount of hydroquinone is added to a solution of 285 mg of 2-[(3S,4R)-4-acetylthio-3-phenoxyacetoxy-2-oxoazetidin-1-yl]-2-triphenylphosphoranylideneacetic acid p-nitrobenzyl ester in 100 ml of absolute toluene and the mixture is stirred under nitrogen for 35 hours at 90°. The toluene is evaporated off in vacuo and the residue is chromatographed over silica gel with toluene/ethyl acetate (19:1). The title compound is obtained in the form of an oil.

IR spectrum (in methylene chloride): characteristic absorption bands at 5.55, 6.30, 6.55 and 7.42 μ.

EXAMPLE 49:

(5R,6S)-2-methyl-6-phenoxyacetoxy-2-penem-3-carboxylic acid 75 mg of 10 % palladium/carbon catalyst are added to a solution of 45 mg of (5R,6S)-2-methyl-6-phenoxyacetoxy-2-penem-3-carboxylic acid p-nitrobenzyl ester in a mixture of 2 ml of ethyl acetate and 2 ml of 2M sodium bicarbonate solution, and the mixture is hydrogenated under atmospheric pressure for 1.5 hours at room temperature. The hydrogenated mixture is filtered through diatomaceous earth and the filter residue is washed with 1 ml of 2M aqueous sodium bicarbonate solution and methyl acetate. The aqueous phase is separated off from the filtrate, acidified with 0.1M aqueous citric acid and extracted several times with methylene chloride. The combined methylene chloride extracts are dried over sodium sulphate and concentrated by evaporation in vacuo.

IR spectrum (in ethanol) of the resulting crude title compound: characteristic absorption bands at 5.6 μ; UV spectrum (in ethanol): $\lambda_{max}=305$ nm.

EXAMPLE 50:

6α-methoxypenicillanic acid 2,2,2-trichloroethyl ester 1-oxide

A solution of 2 g of 6α-methoxypenicillanic acid 2,2,2-trichloroethyl ester (produced according to P. J. Giddins, D. I. Johns, E. J. Thomas: T. L. 11, 995, 1978) in 100 ml of methylene chloride and 0.3 ml of acetone is cooled to -15° C., 1 ml of 40% peracetic acid is added over the course of 5 minutes, and the mixture is stirred for 15 minutes at the same temperature. Subsequently 15 ml of a 0.1N sodium thiosulphate solution are added to the reaction mixture. The organic solution is separated off and washed twice with ice water. After drying over sodium sulphate the solvent is evaporated off in vacuo and the residue is recrystallised from ether/petroleum ether. The resulting compound has the following physico-chemical properties: Mp.=127°–128°. IR spectrum (in methylene chloride): characteristic absorption bands at 3.41, 5.58, 5.65, 8.33, 8.47, 8.70 and 9.48 μ.

EXAMPLE 51:

2-[(3S,4R)-4-(benzthiazol-2-yldithio)-3-methoxy-2-oxoazetidin-1-yl]-3-methylenebutyric acid 2,2,2-trichloroethyl ester 1.39 g of 2-mercaptobenzthiazol are added to a solution of 3 g of 6α-methoxypenicillanic acid 2,2,2-trichloroethyl ester 1-oxide in 40 ml of absolute toluene, and the mixture is refluxed for 105 minutes under nitrogen. The solvent is distilled off in vacuo and yields the title compound in the form of a yellowish oil.

IR spectrum (in methylene chloride): characteristic absorption bands at 3.39, 5.60, 5.65, 6.85, 8.20, 8.62, 8.97, 9.85 and 9.95 μ.

The resulting product can be used in the next step without further purification.

EXAMPLE 52:

2-[(3S,4R)-4-(benzthiazol-2-yldithio)-3-methoxy-2-oxoazetidin-1-yl]-3-methylcrotonic acid 2,2,2-trichloroethyl ester 0.78 ml of triethylamine is added to a solution of 4.17 g of 2- (3S,4R)-4-benzthiazol-2-yldithio)-3-methoxy-2-oxoazetidin-1-yl-3-methylenebutyric acid 2,2,2-trichloroethyl ester in 75 ml of absolute methylene chloride at 0° and the mixture is stirred at this temperature for 15 minutes.

The reaction mixture is washed in succession with 4N phosphoric acid, saturated aqueous sodium bicarbonate solution and sodium chloride solution, and dried over sodium sulphate. The solvent is evaporated off and the residue is purified by chromatography over silica gel with toluene and toluene/ethyl acetate (19:1). The title compound is obtained in the form of an oil. IR spectrum (in methylene chloride): characteristic absorption bands at 3.39, 5.62, 5.76, 6.85, 7.04, 7.25, 6.85, 9.01, 9.48, 9.85 and 9.95 μ.

EXAMPLE 53:

2-[(3S,4R)-4-acetylthio-3-methoxy-2-oxoazetidin-1-yl]-3-methylcrotonic acid 2,2,2-trichloroethyl ester A solution of 3.26 g of 2- (3S,4R)-4-(benzthiazol-2-yldithio]-3-methoxy-2-oxoazetidin-1-yl]-3-methyl-crotonic acid 2,2,2-trichloroethyl ester in 36.3 ml of acetic anhydride and 12.4 ml of acetic acid is cooled to −15° and 1.7 g of triphenylphosphine are added. After stirring under nitrogen at the same temperature for 75 minutes, 24.8 ml of pyridine are added to the mixture. After stirring for a further 3 hours at 0°, the reaction mixture is concentrated by evaporation under reduced pressure and the resulting residue is purified by chromatography over silica gel with toluene and toluene/ethyl acetate (19:1). IR spectrum (in methylene chloride): characteristic absorption bands at 3.40, 5.63, 5.77, 5.80, 6.13, 7.25, 7.35, 8.26, 9.0, 9.52 and 11.90 μ.

EXAMPLE 54:

2-[(3S,4R)-4-acetylthio-3-methoxy-2-oxoazetidin-1-yl]-2-oxoacetic acid 2,2,2-trichloroethyl ester 3 equivalents of ozone are conveyed through a solution, cooled to −30°, of 8.4 g of 2- [4R)-4-acetylthio-3-methoxy-2-oxoazetidin-1-yl]-3-methylcrotonic acid 2,2,2-trichloroethyl ester in 765 ml of methyl acetate. After treating with ozone, the reaction mixture is left to stand at the same temperature for 15 minutes and then the excess ozone is removed by a nitrogen current. The reaction mixture is washed at 0° with a 10% aqueous sodium bisulphite solution and then with sodium chloride solution. After separating off, the combined aqueous phases are extracted a further 4 times with methyl acetate. The combined methyl ester solutions are dried over sodium sulphate and concentrated by evaporation in vacuo.

IR spectrum of the resulting oily title compound (in methylene chloride): characteristic absorption bands at 3.39, 5.48, 5.63, 6.09, 6.94, 7.25, 7.38, 7.46, 8.23, 8.93, 9.90 and 11.83 μ.

EXAMPLE 55:

(3S,4R)-4-acetylthio-3-methoxy-2-oxoazetidine (a) A solution of 1.52 g of 2-[(3S,4R)-4-acetylthio-3-methoxy-2-oxoazetidin-1-yl]-2-oxoacetic acid 2,2,2-trichloroethyl ester (crude product) in 290 ml of methanol, 40 ml of methyl acetate and 5.9 ml of water is refluxed for 20 minutes under nitrogen. The solvent is evaporated off in vacuo. After chromatography over silica gel with toluene/ethyl acetate (3:1) the residue yields the title compound.

IR spectrum (in methylene chloride): characteristic absorption bands at 2.95, 3.40, 5.60, 5.88, 7.37, 7.52, 8.25, 8.70, 8.85, 10.5 and 12.12 μ.

The same compound may also be obtained as follows:

(b) 1.5 equivalents of an aqueous sodium thioacetate solution are added to a solution of 40 mg of (3S,4S)-4-acetoxy-3-methoxy-2-oxoazetidine (for manufacture see below) in 1.5 ml of phosphate buffer of a pH of 7 and 0.1 ml of dioxan, and the mixture is stirred for 30 minutes at room temperature. The reaction mixture is extracted with methylene chloride and the separated organic solution is then dried over sodium sulphate. The solvent is evaporated off in vacuo and the residue is purified by chromatography over silica gel with toluene/ethyl acetate (3:1). The IR spectrum of the resulting title compound (in methylene chloride) is identical to that of the product obtained according to a).

EXAMPLE 56:

2-[(3S,4R)-4-acetylthio-3-methoxy-2-oxoazetidin-1-yl]-2-hydroxyacetic acid p-nitrobenzyl ester 1.15 g of 2-ethoxy-2-hydroxyacetic acid p-nitrobenzyl ester and 4 g of molecular sieves A4are added to a solution of 350 mg of (3S,4R)-4-acetylthio-3-methoxy-2-oxoazetidine in a mixture of 24 ml of absolute toluene and 6 ml of absolute dimethylformamide and the mixture is stirred overnight at room temperature under nitrogen. The molecular sieves are filtered off and the filtrate is concentrated by evaporation in vacuo. The residue is chromatographed over silica gel, and the title compound is obtained by eluting with toluene and toluene/ethyl acetate (19:1).

IR spectrum (in methylene chloride): characteristic absorption bands at 2.86, 3.39, 5.60, 5.68, 5.88, 6.21, 6.56, 7.41, 8.26, 9.01 and 11.76 μ.

EXAMPLE 57:

2-[(3S,4R)-4-acetylthio-3-methoxy-2-oxoazetidin-1-yl]-2-chloroacetic acid p-nitrobenzyl ester A solution of 0.6 g of 2-[(3S,4R)-4-acetylthio-3-methoxy-2-oxoazetidin-1-yl]-2-hydroxyacetic acid p-nitrobenzyl ester in 7 ml of dry tetrahydrofuran is cooled to −15° and 0.19 ml of thionyl chloride is added. 0.37 ml of triethylamine in 0.4 ml of dry tetrahydrofuran is then added dropwise at the same temperature. The reaction mixture is stirred for 1 hour at 0°, diluted with cold methylene chloride and washed with an ice-cold 2N HCl solution. After extracting several times by shaking with water, the methylene chloride solution is dried over sodium sulphate and concentrated by evaporation.

IR spectrum (in methylene chloride): characteristic absorption bands at 3.41, 5.59, 5.65, 5.88, 6.21, 6.56, 7.41, 8.23, 8.55, 9.05, 10.5 and 11.76 μ.

EXAMPLE 58:

2-[(3S,4R)-4-acetylthio-3-methoxy-2-oxoazetidin-1-yl]2-trichenylphosphoranylideneacetic acid p-nitrobenzyl ester 0.84 g of triphenylphosphine is added to a solution of 0.63 g of 2-[(3S,4R)-4-acetylthio-3-methoxy-2-oxoazetidin-1-yl-2-chloroacetic acid p-nitrobenzyl ester in 1.8 ml of dry tetrahydrofuran, and the mixture is stirred overnight at room temperature under nitrogen. The mixture is diluted with methylene chloride and washed with a cold, saturated, aqueous sodium bicarbonate solution. Additional washing with water, drying over sodium sulphate and concentrating by evaporation in vacuo yield the crude title compound which is purified by chromatography over silica gel with toluene/ethyl acetate (19:1 to 3:1).

IR spectrum (in methylene chloride): characteristic absorption bands at 3.40, 5.67, 5.90, 6.20, 6.58, 7.46 and 9.05 μ.

EXAMPLE 59:

(5R,6S)-2-methyl-6-methoxy-2-penem-3-carboxylic acid p-nitrobenzyl ester

A catalytic amount of 3,5-di-tert.butyl-4-hydroxytoluene is added to a solution of 74 mg of 2-(3S-,4R)-4-acetylthio-3-methoxy-2-oxoazetidin-1-yl-2-tri-phenylphosphoranylideneacetic acid p-nitrobenzyl ester in 30 ml of absolute toluene and the mixture is refluxed under nitrogen for 3 hours. The toluene is evaporated off in vacuo and the residue is chromatographed over silica gel with toluene/ethyl acetate (19:1). The title compound is obtained in the solid state.

IR spectrum (in methylene chloride): characteristic absorption bands at 3.41, 5.60, 5.85, 6.63, 6.58, 7.41, 7.60, 8.23, 9.26 and 11.76 μ.

EXAMPLE 60:

3-ethyl-4-(2-acetylaminoethylthiothiocarbonylthio)-2-oxoazetidine (racemic cis-trans compound)

(a) A solution of 0.78 g (5 mmole) of 4-acetoxy-3-ethyl-azetidin-2-one (racemic mixture of cis- and trans-isomer in a ratio of 6:4) in 2 ml of dioxan is added dropwise under a nitrogen atmosphere to a solution of 1.175 g of potassium (2-acetylaminoethyl)trithiocarbonate in 20 ml of pre-cooled phosphate buffer of a pH of 7 and the mixture is stirred for 60 minutes. The reaction mixture is centrifuged, the supernatant clear solution is decanted off and the oily residue is taken up in methylene chloride. The organic phase is dried over sodium sulphate and concentrated by evaporation in vacuo. The residue is triturated once with diethyl ether and is further processed in this form.

TLC: $R_f$=0.16 (ethyl acetate); IR spectrum ($CH_2Cl_2$): absorption bands at 2.92, 2.97, 5.63, 5.97, 6.62, 9.35 and 12.34 μ.

The two starting materials may be produced as follows:

(b) 42.7 g (26.3 ml, 0.302 mole) of N-chlorosulphonyl isocyanate are added dropwise at −10° over the course of 30 minutes to a stirred solution of 34.5 g (0.302 mole) of but-1-enyl acetate in 35 ml of dry methylene chloride. After a further 4 hours of stirring at 0°, the reaction mixture is diluted with 50 ml of pre-cooled methylene chloride and added dropwise to a hydrolysing mixture of 32 ml of water, 144 g of ice, 113 g of sodium bicarbonate and 38.2 g of anhydrous sodium sulphite. During the hydrolysis the temperature is maintained at 0° by external cooling. When the organic phase no longer has an acidic reaction, the reaction mixture is diluted with 100 ml of diethyl ether and filtered through celite. The organic phase is separated off, the aqueous phase is extracted three times with 400 ml of diethyl ether, the organic phases are combined, dried and concentrated by evaporation in vacuo. The residue is chromatographed over silica gel with toluene/ethyl acetate (2:1) and yields a racemic mixture of cis- and trans-4-acetoxy-3-ethylazetidin-2-one in a ratio of 6:4 in oily form. IR spectrum ($CH_2Cl_2$): absorption bands at 2.94, 5.60, 5.75, 7.35, 8.06 and 8.85 μ.

(c) A solution of 1.708 g (14.35 mmole) of 2-acetylaminoethyl mercaptan in 2 ml of absolute ethanol is added dropwise over the course of 0.5 hours, while stirring and cooling to 10°–15°, to a solution of 0.80 g (14.35 mmole) of potassium hydroxide in 5 ml of absolute ethanol. After a further half hour, a solution of 1.09 g (14.35 mmole) of carbon disulphide in 3 ml of absolute ethanol is added, the temperature being maintained at 10°–15°. The reaction mixture is further stirred for 3 hours at room temperature and cooled in an ice bath for 20 minutes. The yellow crystalline precipitate is filtered off, washed once with absolute ethanol and yields potassium (2-acetylaminoethyl)-trithiocarbonate having a melting point of 171°–174°.

IR spectrum (KBr): absorption bands at 2.95, 6.18, 6.50, 7.00, 7.32, 7.43, 7.79, 8.33, 9.09 and 11.83 μ.

EXAMPLE 61:

2-[3-ethyl-4-(2-acetylaminoethylthiothiocarbonylthio)-2-oxoazetidin-1-yl]-2-hydroxyacetic acid p-nitrobenzyl ester (racemic cis-trans compound)

4.20 g (16.5 mmole) of 2-ethoxy-2-hydroxyacetic acid δ-nitrobenzyl ester are added at room temperature to a solution of 3.30 g (11 mmole) of 3-ethyl-4-(2-acetylaninoethylthiothiocarbonylthio-2-oxoazetidine (racemic cis-trans compound) in 120 ml of toluene and 32 ml of dimethylformamide. After adding freshly dried molecular sieves the mixture is stirred under nitrogen for 3 hours at room temperature. The molecular sieves are filtered off, washed with 20 ml of toluene and the filtrate and washing liquid are together concentrated by evaporation in vacuo. The residue is dried in a high vacuum and then triturated with diethyl ether to remove unreacted 2-ethoxy-2-hydroxyacetic acid p-nitrobenzyl ester. The title compound with the following physico-chemical properties is obtained:

TLC: $R_f$=0.16 (ethyl acetate); IR spectrum ($CH_2Cl_2$): absorption bands at 2.86, 2.92, 3.03, 5.65, 5.71, 5.97, 6.58, 7.41 and 8.37 μ.

EXAMPLE 62:

2-3-ethyl-4-(2-acetylaminoethylthiothiocarbonylthio)-2-oxoazetidin-1-yl-2-triphenylphosphoranylideneacetic acid p-nitrobenzyl ester (racemic cis-trans compound)

A solution of 5.52 g (11 mole) of 2-[3-ethyl-4-(2-acetylaminoethylthiothiocarbon-ylthio)-2-oxoazetidin-1-yl]-2-hydroxyacetic acid p-nitrobenzyl ester (racemic cis-trans compound) in 30 ml of absolute tetrahydrofuran is cooled to −15°, while stirring 1.02 ml (14 mmole) of thionyl chloride are added and subsequently 1.95 ml (14 mmole) of triethylamine are slowly added. The reaction mixture is stirred for 20 minutes at 0°, 150 ml of methylene chloride are added and washing is carried out with ice-cold 1N hydrochloric acid. The organic phase is dried with sodium sulphate and concentrated by evaporation in vacuo. The resulting crude 2-3-ethyl-4-(2-acetylaminoethylthiothiocarbonylthio)-2-oxoazetidin-1-yl-2-chloroacetic acid p-nitrobenzyl ester is dissolved in 3 ml of dry tetrahydrofuran, 6 g of triphenylphosphine are added and the mixture is stirred for 24 hours at room temperature. The reaction mixture is diluted with 200 ml of methylene chloride, washed with saturated aqueous sodium bicarbonate solution, dried over sodium sulphate and concentrated by evaporation in vacuo. After chromatography over silica gel with ethyl acetate, the residue yields the title compound.

TLC: $R_f$=0.19 (ethyl acetate); IR spectrum ($CH_2Cl_2$): absorption bands at 2.93, 5.70, 5.97, 6.17, 6.58, 6.99, 7.00, 8.07, 8.33 and 9.39 μ.

EXAMPLE 63:

2-(2-acetylaminoethylthio)-6-ethyl-2-penem-3-carboxylic acid p-nitrobenzyl ester (racemic cis- and trans-compound)

A catalytic amount of hydroquinone is added to a solution of 1.75 g (2.34 mmole) of 2[-3-ethyl-4-(2-acetylaminoethylthiothiocarbonylthio)-2-oxoazetidin-1-yl]-2-tri-phenyl-phos-phoranylideneacetic acid p-nitrobenzyl ester (racemic cis-trans compound) in 1500 ml of dry o-xylene and the mixture is refluxed for 7 hours while stirring under nitrogen. The solvent is evaporated off in vacuo and the residue is chromatographed over silica gel with ethyl acetate. A mixture of the cis- and trans-title compound is obtained.

The cis- and the trans-title compound may be obtained by a combination of preparative thin layer chromatography (silica gel with methyl isobutyl ketone) and column chromatography (silica gel with ethyl acetate).

cis-compound: Melting point 141°–142° (after crystallisation from methylene chloride/diethyl ether); TLC: $R_f$0.62 (methyl isobutyl ketone); IR spectrum ($CH_2Cl_2$): absorption bands at 2.93, 5.62, 5.98, 6.60, 7.46, 7.57, 8.44 and 9.09 μ.

trans-compound: Melting point 132°–133° (after crystallisation from methylene chloride/diethyl ether); TLC: $R_f$=0.56 (methyl isobutyl ketone); IR spectrum ($CH_2Cl_2$): absorption bands at 2.92, 5.62, 5.96, 6.58, 7.44, 7.58, 8.40 and 9.01 μ.

EXAMPLE 64:

2-(2-acetylaminoethylthio)-6-ethyl-2-penem-3-carboxylic acid (racemic cis- and trans-compound)

(a) 4 ml of 0.2N aqueous sodium bicarbonate solution and 200 mg of 10% palladium/carbon catalyst are added to a solution of 100 mg (0.22 mmole) of 2-(2 acetylaminoethylthio)-6-ethyl-2-penem-3-carboxylic acid p-nitrobenzyl ester (racemic cis-compound in 6 ml of absolute ethyl acetate and the mixture is stirred at normal pressure for 60 minutes under hydrogen. The catalyst is filtered off from the hydrogenated mixture over diatomaceous earth. The aqueous phase is separated off, washed with diethyl ether, acidified with 5% aqueous citric acid solution and exhaustively extracted with methylene chloride. The combined methylene chloride phases are dried over sodium sulphate, filtered, concentrated by evaporation in vacuo and dried in a high vacuum. The resulting cis-title compound has the following physico-chemical properties: melting point 153–154° (methylene chloride/diethyl ether; IR spectrum (KBr): absorption bands at 3.08, 3.22, 3.39, 3.42, 3.50, 3.77, 4.08, 5.67, 6.06, 6.21, 6.35, 6.75, 7.04, 7.69, 7.93, 8.27, 9.01, 9.62 and 14.38 μ.

b) In the safe manner the trans-title compound is obtained from 100 mg of 2-(2-acetylaminoethylthio)-ethyl-2-penem-3-carboxylic acid p-nitrobenzyl ester (racemic trans-compound).

IR spectrum (KBr): absorption bands at 3.01, 3.39, 3.44, 5.68, 6.10, 6.85, 7.75, 8.16, 8.47 and 8.93 μ.

EXAMPLE 65:

3-ethyl-4-(4-p-nitrobenzyloxycarbonylaminobutyrylthio)-2-oxoazetidine (racemic cis-trans compound in a ratio of 1:4)

A solution, prepared in the cold, of 7.95 g (26.7 mmole) of 4-p-nitrobenzyloxycarbonylaminothiobutyric acid in 26.7 ml of 1N sodium hydroxide solution is added dropwise to a pre-cooled solution of 3.24 g (20 mmole) of 3-ethyl-4-acetoxyazetidin-2-one (racemic cis-trans compound in a ratio of 6:4) in 50 ml of dioxan and the mixture is stirred for 2 hours at room temperature. The reaction mixture is exhaustively extracted with methylene chloride. The combined organic phases are dried over sodium sulphate and concentrated by evaporation in vacuo. The residue is chromatographed over silica gel with toluene/ethyl acetate (9:1, 4:1 and 1:1) and yields the title compound with the following physico-chemical properties.

TLC: $R_f$=0.10 (toluene/ethyl acetate 1:1);

IR spectrum (CH$_2$Cl$_2$): absorption bands at 2.81, 2.92, 5.66, 5.81, 5.94, 6.58, 7.52 and 8.20 μ.

The thiocarboxylic acid used as starting material is obtained as follows:

(a) A solution of 25.87 g (0.12 mmole) of p-nitrobenzyl chloroformate in 100 ml of dry dioxan is added dropwise over the course of 20 minutes to a solution of 10.30 g (0.1 mmole) of 4-aminobutyric acid in 300 ml of 1N sodium hydroxide solution in an ice bath. The reaction mixture is stirred at room temperature for 3 hours, washed with ethyl acetate and acidified with 2N hydrochloric acid. The precipitated 4-p-nitrobenzyloxycarbonylaminobutyric acid is filtered off and recrystallised from ethyl acetate; melting point 145–146°.

(b) In succession, 2.2 g (20 mmole) of triethylamine and a solution of 1.4 ml (10 mmole) of isobutyl chloroformate in 20 ml of dry methylene chloride are added dropwise to a solution, cooled to −10°, of 2.82 g (10 mmole) of 4-p-nitrobenzyloxycarbonylaminobutyric acid in 50 ml of dry methylene chloride. The reaction mixture is stirred for one hour and then a strong current of hydrogen sulphide is conveyed through for 2 hours. After acidifying with 2N sulphuric acid, the organic phase is separated off, dried and concentrated by evaporation in vacuo. The resulting 4-p-nitrobenzyloxycarbonylaminothiobutyric acid can be further processed without further purification.

EXAMPLE 66:

2-[3-ethyl-4-(4-p-nitrobenzyloxycarbonylaminobutyrylthio)-2-oxoazetidin-1-yl]-2-hydroxyacetic acid p-nitrobenzyl ester (racemic cis-trans compound)

At room temperature 6.50 g (16.45 mmole) of 3-ethyl-4-(4-p-nitrobenzyloxycarbonylaminobutyrylthio)-2-oxoazetidine (racemic cis-trans compound) and 8.41 g of 2-ethoxy-2-hydroxyacetic acid p-nitrobenzyl ester are dissolved in 160 ml of toluene and 40 ml of dimethylformamide. After adding approximately 15 g of freshly dried molecular sieves, the mixture is stirred at room temperature for 3 hours under nitrogen. The molecular sieves are filtered off and washed with dimethylformanide/toluene (1:4). The filtrate is concentrated by evaporation in vacuo, dried in a high vacuum and the residue is triturated with diethyl ether to remove unreacted 2-ethoxy-2-hydroxyacetic acid -p-nitrobenzyl ester. The crude title compound has the following physico-chemical properties:

TLC: $R_f$=0.1 (toluene/ethyl acetate 1:1); IR spectrum (CH$_2$Cl$_2$): absorption bands at 2.83, 2.90, 5.67, 5.73, 5.80, 5.99, 6.58, 7.52, 8.26 and 9.52 μ.

EXAMPLE 67:

2-[3-ethyl-4-(4-p-nitrobenzyloxycarbonylaminobutyrylthio)-2-oxoazetidin-1-yl]-2-triphenylphosphoranylideneacetic acid p-nitrobenzyl ester (racemic cis-trans compound)

(a) 3.06 ml (42 mmole) of thionyl chloride and 5.85 ml (42 mmole) of triethylamine are added dropwise, in succession, at −15° to a mixture of 10.40 g (17.2 mmole) of 2-3-ethyl-4-(4-p-nitrobenzyloxycarbonylaminobutyrylthio)-2-oxoazetidin-1-yl]-2-hydroxyacetic acid p-nitrobenzyl ester in 40 ml of absolute dioxan. The reaction mixture is stirred for 20 minutes at 0° under nitrogen, diluted with 200 ml of methylene chloride and washed with cooled 1N hydrochloric acid. The organic phase is dried and concentrated by evaporation in vacuo.

(b) The resulting crude 2-[3-ethyl-4-(4-p-nitrobenzyloxycarbonylaminobutyrylthio)-2-oxoazetidin- 1-yl]-2-chloroacetic acid p-nitrobenzyl ester is dissolved in a minimum amount of tetrahydrofuran, 9 g of triphenylphosphine are added and the mixture is stirred overnight at room temperature under nitrogen. The reaction mixture is diluted with 250 ml of methylene chloride, washed with saturated aqueous sodium bicarbonate solution, dried and concentrated by evaporation in vacuo. The residue is chromatographed over silica gel with toluene/ethyl acetate (1:1) and yields the title compound with the following physico-chemical properties:

TLC: $R_f$=0.05 (toluene/ethyl acetate 1:1); IR spectrum (CH$_2$Cl$_2$): absorption bands at 2.90, 5.73, 5.80, 5.94, 6.58, 7.52, 8.20 and 9.35 μ.

EXAMPLE 68:

6-ethyl-2-(3-p-nitrobenzyloxycarbonylaminopropyl)-2-penem-3-carboxylic acid p-nitrobenzyl ester (racemic cis-trans compound)

A catalytic amount of hydroquinone is added to a solution of 5.40 g (6.36 mmole) of 2[-3-ethyl-4-(4-p-nitrobenzyloxycarbonylaminobutyrylthio)-2-oxoazetidin-1-yl-2-triph-enylph-os-phoranylideneacetic acid -p-nitrobenzyl ester (racemic cis-trans compound) in 1500 ml of dry toluene and the mixture is stirred under nitrogen for 20 hours at 100°. The solvent is evaporated off in vacuo and the residue is chromatographed over silica gel with toluene/ethyl acetate (4:1). A mixture of the cis- and trans-title compound is obtained in the ratio of 1:10 with the following physico-chemical properties:

TLC $R_f$=0.22 (toluene/ethyl acetate 1:1); IR spectrum (CH$_2$Cl$_2$): absorption bands at 2.90, 5.62, 5.81, 5.85, 6.58, 7.52, 7.87 and 8.20 μ. By repeated chromatography the cis- and the trans-compound can be obtained in pure form.

EXAMPLE 69:

6-ethyl-2-(3-aminopropyl)-2-penem-3-carboxylic acid (racemic cis-trans compound)

2 g of disodium biphosphate and 4 g of 10% palladium/carbon catalyst are added to a solution of 2 g (3.5 mmole) of 6-ethyl-2-(3-p-nitrobenzyloxycarbonylaminopropyl)-2-penem-3-carboxylic acid p-nitrobenzyl ester (racemic cis-trans compound) in 600 ml of dioxan, 330 ml of ethanol and 600 ml of water, and the mixture is stirred at normal pressure for one hour under hydrogen. The catalyst is filtered off from the hydrogenated mixture over diatomaceous earth. The filtrate is washed 3 times with 1500 ml of ethyl acetate and lyophilised. The lyophilisate is chromatographed twice over silylated silica gel (thin layer plates ANTEC-GEL, UP-$C_{12}$) with water/acetonitrile (9:1) and yields the title compound (cis:trans approximately 1:10) with the following physico-chemical properties: TLC (ANTEC-GEL, UP-$C_{12}$) $R_f$=0.55 (water/acetonitrile 9:1); IR spectrum (KBr): absorption bands at 2.94, 3.39, 5.68, 6.41, 7.33, 7.81, 8.93, 12.82 and 14.28 $\mu$.

Using the pure cis- or trans-starting material, the pure cis- and trans-title compounds can be obtained.

EXAMPLE 70:

2-[(3S,4S)- and (3S,4R)-4-acetoxy-3-methoxy-2-oxoazetidin-1-yl-3-methylenebutyric acid $\beta$, $\beta$, $\beta$-trichloroethyl ester 0.114 ml of glacial acetic acid and 0.35 ml of trimethyl phosphite are added to 200 mg of (6S)-6-methoxypenicillanic acid $\beta,\beta,\beta$-trichloroethyl ester 1-oxide in 13 ml of absolute benzene and the mixture is refluxed for 7 hours. The solvent is evaporated off in vacuo and the residue is purified by chromatography over silica gel with toluene/ethyl acetate (19:1 and 9:1).

The title compounds can thus be separated. IR spectrum (in methylene chloride): characteristic absorption bands for (3S,4R)isomer (trans-compound) 3.42, 5.62, 5.68, 7.25, 7.35, 8.26, 9.01, 10.93 and 11.83$\mu$; (3S,4S)-isomer (cis-compound): 3.42, 5.61, 5.7, 7.25, 7.35, 8.21, 9.61 and 10.93$\mu$.

The ratio of cis to trans-compound is approximately 1:1.

EXAMPLE 71

2-[(3S,4S)- and (3S,4R)-4-acetoxy-3-methoxy-2-oxoazetidin-1-yl]-2-methylcrotonic acid $\beta,\beta,\beta$-trichloroethyl ester.

A solution of 0.93 g of 2- [(3S,4S)- and (3S,4R)-4-acetoxy-3-methoxy-2-oxoazetidin-1-yl]-3-methylenebutyric acid $\beta,\beta,\beta$-trichloroethyl ester in 60 ml of absolute methylene chloride is cooled to 0° and stirred for 10 minutes with 0.33 ml of triethylamine. The reaction mixture is then washed in succession with 4N phosphoric acid, saturated aqueous sodium bicarbonate solution and water and dried over sodium sulphate. The solvent is evaporated off in vacuo and the residue is purified by chromatography over silica gel.

IR spectrum (in methylene chloride): characteristic absorption bands at: 3.41, 5.60, 5.73, 6.13, 7.19, 7.33, 8.26, 9.09, 9.57, 10.64, 10.87 and 12.19$\mu$.

EXAMPLE 72

2-[(3S,4S)- and (3S,4R)-4-acetoxy-3-methoxy-2-oxoazetidin-1-yl]-2-oxoacetic acid $\beta,\beta,\beta$-trichloroethyl ester 3 equivalents of ozone are conveyed through a solution, cooled to −30°, of 0.91 g of 2-[(3S,4S)- and (3S,4R)-4-acetoxy-3-methoxy-2-oxoazetidin-1-yl-3-methylcrotonic acid $\beta,\beta,\beta$-trichloroethyl ester in 130 ml of methyl acetate. After the ozone treatment, the mixture is left to stand for 15 minutes at the same temperature and subsequently the excess ozone is removed by a nitrogen current. The reaction mixture is washed at 0° with a 10% aqueous sodium sulphite solution and then with sodium chloride solution. The combined aqueous solutions are reextracted a further three times with methyl acetate. The combined organic extracts are dried over sodium sulphate and concentrated by evaporation in vacuo.

IR spectrum (in methylene chloride): characteristic absorption bands at 3.41, 5.46, 5.68, 5.81, 7.27, 7.43, 8.23, 8.40, 9.52 and 9.90$\mu$.

EXAMPLE 73

(3S,4S)- and (3S,4R)-4-acetoxy-3-methoxy -2-oxoazetidine

A solution of 120 mg of 2- [(3S,4S)- and (3S,4R)-4-acetoxy-3-methoxy-2-oxoazetidin-1-yl-2-oxoacetic acid $\beta,\beta,\beta$-trichloroethyl ester in 25 ml of methanol, 3.5 ml of methyl acetate and 0.5 ml of water is refluxed for 20 minutes. The solvent is evaporated off in vacuo and the residue yields, after chromatography over silica gel with toluene/ethyl acetate (9:1) the pure (3S,4R)-4-acetoxy-3-methoxy-2-oxoazetidine;

IR spectrum (in methylene chloride): characteristic absorption bands at 2.96, 3.42, 5.57, 5.73, 7.30, 8.23, 8.70, 8.85, 9.62, 10.0 and 10.20$\mu$, and on further elution the pure (3S,4S)-4-acetoxy-3-methoxy -2-oxoazetidine; IR spectrum (in methylene chloride): characteristic absorption bands at 2.94, 3.41, 5.56, 5.73, 7.35, 7.49, 8.20 and 9.52$\mu$.

EXAMPLE 74

(3S,4R)-4-(2-p-nitrobenzyloxycarbonylaminoethylthiothiocarbonylthio)-3-methoxy-2-oxoazetidine A solution of 422 mg of potassium 2-p-nitrobenzyloxycarbonylaminoethyl trithiocarbonate in 1 ml of water is added dropwise at room temperature under, a nitrogen atmosphere to a solution of 159 mg (1 mmole) of (3S,4S)-4-acetoxy-3-methoxy-2-oxoazetidine in 3 ml of phosphate buffer of a pH of 7 and 0.2 ml of dioxan, and the mixture is stirred at the same temperature for 30 minutes. The reaction mixture is exhaustively extracted with methylene chloride. The combined organic phases are dried over sodium sulphate and concentrated by evaporation in vacuo. The residue is chromatographed over silica gel and yields the title compound with the following IR spectrum (in methylene chloride): characteristic absorption bands at 2.95, 5.62, 5.78, 6.21, 6.56, 7.41, 8.26 and 9.25$\mu$.

EXAMPLE 75

2-[(3S,4R)-4-(2-p nitrobenzyloxycarbonylaminoethylthiothiocarbonylthio)-3-methoxy-2-oxoazetidin-1-yl]-2-hydroxyacetic acid p-nitrobenzyl ester Analogously to Example 23, 646 mg (1.5 mmole) of (3S,4R)-4-(2-p-nitrobenzyloxycarbonylaminoethylthiothiocarbonylthio)-3-methoxy-2-oxoazetidine in 22 ml of absolute toluene and 5.5 ml of absolute dimethylformamide are reacted with 848 mg of 2-ethoxy-2-hydroxyacetic acid p-nitrobenzyl ester in the presence of freshly dried molecular sieves. After working up and chromatography over silica gel the title compound is obtained.

IR spectrum (in methylene chloride): characteristic absorption bands at 5.62, 5.7, 5.78, 6.56, 7.41 and 8.26μ.

EXAMPLE 76

2-[(3S,4R)-4-(2-p-nitrobenzyloxycarbonylaminoethylthiothiocarbonylthio)-3-methoxy-2-oxoazetidin-1-yl]-2-triphenylphosphoranylideneacetic acid p-nitrobenzyl ester Analogously to Example 24, 0.12 ml of thionyl chloride and 0.23 ml of triethylamine in 0.23 ml of absolute tetrahydrofuran are added to a solution of 640 mg of 2-[(3S,4R)-4-(2-p-nitrobenzyloxycarbonylaminoethylthiothiocarbonylthio)-3-methoxy-2-oxoazetidin-1-yl]-2-hydroxyacetic acid p-nitrobenzyl ester in 4.5 ml of absolute tetrahydrofuran. After reacting and working up, 0.54 g of triphenylphosphine is added to the crude 2-[(3S,4R)-4-(2-p-nitrobenzyloxycarbonylaninoethylthiothiocarbonylthio)-3-methoxy-2-oxoazetidin-1-yl]-2-chloroacetic acid p-nitrobenzyl ester, obtained as intermediate, in 1.15 ml of absolute tetrahydrofuran. After working up and chromatography over silica gel, the title compound is obtained.

IR spectrum (in methylene chloride): characteristic absorption bands at 3.4, 5.7, 5.78, 6.15, 6.55, 7.45 and 8.26μ.

EXAMPLE 77

(6S,5R)-2-(2-p-nitrobenzyloxycarbonylaminoethylthio)-6-methoxy-2-penem-3-carboxylic acid p-nitrobenzyl ester Analogously to Example 25, a solution of 500 mg of 2-[(3S,4R)-4-(2-p-nitrobenzyloxycarbonylaminoethylthiothiocarbonylthio)-3-methoxy-2-oxoazetidin-1-yl]-2-triphenylphosphoranylideneacetic acid p-nitrobenzyl ester in 165 ml of absolute o-xylene is stirred under reflux.

After working up and chromatography over silica gel with toluene/ethyl acetate (19:1 to 9:1) the title compound is obtained.

IR spectrum (CH$_2$Cl$_2$): absorption bands at 5.57, 5.78, 5.9, 6.55, 7.45 and 8.26μ.

EXAMPLE 78

(6S,5R)-2-(2-aminoethylthio)-6-methoxy-2-penem-3-carboxylic acid

Analogously to Example 69, a solution of 295 mg of (6S,5R)-2-(2-p-nitrobenzyloxycarbonylaminoethylthio)-6-methoxy-2-penem-3-carboxylic acid p-nitrobenzyl ester in 85 ml of dioxan, 47 ml of ethanol and 85 ml of water is treated with 286 mg of disodium hydrogen phosphate and 570 mg of a 10% palladium-on-carbon catalyst, and the mixture is stirred in a hydrogen atmosphere under normal pressure. After reacting and working up, the title compound with the following IR spectrum (KBr) is obtained: Absorption bands at 2.8–4.16, 5.68, 6.41 and 8.26μ.

EXAMPLE 79

(3S,4R)-4-(4-p-nitrobenzyloxycarbonylaminobutyrylthio)-3-methoxy-2-oxoazetidine

Analogously to Example 55b), an aqueous solution of 480 mg of 4-p-nitrobenzyloxycarbonylaminothiobutyric acid sodium salt is added to 159 mg of (3S,4S)-4-acetoxy-3-methoxy-2-oxoazetidine in 6 ml of a phosphate buffer of a pH of 7 and 0.4 ml of dioxan After working up and chromatography over silica gel, the title compound with the following IR spectrum (CH$_2$Cl$_2$) is obtained: characteristic absorption bands at 2.95, 5.6, 5.78, 5.87, 6.56, 7.41 and 8.26μ.

EXAMPLE 80

2-[(3S,4R)-4-(4 p-nitrobenzyloxycarbonylaminobutyrylthio)-3-methoxy-2-oxoazetidin-1-yl]-2-hydroxyacetic acid p-nitrobenzyl ester Analogously to Example 23, 400 mg of (3S,4R)-(4-p-nitrobenzyloxycarbonylaminobutyrylthio)-3-methoxy-2-oxoazetidine in 15 ml of absolute toluene and 3.7 ml of absolute dimethylformamide are reacted with 565 mg of 2-ethoxy-2-hydroxyacetic acid p-nitrobenzyl ester in the presence of freshly dried molecular sieves. After working up and chromatography over silica gel, the title compound with the following IR spectrum (CH$_2$Cl$_2$) is obtained: characteristic absorption bands at 5.6, 5.7, 5.78, 5.87, 6.56, 7.41 and 8.26μ.

EXAMPLE 81

2-[(3S,4R)-4-(4-p-nitrobenzyloxycarbonylaminobutyrylthio)-3-methoxy-2-oxoazetidin-1-yl]-2-triphenylphosphoranylideneacetic acid p-nitrobenzyl ester Analogously to Example 24, 0.12 ml of thionyl chloride and then 0.23 ml of triethylamine in 0.23 ml of absolute tetrahydrofuran are added to a solution of 606 mg of 2-[(3S,4R)-4-p-nitrobenzyloxycarbonylaminobutyrylthio)-3-methoxy-2-oxoazetidin-1-yl]-2-hydroxyacetic acid p-nitrobenzyl ester in 4.5 ml of absolute tetrahydrofuran. After reacting and working up, 0.54 g of triphenylphosphine is added to the resulting crude 2-[(3S,4R)-4-(4-p-nitrobenzyloxycarbonylaminobutyrylthio)-3-methoxy-2-oxoazetidin-1-yl]-2-chloroacetic acid p-nitrobenzyl ester in 1.15 ml of absolute tetrahydrofuran. Working up and chromatography over silica gel produce the title compound with the following IR spectrum (CH$_2$Cl$_2$): characteristic absorption bands at 5.7, 5.78, 5.9, 6.15, 6.55, 7.45 and 8.26μ.

EXAMPLE 82

(6S,5R)-2-(3-p-nitrobenzyloxycarbonylaminopropyl)-6-methoxy-2-penem-3-carboxylic acid p-nitrobenzyl ester Analogously to Example 68, a solution of 400 mg of 2- [(3S,4R)-4-(4-p-nitrobenzyloxycarbonylaminobutyrylthio-3-methoxy-2-oxoazetidin-1-yl]-2-triphenylphosphoranylideneacetic acid p-nitrobenzyl ester in 160 ml of absolute toluene is stirred under reflux. After working up and chromatography over silica gel with toluene/ethyl acetate (19:1 to 9:1) the title compound is obtained.

IR spectrum ($CH_2Cl_2$): characteristic absorption bands at 5.57, 5.78, 5.85, 6.55, 7.45 and 8.26μ.

EXAMPLE 83

(6S,5R)-2-(3-aminopropyl-6-methoxy-2-penem-3-carboxylic acid.

Analogously to Example 69, a solution of 572 ml of (6S,5R)-2-(3-p-nitrobenzyloxycarbonylaminopropyl)-6-methoxy-2-penem-3-carboxylic acid p-nitrobenzyl ester in 170 m of dioxan, 94 ml of ethanol and 170 ml of water is treated with 571 mg of disodium hydrogen phosphate and 1.14 g of a 10% palladium-on-carbon catalyst and is stirred in a hydrogen atmosphere under normal pressure.

After reacting and working up, the title compound with the following IR spectrum (KBr) is obtained: Absorption bands at 2.75–4.15, 5.67, 6.42 and 8.25μ.

EXAMPLE 84

2-[(3S,4S)- and (3S,4R)-4-chloro-3-methoxy-2-oxoazetidin-1-yl]-3-methylcrotonic acid β,β,β-trichloroethyl ester 3.25 ml of a 1.1M chlorine solution in $CCl_4$ are added dropwise at −80° to 612 mg of (6S)-6-methoxypenicillanic acid β,β,β-trichloroethyl ester in 9 ml of absolute methylene chloride.

After stirring for 2 hours at −80°, the reaction mixture is warmed up to room temperature in the course of one hour. The solvent is evaporated off in vacuo and the residue is chromatographed over silica gel 10 % water. The title compounds have the following IR spectrum (in $CH_2Cl_2$): characteristic absorption bands at 3.41, 5.60, 5.76, 6.15, 7.22, 7.35, 8.33, 9.09, 9.52 and 12.20μ. In the resulting mixture the ratio of (3S,4S)-compound to (3S,4R)-compound is 1:10.

EXAMPLE 85

2-[(3S,4S)- and (3S,4R)-4-chloro-3-methoxy-2-oxoazetidin-1-yl]-2-oxoacetic acid β,β,β-trichloroethyl ester 3 equivalents of ozone are conveyed through a solution, cooled to −35° C., of 210 mg of 2-[(3S,4S)- and (3S,4R)-4-chloro-3-methoxy-2-oxoazetidin-1-yl]-3-methylcrotonic acid β,β,β-trichloroethyl ester in 30 ml of methyl acetate. After the ozone treatment, the mixture is left to stand for 15 minutes at the same temperature and then the excess ozone is removed by a current of nitrogen. The reaction mixture is washed at 0° with a 10% aqueous sodium bisulphite solution and then with sodium chloride solution. The combined aqueous solutions are re-extracted a further 3 times with methyl acetate. The organic extracts are dried over sodium sulphate and concentrated by evaporation in vacuo. The crude title compound has the following IR spectrum (in $CH_2Cl_2$): characteristic absorption bands at 3.41, 5.46, 5.65, 5.80, 7.46, 8.23, 8.47, 8.89, 9.57, 9.95 and 11.90μ.

EXAMPLE 86

(3S,4S)- and (3S,4R)-4-chloro-3-methoxy-2-oxoazetidine

A solution of 339 mg of 2-[(3S,4S)- and (3S,4R)-4-chloro-3-methoxy-2-oxoazetidin-1-yl]-2-oxoacetic acid β,β,β-trichloroethyl ester and 197 mg of 2,4-dinitrophenylhydrazine in 9 ml of tetrahydrofuran are refluxed for 30 minutes. The solvent is evaporated off and the residue is chromatographed over silica gel. The title compound has the following IR spectrum ($CH_2Cl_2$): Characteristic absorption bands at 2.94, 5.56, 8.26 and 9.09μ.

EXAMPLE 87

(3S,4R)-4-(4-p-nitrobenzyloxycarbonylaminobutyryl-thio)-3-methoxy-2-oxoazetidine A solution of 350 mg of 4-p-nitrobenzyloxycarbonylaminothiobutyric acid sodium salt in 4 ml of water is added dropwise to a solution of 135 mg of (3S,4R)-4-chloro-3-methoxy-2-oxoazetidine in 6 ml of a phosphate buffer of a pH of 7 and 0.4 ml of dioxan in the presence of 150 mg of sodium iodide.

After stirring for 30 minutes at room temperature the mixture is exhaustively extracted with methylene chloride. After removing and drying the organic phase over sodium sulphate, the solvent is evaporated off in vacuo and the residue is chromatographed over silica gel. The title compound has the following IR spectrum ($C_2Cl_2$): Absorption bands at 2.95, 5.6, 5.78, 5.87, 6.56, 7.41 and 8.26μ.

EXAMPLE 88

Using corresponding starting materials and by way of corresponding intermediates, the following compounds are obtained analogously to the aforegoing Examples:

6-ethyl-2-(2-aminoethylthio)-2-penem-3-carboxylic acid, 6-hydroxymethyl-2-penem-3-carboxylic acid, 6-hydroxymethyl-2-methyl-2-penem-3-carboxylic acid, 6-hydroxymethyl-2-(3-aminopropyl)-2-penem-3-carboxylic acid, 6-hydroxymethyl-2-(3-acetylaminopropyl)-2-penem-3-carboxylic acid, 6-hydroxymethyl-2-ethylthio-2-penem-3-carboxylic acid, 6-hydroxymethyl-2-(2-aminoethylthio)-2-penem-3-carboxylic acid, 6-hydroxymethyl-2-(2-acetylaminoethylthio-2-penem-3-carboxylic acid, 6-(1-hydroxyethyl)-2-penem-3-carboxylic acid, 6-(1-hydroxyethyl)-2-methyl-2-penem-3-carboxylic acid, 6-(1-hydroxyethyl)-2-(3-aminopropyl)-2-penem-3-carboxylic acid, 6-(1-hydroxyethyl)-2-(3-acetylaminopropyl)-2-penem-3-carboxylic acid, 6-(1-hydroxyethyl)-2-ethylthio-2-penem-3-carboxylic acid, 6-(1-hydroxyethyl)-2-(2-aminoethylthio)-2-penem-3-carboxylic acid, 6-(1-hydroxyethyl)-2-(2-acetylaminoethylthio)-2-penem-3-carboxylic acid, 6-methoxy-2-penem-3-carboxylic acid, 6-methoxy-2-(3-acetylaminopropyl)-2-penem-3-carboxylic acid, 6-methoxy-2-ethylthio-2-penem-3-carboxylic acid, 6-methoxy-2-(2-acetylaminoethylthio)-2-penem-3-carboxylic acid, 6-methoxy-2-(1,3,4-thiadiazol-2-ylthio)-2-penem3-carboxylic acid, 6-(2 hydroxyprop-2-yl)-2-penem-3-carboxylic acid, 6-(2-hydroxyprop-2-yl)-2-methyl-2-penem-3-carboxylic acid, 6-(2-hydroxyprop-2-yl)-2-(3-aminopropyl)-2-penem-3-carboxylic acid, 6-(2-hydroxyprop-2-yl)-2-(3-acetylaminopropyl)-2-penem-3-carboxylic acid, 6-(2-hydroxyprop-2-yl)-2-ethylthio-2-penem-3carboxylic acid, 6-(2-hydroxyprop-2-yl)-2-(2-aminoethylthio-2-penem-3-carboxylic acid, 6-(2-hydroxyprop-2-yl)-2-(2-acetylaminoethylthio-2-penem-3-carboxylic acid, both in racemic and in optically active form, and their salts.

EXAMPLE 89

Dry ampoules or phials, containing 0.5 g of 6-ethyl-2-(3-aminopropyl)-2-penem -3-carboxylic acid as active substance, are produced as follows: Composition (for 1 ampoule or phial):

| Composition (for 1 ampoule or phial): | |
|---|---|
| active substance | 0.5 g |
| mannitol | 0.05 g |

A sterile aqueous solution of the active substance and the mannitol is subjected to freeze-drying under aseptic conditions in 5 ml ampoules or 5 ml phials and the ampoules or phials are sealed and examined.

EXAMPLE 90

Dry ampoules or phials, containing 0.25 g of 6-ethyl-2-(3-aminopropyl)-2-penem-3-carboxylic acid as active substance, are produced as follows:

| Composition (for 1 ampoule or phial): | |
|---|---|
| active substance | 0.25 g |
| mannitol | 0.025 g |

A sterile aqueous solution of the active substance and the mannitol is subjected to freeze-drying under aseptic conditions in 5 ml ampoules or 5 ml phials and the ampoules or phials are sealed and examined.

What is claimed is:

1. A compound of the formula

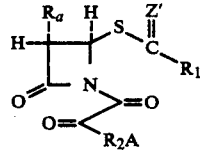

wherein $R_a$ is (1R)-1-hydroxyethyl;

$R_2A$ together with the carbonyl to which it is attached is a protected carboxyl group;

$R_1$ is —R, in which R is $C_{1-7}$ alkyl, phenyl, phenylalkyl having 7–13 carbon atoms, or heterocyclyl or heterocyclylalkyl having up to 10 carbon atoms and up to 4 ring hetero atoms selected from nitrogen, oxygen, and sulphur, with the proviso that two oxygen atoms or two sulfur atoms or one oxygen atom and one sulfur atom are not adjacent to each other, each R being unsubstituted or substituted by amino, mono $C_{1-7}$ alkylamino, di-$C_{1-7}$ alkylamino, hydroxy, $C_{1-7}$ alkoxy, mercapto, $C_{1-7}$ alkylthio, chloro, bromo, fluoro, or by carboxyl; and $Z'$ is oxygen, sulfur, methoxycarbonylmethylidene or 1-menthyloxycarbonylmethylidene; and the functional groups in the radicals designated $R_a$ and $R_1$ are either in protected or unprotected form.

2. A compound of the formula

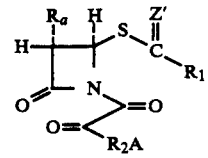

wherein $R_a$ is (1R)-1-hydroxyethyl;

$R_2A$ together with the carbonyl to which it is attached is a protected carboxyl group;

$R_1$ is SR, in which R is $C_{1-7}$ alkyl, phenyl, phenylalkyl having 7–13 carbon atoms, or heterocycyl having up to 10 carbon atoms and up to 4 ring hetero atoms selected from nitrogen, oxygen, and sulphur, with the proviso that two oxygen atoms or two sulfur atoms or one oxygen atom and one sulfur atom are not adjacent to each other, each R being unsubstituted or substituted by amino, mono $C_{1-7}$ alkylamino, di-$C_{1-7}$alkylamino, hydroxy, $C_{1-7}$ alkoxy, mercapto, $C_{1-7}$ alkylthio, nitro, chloro, bromo, fluoro, cyano or carboxyl; and $Z'$ is oxygen, sulfur, methoxycarbonylmethylidene or 1-menthyloxycarbonylmethylidene; and the functional groups in the radicals designated $R_a$ and $R_1$ are either in protected or unprotected form.

3. The compound of the formula

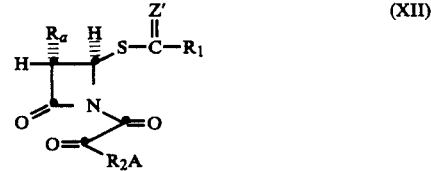 (XII)

wherein $R_a$ is (1R)-1-hydroxyethyl;

$R_1$ is methylthio, ethylthio, aminoethylthio, 3-amino propylthio, 4-aminobutylthio, 5-aminopentylthio, methyl, 2-furyl, 2-thienyl, 2-pyridyl, or (1-methyltetrazol-5-yl)thio; and $R_2A$ together with the carbonyl to which it is attached is a protected carboxyl group, and $Z'$ is oxygen or sulphur.

4. A compound of the formula

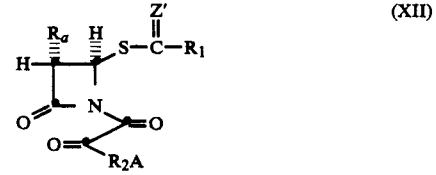 (XII)

wherein $R_a$ is hydroxymethyl or (1R)-1-hydroxyethyl; $R_2A$ together with the carbonyl to which it is attached is a protected carboxyl group;

$R_1$ is (a), lower alkyl, hydroxy-lower alkyl, lower alkoxy-lower alkyl, lower alkanoyloxy-lower alkyl, lower alkylthio-lower alkyl, amino-lower alkyl, lower alkanoyl-amino-lower alkyl, or carboxy-lower alkyl, (b) phenyl which is unsubstituted or substituted by lower alkyl, lower alkoxy, hydroxy, halogen, nitro, or by amino, (c) furyl, thienyl, or pyridyl, or (d) lower alkenylthio or lower alkylthio which is unsubstituted or substituted by lower alkoxy, lower alkanoyloxy, lower alkoxycarbonyl, Carbamoyl, cyano, nitro, amino, lower alkyl amino, di-lower alkyl amino, lower alkanoyl amino; or di-lower alkanoyl amino; and $Z'$ is oxygen, sulfur, or a methoxycarbonylmethylidene or 1-menthyloxycarbonylmethylidene; and the functional groups in the radicals designated $R_a$ and $R_1$ are either in protected or unprotected form.

5. The compound of claim 4 wherein $R_a$ is hydroxymethyl and $R_1$ is ethylthio.

6. The compound of claim 4 wherein $R_a$ is (1R)1-hydroxyethyl and $R_1$ is 3-aminopropyl.

7. The compound of claim 4 wherein $R_a$ is (1R)-1-hydroxyethyl and $R_1$ is ethylthio.

8. The compound of claim 4 wherein $R_a$ is (1R)-1-hydroxyethyl and $R_1$ is
ethylthio, methylthio, aminomethylthio, 3-aminopropylthio, 4-aminobutylthio, methyl, 2-furyl, 2-thienyl, or 2-pyridyl.

9. The compound of claim 4 wherein said $R_1$ amino-lower alkyl-thio is amino methylthio or amino-$C_3$-$C_7$ alkylthio.

10. The compound of claim 2 wherein said $R_1$ amino-lower alkyl-thio is amino methylthio or amino-$C_3$-$C_7$ alkylthio.

11. The compound of claim 4 wherein
$R_2A$ is 2-halo lower alkoxy, 2-lower alkylsulfonyl-lower alkoxy, tert.-lower alkoxy, diphenylmethoxy, 4'-dimethoxydiphenyl methoxy, lower alkenyloxy, lower alkoxyphenyl-lower alkoxy, nitrobenzyloxy, furfuryloxy, acetonyloxy, phenacryloxy, 2,4-dioxo-3-pentoxy, 1-methoxycarbonyl-2-oxopropoxy, 1-ethoxycarbonyl-2oxopropoxy, 2-cyanoethoxy, 2-cyano-2-phenylethoxy, 2-tri-loweralkylsilylethoxy, 2-tri-phenylsilylethoxy, 2-tetrahydrofuryloxy, 2-tetrahydropyranyloxy, 2,3-dihydro-2-pyranyloxy, nitrophenoxy, polyhalophenoxy, or lower alkoxy.

12. The compound of claim 2 wherein
$R_2A$ is 2-halo lower alkoxy, 2-lower alkylsulfonyl-lower alkoxy, tert.-lower alkoxy, diphenylmethoxy, 4,4'-dimethoxyldiphenyl methoxy, lower alkenyloxy, lower alkoxyphenyl-lower alkoxy, nitrobenzyloxy, furfuryloxy, acetonyloxy, phenacyloxy, 2,4-dioxo-3-pentoxy, 1-methoxycarbonyl-2-oxopropoxy, 1-ethoxy-carbonyl-2-oxopropoxy, 2-cyanoethoxy, 2-cyano-2-phenylethoxy, 2-tri-loweralkylsilylethoxy, 2-tri-phenylsilylethoxy, 2-tetrahydrofuryloxy, 2-tetrahydropyranyloxy, 2,3-dihydro-2-pyranyloxy, nitrophenoxy, polyhalophenoxy, or lower alkoxy.

* * * * *